US008491897B2

(12) United States Patent
Eroglu et al.

(10) Patent No.: US 8,491,897 B2
(45) Date of Patent: Jul. 23, 2013

(54) TREATMENT OF NEUROPATHIC PAIN USING ANTI-THROMBOSPONDIN ANTIBODIES

(75) Inventors: Cagla Eroglu, Durham, NC (US); Ben A. Barres, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 12/905,930

(22) Filed: Oct. 15, 2010

(65) Prior Publication Data

US 2011/0104181 A1   May 5, 2011

Related U.S. Application Data

(63) Continuation of application No. 12/191,884, filed on Aug. 14, 2008, now abandoned.

(60) Provisional application No. 60/966,073, filed on Aug. 23, 2007, provisional application No. 61/052,551, filed on May 12, 2008.

(51) Int. Cl.
*A61K 39/395* (2006.01)

(52) U.S. Cl.
USPC .................. 424/133.1; 424/139.1; 424/145.1

(58) Field of Classification Search
None
See application file for complete search history.

(56) References Cited

U.S. PATENT DOCUMENTS

| 4,087,544 | A | 5/1978 | Satzinger et al. |
|---|---|---|---|
| 5,166,320 | A | 11/1992 | Wu et al. |
| 5,720,720 | A | 2/1998 | Laske et al. |
| 5,807,683 | A | 9/1998 | Brenner |
| 5,958,792 | A | 9/1999 | Desai et al. |
| 6,004,617 | A | 12/1999 | Schultz et al. |
| 6,077,954 | A | 6/2000 | Cook et al. |
| 6,498,018 | B1 | 12/2002 | Carpenter |
| 6,518,289 | B1 | 2/2003 | Bryans et al. |
| 6,541,255 | B1 | 4/2003 | Snyder et al. |
| 6,638,501 | B1 | 10/2003 | Bjornson et al. |
| 6,683,112 | B2 | 1/2004 | Chen et al. |
| 6,818,418 | B1 | 11/2004 | Lipovsek et al. |
| 6,979,724 | B2 | 12/2005 | Lerman et al. |
| 2002/0012903 | A1 | 1/2002 | Goldman et al. |
| 2003/0166017 | A1 | 9/2003 | McCarthy |
| 2004/0053875 | A1 | 3/2004 | Kreutzer et al. |
| 2005/0192353 | A1 | 9/2005 | Barrett et al. |
| 2006/0019880 | A1 | 1/2006 | Barres et al. |

FOREIGN PATENT DOCUMENTS

| EP | 0 453 242 A1 | 10/1991 |
|---|---|---|
| EP | 0 453 242 B1 | 10/1991 |
| WO | WO-94/08051 A1 | 4/1994 |
| WO | WO-99/32619 A1 | 7/1999 |
| WO | WO-00/44895 A1 | 8/2000 |
| WO | WO-01/29058 A1 | 4/2001 |
| WO | WO-01/36646 A1 | 5/2001 |

OTHER PUBLICATIONS

Agah, A. et al. (2004). "Thrombospondin 2 Levels are Increased in Aged Mice: Consequences for Cutaneous Wound Healing and Angiogenesis," *Matrix. Biol.* 22:539-547.
Alberts, B. et a al. (2002). *Molecular Biology of the Cell,* Fourth Edition, Garland Science, New York, New York, p. 129.
Apella, E. et al. (Apr. 1988). "Structure and Function of Epidermal Growth Factor-Like Regions in Proteins," *FEBS Lett.* 231(1):1-4.
Arber, S. et al. (Nov. 15, 2005). "Thrombospondin-4 an Extracellular Matrix Protein Expressed in the Developing and Adult Nervous System Promotes Neurite Outgrowth," *J. Cell Biol.* 131(4):1083-1094.
Arikkath, J. et al. (2003). "Auxiliary Subunits: Essential Componenets of the Voltage-Gated Calcium Complex," *Curr. Opin. Neurobiol.* 13:298-307.
Ashkenazi, A. et al. (1995). "Immunoadhesins: An Alternative to Human Monoclonal Antibodies," *Methods* 8:104-115.
Ashkenazi, A. et al. (1997). "Immunoadhesins as Research Tools and Therapeutic Agents," *Current Opinion in Immunology* 9:195-200.
Baldwin, J.J. et al. (1995). "Synthesis of a Small Molecule Combinatorial Library Encoded with Molecular Tags," *J. Am. Chem. Soc.* 117(20):5588-5589.
Balis, F. et al. (1989). "Central Nervous System Pharmacology of Antileukemic Drugs," *Am. J. Pediatr. Hematol. Oncol.* 11(1):74-86.
Baron, R. (2009). "Neuropathic Pain: A Clinical Perspective," Handbook Exp. Pharmacol. 194:3-30.
Baum, R.M. (Feb. 7, 1994). "Cobinatorial Approaches Provide Fresh Leads for Medicinal Chemistry," *Chem & Eng. News* 72:20-25.
Borchardt, A. et al. (1994). "Synthetic Receptor Binding Elucidated with an Encoded Combinatorial Library," *J. Am. Chem. Soc.* 116(1):373-374.
Bornstein, P. (1992). "Thrombospondins: Structure and Regulation of Expression," *FASEB J.* 6:3290-3299.
Boroujerdi, A. et al. (2008). "$Ca^{2+}$ Channel $\alpha_2\delta$-1 & Thrombospondin-4 Proteins in Spinal Synaptogenesis: A Novel Mechanism of Neuropathic Pain," *OASIS—Online Abstract Submission and Invitation System,* located at <www.abstractonline.com/viewer/ViewAbstractPrintFriendlyVersi...>, last visited on Jun. 4, 2008, 2 pages.
Burbaum, J.J. et al. (Jun. 1995). "A Paradigm for Drug Discovery Employing Encoded Combinatorial Libraries," *Proc. Natl. Acad. Sci. USA* 92:6027-6031.
Canti , C.et al. (Aug. 9, 2005). "The Metal-Ion-Dependent Adhesion Site in the Von Willebrand Factor—A Domain of the $\alpha_2\delta$ Subunits is Key to Trafficking Voltage-Gated $Ca^{2+}$ Channels,"*Proc. Natl. Acad. Sci. USA* 102(32):11230-11235.
Canti, C. et al. (2003). "Calcium Channel $\alpha2\delta$ Subunits: Structure, Functions and Target Site for Drugs," *Curr. Neuropharmacology*1 (3):209-217.

(Continued)

*Primary Examiner* — Elizabeth C Kemmerer
*Assistant Examiner* — Kimberly A Ballard
(74) *Attorney, Agent, or Firm* — Morrison & Foerster LLP

(57) ABSTRACT

The present invention describes methods and compositions for modulating synaptogenesis and axon and/or dendritic growth. The methods include the use of agents that modulate a thrombospondin and/or an $\alpha2\delta$ subunit of a calcium channel.

6 Claims, 14 Drawing Sheets

OTHER PUBLICATIONS

Carlson et al. (Oct. 2005). "Structure of the Calcium-Rich Signature Domain of Human Thrombospondin-2," *Nature Structural & Molecular Bilogy* 12(1):910-914.

Chaplan, S.R. et al. (1994). "Quantitative Assessment of Tactile Allodnia in the Rat Paw," *J. Neuros. Methods.* 53:55-63.

Chen, H. et al. (Aug. 25, 2000). "Cartilage Oligomeric Matrix Protein Is a Calcium-Binding Protein, and a Mutation in Its Type 3 Repeats Causes Conformational Changes," *J. Biol. Chem.* 275(34):26538-26544.

Christopherson, K.S. et al. (Feb. 11, 2005). "Thrombospondins Are Astrocyte-Secreted Proteins that Promote CNS Snyaptogenesis," *Cell* 120:421-433.

Crooke, S.T. et al. (1996). "Progress in Antisense Oligonucleotide Therapeutics," *Ann. Rev. Pharmacology & Toxicology* 36:107-129.

Davies, A. et al. (2007, e-pub. Apr. 2, 2007). "Fucntional Biology of the $\alpha_2\delta$ Subunits of Voltage-Gated Calcium Channels," *TRENDS in Pharmacol Sci.* 28(5):220-228.

Dewitt, S.H. et al. (Aug. 1993). "'Diversomers': An Approach to Nonpeptide, Nonoligomeric Chemical Diversity," *Proc. Natl. Acad. Sci. USA* 90:6909-6913.

Dixon, W.J. (1980). "Efficient Analysis of Experimental Observations," *Ann. Rev. Pharmacol. & Toxicol.* 20:441-462.

Dolmetsch, R.E. et al. (Oct. 12, 2001). "Signaling to the Nucleus by an L-Type Calcium Channel-Calmodulin Complex trhough the MAP Kinase Pathway," *Science* 294:333-339.

Engel, J. (Jul. 1989). "EGF-Like Domains in Extracellular Matrix Proteins: Localized Signals for Growth and Differentiation?" *FEBS Lett.* 251(1,2):1-7.

Erzurumulu, R.S. et al. (2006, e-pub. Jan. 23, 2006). "Molecular Determinants of the Face Map Development in the Trigeminal Brainstem," *The Anatomical Record* 288A:121-134.

Field, M.J. et al. (Nov. 14, 2006). "Identification of the $\alpha_2$-$\delta$-1 Subunit of Voltage-Dependent Calcium Channels as Molecular Target for Pain Mediating the Analgesic Actions of Pregabalin," *Proc. Natl. Acad. Sci.* 103:17537-17542.

Friedler, A. et al. (Aug. 4, 2000). "Development of a Functional Backbone Cyclic Mimetic of the HIV-1 Tat Arginine-Rich Motif," *J. Biol. Chem.* 275(31):23783-23789.

Gurnett, C.A. et al. (Jul. 18, 1997). "Extracellular Interaction of the Voltage-Dependent $Ca^{2+}$ Channel $\alpha_2\delta$ and $\alpha_a$ Subunits," *J. Biol. Chem.* 272(29):18508-18512.

Hua, X-Y. et al. (1998). "Spinal Neurokinin NK1 Receptor Down-Regulation and Antinociception: Effects of Spinal NK1 Receptor Antisense Pligonucleotides and NK1 Receptor Occupancy," *J. Neurochem.* 70:688-698.

Iles, D.E. et al. (1994). "Localization of the Gene Encoding the $\alpha_2/\delta$-Subunits of the L-Type Voltage-Dependent Calcium Channel to Chromosome 7q and Analysis of the Segregation of Flanking Markers in Malignant Hyperthermia Susceptible Families," *Hum. Molec. Genet.* 3(6):969-975.

International Preliminary Report on Patentability, issued on Feb. 24, 2010, for PCT Patent Application No. PCT/US08/09747, filed on Aug. 14, 2008, 8 pages.

International Search Report mailed on Dec. 22, 2008, for PCT Patent Application No. PCT/US08/09747, filed on Aug. 14, 2008, 1 page.

Ji, R-R. et al. (Dec. 1994). "Galanin Antisense Oligonucleotides Reduce Galanin Levels in Dorsal Root Gangila and Induce Autotomy in Rats after Axotomy," *Proc. Natl. Acad. Sci. USA* 91:12540-12543.

Kim, D. et al. (Aug. 18, 2008). "Thrombospondins Mediate Neuropathic Pain Processing," *OASIS—Online Abstract Submission and Invitation System,* located at <www.abstractonline.com/viewer/ViewAbstractPrintFriendly.asp?MKey={C9574065...>, last visited on Aug. 4, 2008, 1 page.

Kim, S.H. et al. (1992). "An Experimental Model for Peripheral Neuropathy Produced by Segmental Spinal Nerve Ligation in the Rat," *Pain* 50:355-363.

Klugbauer, N. et al. (Dec. 2003). "Calcium Channel $\alpha_2\delta$ Subunits: Differential Expression, Function, and Drug Binding," *Bioenergetics and Biomembranes* 35(6):639-647.

Kroenke, K. et al. (2009). "Pharmacotherapy of Chronic Pain: A Synthesis of Recommendations from Systematic Reviews," *Gen Hosp Psychiatry* 31:206-219.

Langer, R. (Sep. 28, 1990). "New Methods of Drug Discovery," *Science* 249:1527-1533.

Lawler, J. et al. (Feb. 10, 1995). "Characterization of Human Thrombospondin-4," *J. Biol. Chem.* 270(6):2809-2814.

Li, C-Y. et al. (Sep. 29, 2004). "Spinal Dorsal Horn Calcium Channel $\alpha_2\delta$-1 Subunit Upregulation Contributes to Peripheral Nerve Injury-Induced Tactile Allodynia," *J. Neurosci.* 24(39):8494-8499.

Li, C-Y. et al. (Nov. 2006). "Calcium Channel $\alpha_2\delta_1$ Subunit Mediates Spinal Hyperexcitability in Pain Modulation" *Pain* 125(1-2):20-34, author manuscript.

Luo, Z.D. et al. (2008). "Never Induced Thrombosondins Contribute to Neuropathic Pain," Society for Neuroscience 2008, abstract only.

Luo, Z.D. et al. (Mar. 15, 2001). "Upregulation of Dorsal Root Ganglion $\alpha_2\delta$ Calcium Channel Subunit and Its Correlation with Allodynia in Spinal Nerve-Injured Rats," *J. Neurosci.* 21(2):1868-1875.

Marais, E. et al. (2001). "Calcium Channel $\alpha_2\delta$ Subunits-Structure and Gabapentin Binding," *Mol. Pharmacol.* 59(5):1243-1248.

McCarthy, K.D. et al. (Jun. 1980). "Preparation of Separate Astroglial and Oligodendroclial Cell Cultures from Rat Cerebral Tissue," *J. Cell Biol.* 85:890.

Meyer-Franke, A. et al. (Oct. 1995). "Characterization of the Signaling Interactions That Promote the Survival and Growth of Developing Retinal Ganglion Cells in Culture," *Neuron* 15:805-819.

Miao, W-M. et al. (Nov. 1, 2001). "Thrombospondin-1 Type 1 Repeat Recombinant Proteins Inhibit Tumor Growth Through Transforming Growth Facor-$\beta$-Dependent and-Independent Mechanisms," *Cancer Research* 61:7830-7839.

Miyazaki, T. et al. (2003). "Subtype Sqitiching of Vesicular Glutamate Transporters at Parallel Fibre-Purkinje Cell Synapses in Developing Mouse Cerebellum," *The Eur. J. Neuroscience* 17:2563-2572.

Mosher, D.F. et al. (2002). "Expression of Recombinant Matrix Components Using Baculoviruses," Chapter 3 in *Methods in Cell Biology,* Elsevier Science, 69:69-81.

Nestler, H.P. et al. (1994). "A General Method for Molecular Tagging of Encoded Combinatorial Chemistry Libraries," *J. Org. Chem.* 59(17):4723-4724.

Ohlmeyer, M.H.J. et al. (Dec. 1993). "Complex Synthetic Chemical Libraries Indexed with Molecular Tags," *Proc. Natl. Acad. Sci. USA* 90:10922-10926.

Palmer, T.D. et al. (May 3, 2001). "Progenitor Cells from human Brain After Death," *Nature* 411:42-43.

Palmer, T.D. et al. (1997). "The Adult Rat Hippocampus Contains Primordial Neural Stem Cells," *Mol. Cell. Neurosci.* 8:389-404.

Qabar, A.N. et al. (Jan. 14, 1994). "Thrombospondin 3 Is a Developmentally Regulated Heparin Binding Protein," *J. Biol. Chem.* 269(2):1262-1269.

Saumet, A. et al. (Jul. 15, 2005). "Type 3 Repeat/c-terminal Domain of Thrombospondin-1 triggers Caspase-Independent Cell Death Through CD47/$\alpha v\beta 3$ in Promyelocytic Leukemina NB4 Cells,"*Blood* 106(2):658-667.

Schleitoff, L. et al. (Oct. 15, 1999). "Genomic Structure and Functional Expression of a Human $\alpha_2/\delta$ Calcium Channel Subunit Gene (*CACNA2*),"*Genomics* 61(2):201-209.

Shihabuddin, L.S. (Nov. 1999). "The Search for Neural Progenitor Cells: Prospects for the Therapy of Neurodegenerative Disease," *Mol. Med. Today.* 5:474-480.

Skera, A. (Jul./Aug. 2000). "Engineered Protein Scaffolds for Molecular Recognition," *J. Mol. Recognit.* 13(4):167-187.

Skerra, A. (2007, e-pub. Jul. 20, 2007). "Alternative Non-Antibody Scaffold for Molecular Recognition," *Current Opinion in Biotechnology* 18:295-304.

Suman-Chauhan, N. et al. (Feb. 15, 1993). "Characterization of [$^3$H]gabapentin Binding to a Novel site in Rat Brain: Homogenate Binding Sites," *Eur. J. Pharmacol.* 244(3):293-301.

Sun, Y. et al. (1998). "CombiDOCK: Structure-Based Combinatorial Docking and Library Design," *J. Comput. Aided Mol. Des.* 12:597-604.

Susman, M.W. et al. (Nov. 6, 2007). "Identification of the Thrimbospondin Receptor that Promotes CNS Synaptoenesis," *OASIS—Online Abstract Submission and Invitation System,* located at <www.abstractonline.com/viewer/ViewAbstractPrintFriendly. asp?MKey={9603D605...>, last visited on Aug. 4, 2008, 1 page.

Svedsen, C.N. et al. (1997). "Long-Term Survival of Human Central Nervous System Progenitor Cells Transplanted into a Rat Model of Parkinson's Disease," *Exp. Neurol.* 48(1):135-146.

Tooney, P.A. et al. (1998). "Restricted Localization of Thrombospondin-2 Protein During Mouse Emryogenesis: A Comparison to Thrombospondin-1," *Matrix Biol.* 17:131-143.

Ullian, E.M. et al. (Jan. 26, 2001). "Control of Synapse Number by Glia," *Science* 291:657-661.

Van Der Loos, H. et al. (Jan. 26, 1973). "Somatosensory Cortex: Structural Alterations Following Early Injury to Sense Organs," *Science* 179:395-398.

Wahlestedt, C. et al. (May 20, 1993). "Antisense Oligodeoxynucleotides to NMDA-R1 Receptor Channel Protect Cortical Neurons From Excitoxicity and Reduce Focal Ischaemic Infarctions," *Nature* 363:260-263.

Wang, M. et al. (1999). "Structural Requirement of the Calcium-channel Subunit $\alpha_2\delta$ for Gabapentin Binding," *Biochem. J.* 342:313-320.

Whittaker, C.A. et al. (Oct. 2002). "Distribution and Evolution of von Willebrand/Inegrin A Domains: Widely Dispersed Domains with Roles in Cell Adhesion and Elsewhere," *Mol. Bio. of the Cell* 13:3369-3387.

Woolf, C.J. (Mar. 16, 2004). "Pain: Moving From Symptom Control Toward Mechanism-Specific Pharmacologic Management," *Annals of Internal Medicine* 140(6):441-451.

Xiong, Y. et al. (Mar. 2009). "Emerging Treatments for Traumatic Brain Injury," Expert Opin Emerg Drugs. Mar. 2009; 14(1): 67-84.

Zheng, W. et al. (1998). "Focus-2D: A New Approach To the Design of Targeted Combinatorial Chemical Libraries," *Pac. Symp. Biocompat.* 12 pages.

Figure 2
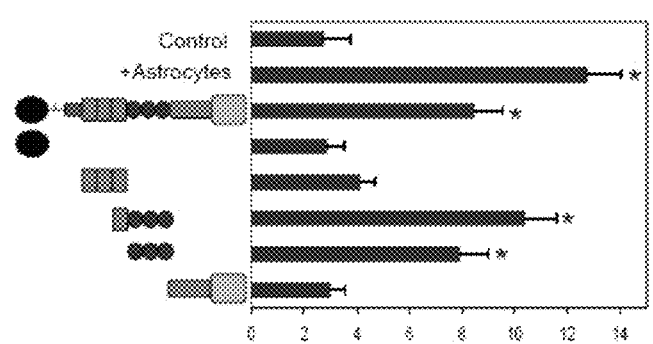
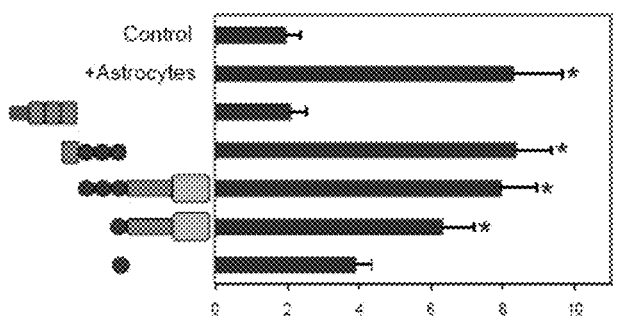
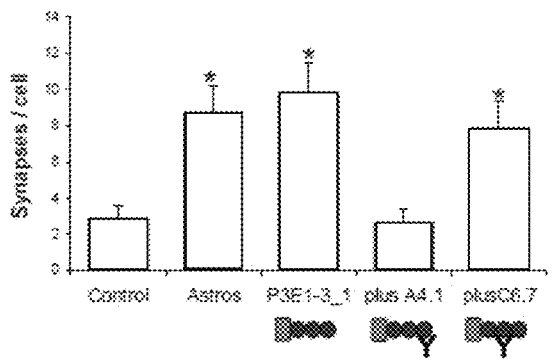
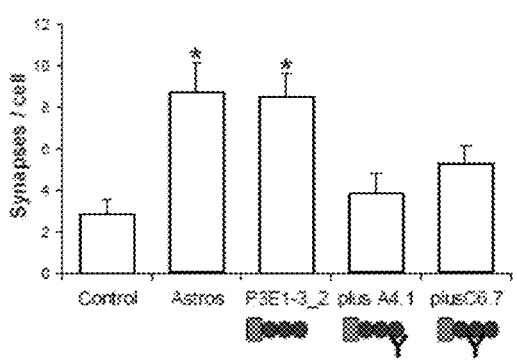

Figure 13
A
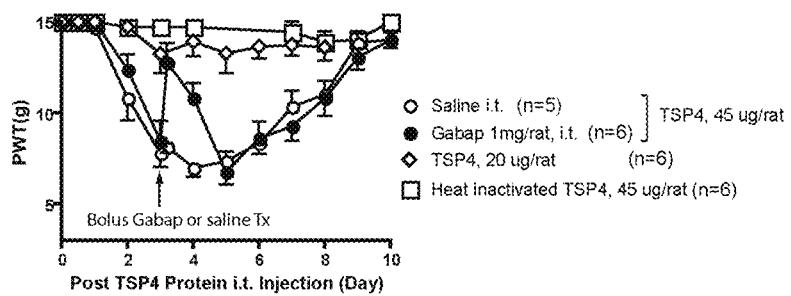
B
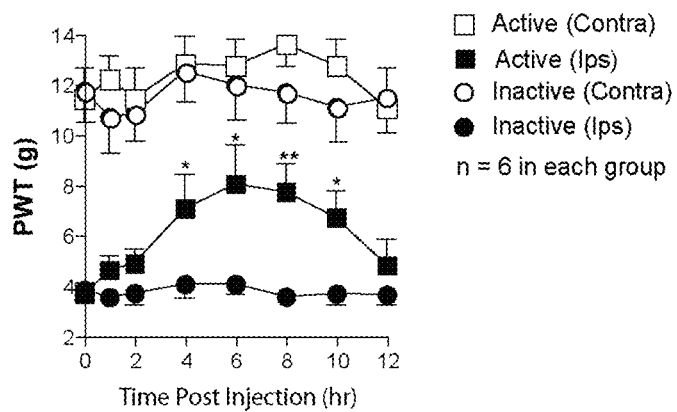
C
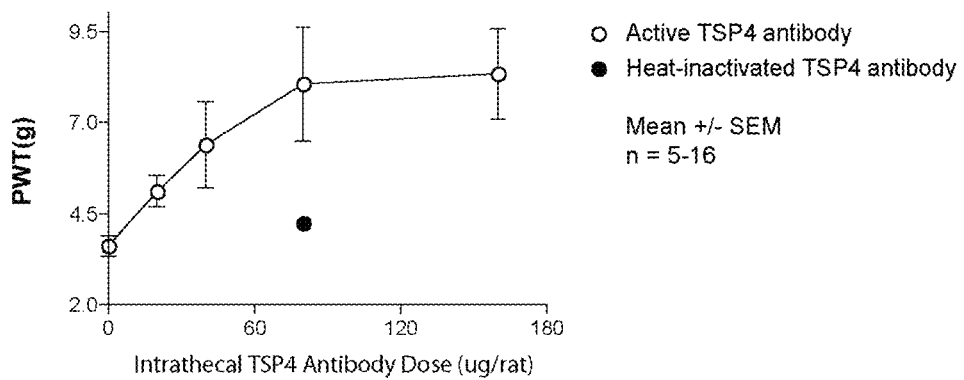

Figure 13
D
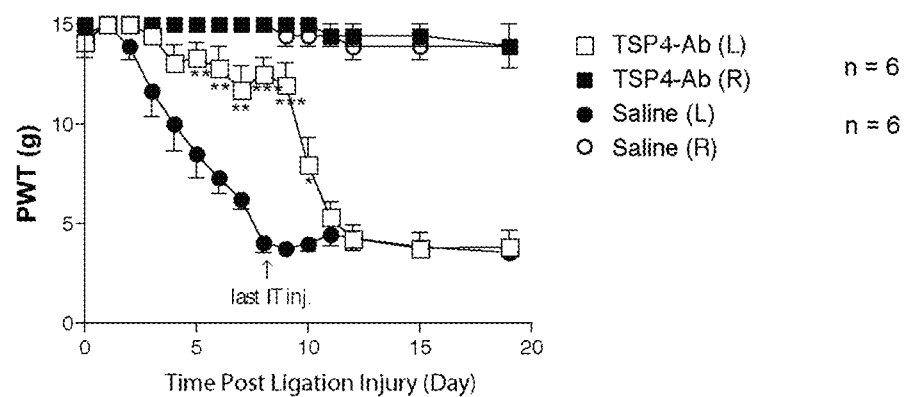
E
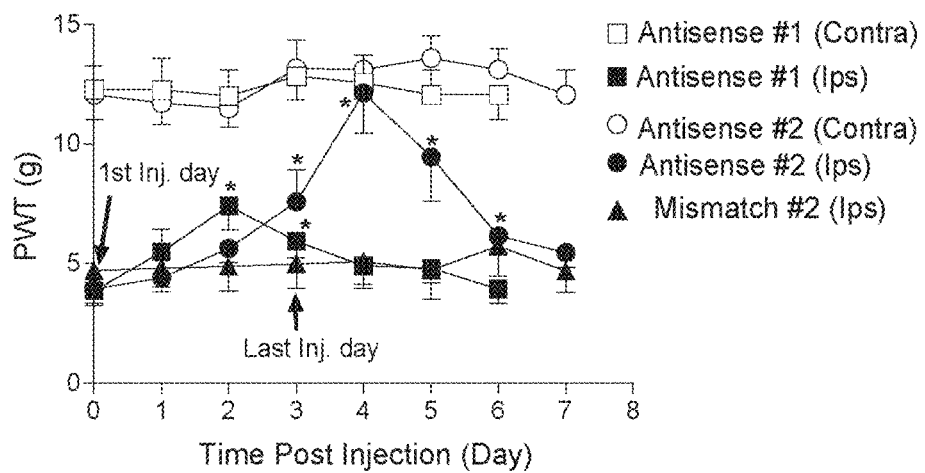

US 8,491,897 B2

TREATMENT OF NEUROPATHIC PAIN USING ANTI-THROMBOSPONDIN ANTIBODIES

RELATED APPLICATIONS

This application is a continuation application of U.S. patent application Ser. No. 12/191,884, filed Aug. 14, 2008, which claims priority benefit of U.S. Provisional Application Nos. 60/966,073, filed Aug. 23, 2007 and 61/052,551, filed May 12, 2008. All of these applications are hereby incorporated by reference in their entirety.

FEDERALLY-SPONSORED RESEARCH OR DEVELOPMENT

This invention was made with Government support under contract DA015043 awarded by the National Institutes of Health. The Government has certain rights in this invention

TECHNICAL FIELD

The present invention relates generally to compositions and methods for modulating synaptogenesis and axon and dendritic growth. Specifically, the invention includes use of agents that modulate interactions between a thrombospondin and an alpha 2 delta subunit of a calcium channel.

BACKGROUND OF THE INVENTION

Synapses are specialized cell adhesions that are the fundamental functional units of the nervous system, and they are generated during development with amazing precision and fidelity. During synaptogenesis, synapses form, mature, and stabilize and are also eliminated by a process that requires intimate communication between pre- and postsynaptic partners. In addition, there may be environmental determinants that help to control the timing, location, and number of synapses.

Synapses occur between neuron and neuron and, in the periphery, between neuron and effector cell, e.g. muscle. Functional contact between two neurons may occur between axon and cell body, axon and dendrite, cell body and cell body, or dendrite and dendrite. It is this functional contact that allows neurotransmission. Many neurologic and psychiatric diseases are caused by pathologic overactivity or underactivity of neurotransmission; and many drugs can modify neurotransmission, for examples hallucinogens, antipsychotics, anti-schizophrenia, tranquilizers, sedatives, anesthetics, pain drugs, Alzheimer's disease drugs, and Parkinson's disease drugs.

During recent years, a great deal of effort has been made by investigators to characterize the function of synaptic proteins, which include synaptotagmin, syntexin, synaptophysin, synaptobrevin, and the synapsins. These proteins are involved in specific aspects of synaptic function, e.g. synaptic vesicle recycling or docking, and in the organization of axonogenesis, differentiation of presynaptic terminals, and in the formation and maintenance of synaptic connections. See, for example, U.S. Patent Application Publication No. 2006/0019880.

Only by establishing synaptic connections can nerve cells organize into networks and acquire information processing capability such as learning and memory. Synapses are progressively reduced in number during normal aging, and are severely disrupted during neurodegenerative diseases. Therefore, finding molecules capable of creating and/or maintaining synaptic connections is an important step in the treatment of neurodegenerative diseases. Conversely, excessive synapse formation may be associated with stroke and psychiatric disorders. The modulation of synapse formation is of great interest for the treatment of a variety of nervous system disorders.

US 2006/0019880 discloses that thrombospondins can trigger synapse formation and a thrombospondin agonist or an antagonist can be used to promote or inhibit synaptogenesis in a patient in need of synaptogenesis promotion or inhibition.

All references, publications, and patent applications disclosed herein are hereby incorporated by reference in their entirety.

SUMMARY OF THE INVENTION

The present invention provides methods for promoting synaptogenesis in an individual comprising administering to the individual in need of synaptogenesis an effective dose of a polypeptide comprising at least one thrombospondin EGF-like domain, wherein the polypeptide is not a thrombospondin, and wherein synapse formation in the individual is increased. In some embodiments, the polypeptide binds and/or activates a calcium channel subunit selected from the group consisting of $\alpha 2\delta 1$, $\alpha 2\delta 2$, $\alpha 2\delta 3$, and $\alpha 2\delta 4$.

In some embodiments, the thrombospondin EGF-like domain is a polypeptide derived from a thrombospondin isotype of from about 35 to about 65 amino acids in length, comprising at least 6 cysteine amino acids, where the main structure is a two-stranded beta-sheet followed by a loop to a C-terminal short two-stranded sheet. In some embodiments, the thrombospondin EGF-like domain has at least 95% sequence identity to human TSP1, amino acids 551-586, 588-636, or 650-689, human TSP2 amino acids 553-588, 590-635, or 652-691, human TSP3 amino acids 316-368, 370-412, or 418-455, human TSP4 amino acids 290-324, 326-377, 379-418 or 424-461, or human cartilage oligomeric matrix amino acids 87-126, 127-179, 180-222, or 225-267. In some embodiments, the polypeptide comprises at least two thrombospondin EGF-like domains. In some embodiments, the polypeptide comprises at least three thrombospondin EGF-like domains. In some embodiments, the polypeptide lacks thrombospondin sequences other than the EGF-like domains. In some embodiments, the individual has suffered synapse loss as a result of senescence. In some embodiments, the individual has suffered synapse loss as a result of Alzheimer's disease, Parkinson's disease, ALS, multiple sclerosis, spinal cord injury, enteric nervous system disorders or glaucoma. In some embodiments, the individual has suffered a macular degeneration, a hearing loss, a diabetic neuropathy, or a chemotherapy induced neuropathy. In some embodiments, the individual has suffered synapse loss as a result of a psychiatric disorder selected from the group consisting of depression, schizophrenia, autism, and aggression. In some embodiments, synapse formation is at a neuromuscular junction. In some embodiments, synapse formation is at a muscle.

The invention also provides methods for treating a disorder caused by the presence of excess, hyperactive, abnormally connected or dysfunctional synapses comprising administering to an individual an effective amount of a thrombospondin antagonist agent which inhibits synaptogenesis activity of a thrombospondin. In some embodiments, the agent binds to a thrombospondin and blocks the interaction between the thrombospondin and one or more calcium channel subunits selected from the group consisting of $\alpha 2\delta 1$, $\alpha 2\delta 2$, $\alpha 2\delta 3$, and $\alpha 2\delta 4$.

The invention also provides methods for treating or preventing pain in an individual comprising administering to the individual an effective amount of a thrombospondin antagonist agent which inhibits an activity of a thrombospondin.

In some embodiments, the thrombospondin antagonist agent binds to a thrombospondin and blocks the interaction between the thrombospondin and one or more calcium channel subunits selected from the group consisting of α2δ1, α2δ2, α2δ3, and α2δ4. In some embodiments, the agent is an antibody that specifically binds to the thrombospondin. In some embodiments, the agent is an antibody that specifically binds to an EGF-like domain of the thrombospondin. In some embodiments, the agent is an antibody that specifically binds to the third EGF-like domain of the thrombospondin. In some embodiments, the thrombospondin is TSP1, TSP2, TSP3, TSP4, or cartilage oligomeric matrix. In some embodiments, the antibody specifically binds to TSP1, TSP2, TSP3, TSP4, or cartilage oligomeric matrix. In some embodiments, the antibody specifically binds to more than one members of thrombospondin. In some embodiments, the agent is a protein scaffold for an antibody mimic or a scaffold-derived binding protein.

In some embodiments, the agent is a polypeptide comprises an extracellular portion of a calcium channel subunit selected from the group consisting of α2δ1, α2δ2, α2δ3, and α2δ4, wherein polypeptide binds to a thrombospondin and blocks the interaction between the thrombospondin and the calcium channel subunit. In some embodiments, the agent is a polypeptide comprising the α2 portion of the calcium channel subunit α2δ1. In some embodiments, the polypeptide comprises the amino acids of about 253 to about 430 of human α2δ1 (VWFA domain). In some embodiments, the agent is a polypeptide comprising the α2 portion of the calcium channel subunit human α2δ2. In some embodiments, the polypeptide comprises the amino acids of about 291 to about 469 of human α2δ2 (VWFA domain). In some embodiments, the agent is a polypeptide comprising the α2 portion of the calcium channel subunit α2δ3. In some embodiments, the polypeptide comprises the amino acids of about 256 to about 438 of human α2δ3 (VWFA domain). In some embodiments, the agent is a polypeptide comprising the α2 portion of the calcium channel subunit α2δ4. In some embodiments, the polypeptide comprises the amino acids of about 291 to about 472 of human α2δ4. In some embodiments, the polypeptide comprises the amino acids of about 291 to about 473 of human α2δ4 (VWFA domain). In some embodiments of any of the method claims, the polypeptide is an immunoadhesin.

In some embodiments, the agent is an siRNA, an antisense RNA, or a microRNA that specifically inhibits expression of the thrombospondin. In some embodiments, the expression of TSP1, TSP2, TSP4, or cartilage oligomeric matrix is inhibited.

The invention further provides methods for treating or preventing pain in an individual comprising administering to an individual an effective amount of an antibody that specifically binds to a VWFA domain of a calcium channel subunit selected from the group consisting of α2δ1, α2δ2, α2δ3, and α2δ4, and blocks the interaction between a thrombospondin and said calcium channel subunit. In some embodiments, the antibody specifically binds to a VWFA domain of the calcium channel subunit selected from the group consisting of α2δ1, α2δ2, α2δ3, and α2δ4.

In some embodiments, the antibody binds to a region comprising from about amino acids 253 to about 430 of human α2δ1 (VWFA domain). In some embodiments, the antibody binds to a region comprising from about amino acids 291 to about 469 of human α2δ2 (VWFA domain). In some embodiments, the antibody binds to a region comprising from about amino acids 256 to about 438 of human α2δ3 (VWFA domain). In some embodiments, the antibody binds to a region comprising from about amino acids 291 to about 473 of human α2δ4 (VWFA domain).

Different type of pains can be treated by the methods described herein. The types of pain include, but are not limited to, somatic pain; pain associated with ligaments, tendons, bones, blood vessels, fasciae, or muscles; visceral pain; any pain caused by injury to the nervous system, chemotherapy, radiation, surgery, tumor compressing, or accident; cancer pain; inflammatory pain; post operative pain; migraine pain; phantom pain; allodynia; or hyperalgesia. In some embodiments, the pain can be either acute or chronic.

The invention also provides methods for treating epilepsy in an individual comprising administering to the individual an effective amount of an antibody that specifically binds to a VWFA domain of a calcium channel subunit selected from the group consisting of α2δ1, α2δ2, α2δ3, and α2δ4, and blocks the interaction between a thrombospondin and said calcium channel subunit. In some embodiments, the antibody specifically binds to a VWFA domain of the calcium channel subunit selected from the group consisting of α2δ1, α2δ2, α2δ3, and α2δ4.

The invention provides methods for promoting axonal growth in an individual comprising administering to an individual in need thereof an effective amount of a thrombospondin antagonist agent. In some embodiments, the individual has suffered a spinal cord injury. In some embodiments, the individual has suffered axonal or dendritic degeneration as a result of Alzheimer's disease, Parkinson's disease, ALS, or multiple sclerosis. In some embodiments, the individual has suffered a macular degeneration, a hearing loss, a diabetic neuropathy, cancer-induced neuropathy, radiation-induced neuropathy, or a chemotherapy-induced neuropathy. In some embodiments, the individual has suffered axonal or dendritic degeneration as a result of a psychiatric disorder selected from the group consisting of depression, schizophrenia, autism, anxiety, and aggression. Any thrombospondin agent described herein may be administered.

The invention also provides methods for treating a disorder characterized by excess of calcium influx in an individual, comprising administering to the individual an effective amount of an agent that blocks the interaction between a thrombospondin and a calcium subunit selected from the group consisting of α2δ1, α2δ2, α2δ3, and α2δ4. In some embodiments, the disorder is selected from the group consisting of muscle spasm, migraine, stroke, Alzheimer's disease, and Parkinson's disease. In some embodiments, the agent specifically binds to the thrombospondin.

The invention further provides methods for screening a candidate agent for activity in enhancing synaptogenesis, the method comprising: a) measuring binding of a candidate agent to an α2δ1, α2δ2, α2δ3, or α2δ4 polypeptide or a thrombospondin EGF-like domain; b) quantitating formation of synapses in a neural cell culture in the presence of the candidate agent if the candidate agent binds to the α2δ polypeptide or the thrombospondin EGF-like domain in step a), wherein an increased formation of synapses in the presence the candidate agent as compared to the formation of synapses in the absence of the candidate agent indicates that the candidate agent has the activity in enhancing synaptogenesis.

The invention also provides methods for screening a candidate agent for activity in inhibiting synaptogenesis, the method comprising: a) measuring binding of a candidate agent to an α2δ1, α2δ2, α2δ3, or α2δ4 polypeptide or a thrombospondin EGF-like domain; b) quantitating formation of synapses in a neural cell culture in the presence of the candidate agent and a thrombospondin agonist if the candidate agent binds to the α2δ polypeptide or the thrombospondin EGF-like domain in step a), wherein a decreased formation of synapses in the presence the candidate agent as compared formation of synapses in the absence of the candidate agent indicates that the candidate agent has the activity in inhibiting synaptogenesis.

It is to be understood that one, some, or all of the properties of the various embodiments described herein may be combined to form other embodiments of the present invention.

BRIEF DESCRIPTION OF THE DRAWINGS

FIG. 2A: The EGF-like domains mediate thrombospondin's synaptogenic effect. The domain structure of TSP1 and 2. TSPs 1 and 2 contain a heparin binding N-terminal domain (N), followed by an oligomerization domain and a procollagen repeat (PC), three properdin-like (TSP type 1), three EGF-like (TSP type 2), and thirteen calcium binding (TSP type 3) repeats and a C-terminal L-type lectin like globular domain (C).

FIG. 2B: The EGF-like domains mediate thrombospondin's synaptogenic effect. Quantification of the effect of purified TSP1 truncation constructs on synapse number. RGCs were treated with astrocytes, full-length TSP1 or a panel of TSP1 truncation constructs (8 nM each). The constructs that contained the EGF-like repeats of TSP1 were synaptogenic.

FIG. 2C: The EGF-like domains mediate thrombospondin's synaptogenic effect. Quantification of the effect of TSP2 truncation constructs on synapse number. Similar to TSP1 constructs the TSP2 fragments that contained the EGF-like repeats were also synaptogenic. A construct that contained the third EGF-like domain attached to the C-terminal region of the protein still retained most of its synaptogenic activity, however the third EGF-like domain alone did not increase the number of synapses significantly.

FIGS. 2D-E: The EGF-like domains mediate thrombospondin's synaptogenic effect. Antibodies against EGF like repeats of TSPs can block their synaptogenic effect. RGCs cultured with astrocytes or with the recombinant TSP1 (FIG. 2D) or TSP2 (FIG. 2E) truncation constructs that contained the third properdin repeats with the three EGF-like domains formed many more synapses when compared to RGCs cultured alone.

FIG. 13A: Intrathecal injection of TSP4 proteins into naive rats induced behavioral hypersensitivity in a dose-dependent and reversible manner. The onset time of the TSP protein effects was 2 days post injection, and the peak effects occurred 2-4 days post injection. Gabapentin or saline bolus treatment injection started three days after the TSP4 bolus injection (45 µg/rat), followed by behavioral test 1 hr after the treatment injection, and further followed by daily behavioral test. Intrathecal bolus gabapentin, but not saline, blocked the pain-inducing effects of TSP4. The gabapentin effects lasted for 1-2 days. PWT means paw withdrawal thresholds to von Frey filament stimulation.

FIG. 13B-C: Intrathecal injection of active TSP4 antibody reversed tactile allodynia in spinal nerve ligated rats in a dose-dependent manner. Bolus intrathecal TSP4 antibody at 80 µg/rat or at various doses were injected into two-week L5/6 spinal nerve ligated rats, followed by von Frey test (FIG. 13B-C). The bolus active TSP4 antibody reversed established allodynia at the injury site. In FIGS. 13B and C, "PWT" refers to paw withdrawal thresholds to von Frey filament stimulation; "Active" refers to active antibody; "Inactive" refers to antibody boind for 10 min.; "Contra" refers to non-injury side; "Ips" refers to injury side; error bars mean±SEM; and "*" indicates p<0.05 and "**" indicates p<0.01 as compared to pre-treatment level.

FIG. 13D: Pre-emptive intrathecal injection of TSP4 antisera prevented the development of tactile allodynia in spinal nerve ligated rats. Preemptive intrathecal daily treatment with TSP4 antibody (80 µg/rat/day) started prior to the ligation of the left L5/6 spinal nerve. The preemptive treatment with TSP4 antibody delayed the onset of injury-induced allodynia shown as reduced paw withdrawal thresholds (PWT) to mechanical stimulation. Data shown are the Mean±SEM. "L" refers to left (ligation) side; and "R" refers to right (non-injury) side. "*" indicates p<0.05 as compared to saline (L); "" indicates p<0.01 as compared to saline (L); and "*" indicates p<0.001 as compared to saline (L).

FIG. 13E: Intrathecal injection of TSP4 antisense oligodeoxynucleotides reversed tactile allodynia in the spinal nerve ligated rats in a sequence-specific and reversible manner. Two TSP4 antisense oligonucleotides (#1 and #2) were injected intrathecally (50 µg/rat/day) into spinal nerve ligated rats for 4 days 5 weeks after ligation injury. Daily intrathecal injection of TSP4 antisense oligonucleotide #2 caused a complete reversal of established allodynia in the injury side. Daily behavioral test was performed before injection blindly. Mean±SEM from n=6 in each group is shown. "Contra" refers to non-injury side; and "Ips" refers to L5/6 spinal nerve ligated side. "*" indicates p<0.05 as compared to pre-treatment levels.

DETAILED DESCRIPTION OF THE INVENTION

Figure 1:
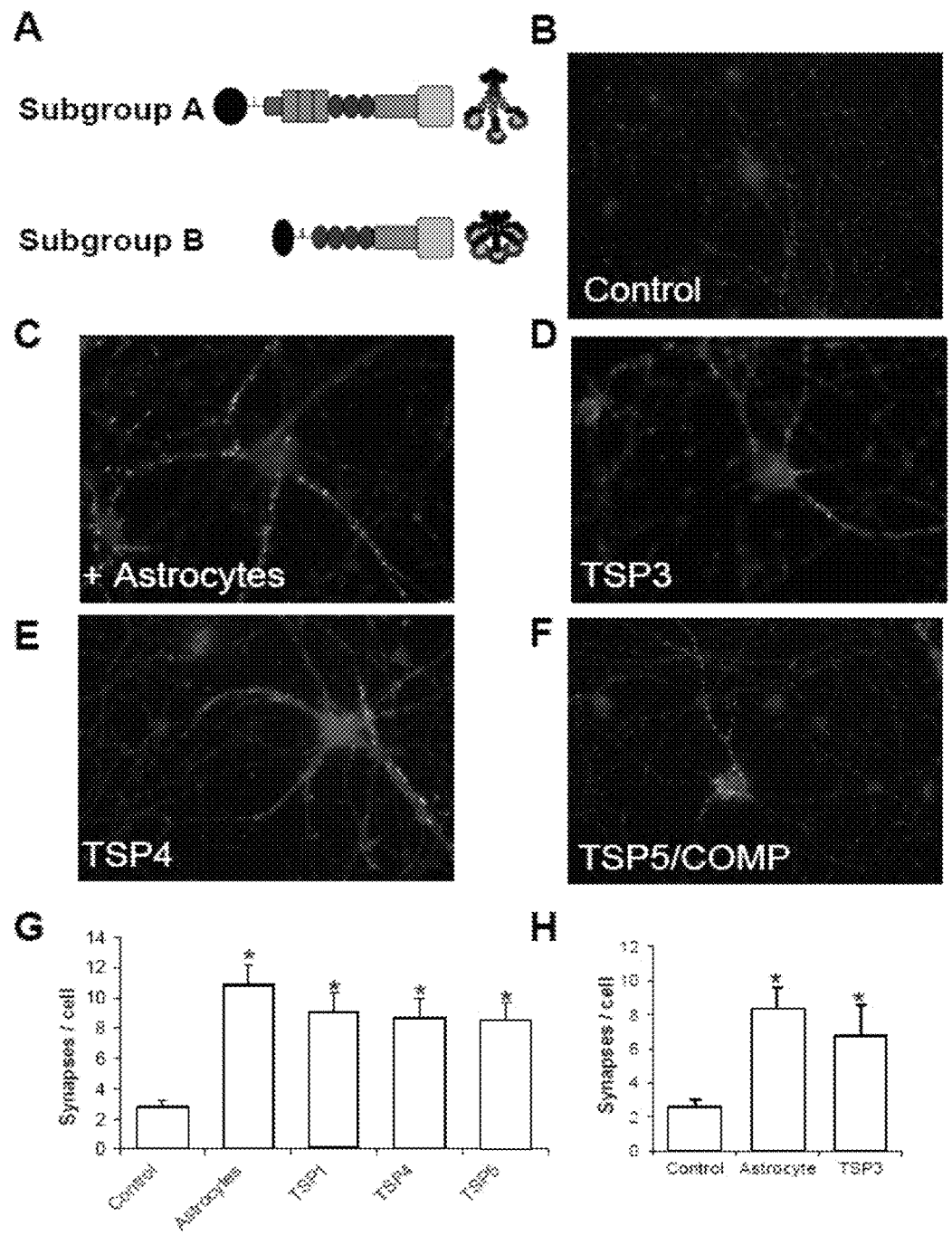
FIG. 1A: Pentameric Subgroup B Thrombospondins (TSPs) are Synaptogenic. TSPs are divided into two subgroups according to their domain structure and oligomerization state. Subgroup A TSPs (TSPs 1-2) are trimeric. Subgroup B TSPs (TSPs 3-5) are pentameric. The domain structure of subgroup B TSPs differ at the N-terminal part of the molecule. They possess a different N-terminal domain (black oval), and lack the procollagen (small square) and properdin-like repeats (rectangles), which are present in Subgroup A TSPs. Whereas all TSPs share a common domain structure at the C-terminal end composed of three EGF-like repeats (small ovals), thirteen calcium binding repeats (long rectangle), and a C-terminal L-lectin like globular domain (light-colored square).
FIGS. 1B-F: Pentameric Subgroup B Thrombospondins (TSPs) are Synaptogenic. Immunostaining of RGCs for co-localization of presynaptic synaptogamin and postsynaptic PSD-95 shows few synaptic puncta in the absence of astrocytes (B), but many in the presence of astrocyte feeding layers inserts (+Astrocyte) or TSPs 3, 4, and 5 mimic the synaptogenic effect of astrocytes or TSP1 and increase co-localized synaptic puncta.
FIG. 1G: Pentameric Subgroup B Thrombospondins (TSPs) are Synaptogenic. Quantification of the effects of astrocytes, purified TSP1, and purified recombinant TSPs 4 and 5 (8 nM each) on synapse number. TSPs 4 and 5 increased synaptic puncta numbers to the same extent as either astrocytes or TSP1, indicating the TSPs 4 and 5 are also synaptogenic.
FIG. 1H: Pentameric Subgroup B Thrombospondins (TSPs) are Synaptogenic. Quantification of the effects of astrocytes, and overexpressed TSP3 on number of synapses made by RGCs. TSP3 was overexpressed in Cos7 cells and RGCs were fed with this Cos7 cell culture supernatant. As a control condition, RGCs were fed with cell culture supernatant from Cos7 cells transfected with the empty vector. TSP3-containing culture supernatant increased the number of synaptic puncta to the same extent as astrocytes, indicating TSP3 is also synaptogenic

Methods and compositions are provided for protecting or treating an individual suffering from or preventing an individual from adverse effects of deficits in synaptogenesis, or from undesirably active synaptogenesis to a individual in need thereof. These findings have broad implications for a variety of clinical conditions, including traumatic brain injury, epilepsy, and other conditions where synapses fail to form or form inappropriately. Synaptogenesis is enhanced by contacting neurons with agents that are specific agonists of thrombospondins. Conversely, synaptogenesis is inhibited by contacting neurons with inhibitors or antagonists of thrombospondins.

Delivery of an exogenous thrombospondin or an agonist thereof induces new synapses in normal CNS, after CNS injury to promote repair, at neuromuscular junctions, e.g. at the junctions of spinal motor neurons and muscles. The ability to restore synaptogenesis in an adult has important implications for enhancing memory in normal brain; for treatment of Alzheimer's disease (a disease where synapses are lost), as well as promoting new synaptogenesis in repair and regeneration of injured CNS after stroke or spinal cord injury; enhancement of neuromuscular junctions in muscular dystrophy; amyotrophic lateral sclerosis (ALS); and the like. Delivery of an exogenous thrombospondin or an agonist thereof also find use in combination with administration of neural progenitors, or increases in neurogenesis, in order to promote functional connections between the nascent neurons and other neurons and effector cells.

Thrombospondin antagonists are useful in treating diseases of excess, unwanted synapses. The adult brain may upregulate thrombospondin after injury in "reactive astrocytes", which form glial scars. Glial scars are associated with epileptic loci, and may induce the unwanted excess synaptogenesis that underlies epilepsy. Similarly there are unwanted extra synapses that underlie the long-lived drug craving of addiction and/or pain.

Methods are provided for the modulation of synaptogenesis with soluble factors. It has been found that thrombospondin is sufficient to increase synapse formation on neurons, in particular synapse formation is increased by the action of the common EGF like domain shared by thrombospondins, including the third EGF-like domain. This domain interacts with a widely expressed transmembrane neuronal cell surface molecule, calcium channel subunit $\alpha 2\delta 1$. Agents that block the interaction between thrombospondin and $\alpha 2\delta 1$ are useful in inhibiting synapse formation, e.g. in the treatment of pain, epilepsy, anxiety, addiction, and to aid in the axon growth of regenerating neurons. It has been found that Gabapentin, which binds to $\alpha 2\delta 1$, and antibodies specific to the thrombospondin EGF-like domain, specifically inhibit synapse formation induced by thrombospondin. Methods of interest include the enhancement of synaptogenesis by contacting neurons with a thrombospondin EGF-like domain, or mimetic thereof such as agonistic antibodies, and the inhibition of synaptogenesis by blocking the interaction between thrombospondin EGF-like domain and a $\alpha 2\delta 1$, $\alpha 2\delta 2$, $\alpha 2\delta 3$, or $\alpha 2\delta 4$ polypeptide or protein.

In one embodiment of the invention, methods are provided for screening candidate agents for the ability to modulate synapse formation, including the inhibition of synapse formation. In one embodiment of the invention, the neurons are neurons in the central nervous system. In another embodiment, the neurons are peripheral nervous system neurons. Screening may include contacting a $\alpha 2\delta 1$, $\alpha 2\delta 2$, $\alpha 2\delta 3$, or $\alpha 2\delta 4$ polypeptide or protein, and determining the ability of an agent to bind to, or otherwise interact with $\alpha 2\delta 1$, $\alpha 2\delta 2$, $\alpha 2\delta 3$, or $\alpha 2\delta 4$. Such screening assays may further include determining the effect of a candidate agent on cells expressing $\alpha 2\delta 1$, $\alpha 2\delta 2$, $\alpha 2\delta 3$, or $\alpha 2\delta 4$. Such agents are candidate for therapeutic treatment of epilepsy and other conditions characterized by undesirable synaptogenesis.

Thrombospondin, agonists, and mimetics thereof, are administered to enhance synaptogenesis, particularly thrombospondin peptides comprising at least an EGF-like domain or agonistic antibodies that mimic the activity of the thrombospondin EGF-like domain. All 5 known thrombospondin isoforms have strong synapse inducing activity as a result of sharing the EGF-like domain. Inhibitors, e.g. antibodies, gabapentin and analogs thereof, etc. are administered to inhibit synaptogenesis.

The synaptogenic domain of TSP is useful in stimulating synapse formation in areas where synapses are lost due to neurodegenerative diseases, e.g. Alzheimer's disease, Parkinson's disease, ALS, multiple sclerosis, retinal degeneration, glaucoma, stroke, neuropathy aging, etc. In other embodiments, agent that block TSP mediated synapse formation, e.g. $\alpha 2\delta 1$ ligands such as gabapentin, pregabalin, etc.; antibodies specific for the EGF-like domain of TSP, etc. are useful in inhibiting synapse formation. Such methods find use in preventing aberrant synapse formation after injury to a regenerating axon, e.g. post injury to nerves including optic nerve, in glaucoma or spinal cord neurons following spinal cord injury, etc. The synaptogenesis modulators may be administered topically, e.g. to optic nerves or spinal cord.

DEFINITIONS

Synaptogenesis, as used herein, refers to the process by which pre- and/or post-synapses form on a neuron. Enhancing synaptogenesis results in an increased number of synapses, while inhibiting synaptogenesis results in a decrease in the number of synapses, or a lack of increase where an increase would otherwise occur. By "augmentation" or "modulation" of synaptogenesis as used herein, it is meant that the number of synapses formed is either enhanced or suppressed as required in the specific situation.

As used herein, the term "thrombospondin" may refer to any one of the family of proteins which includes thrombospondins I, II, III, IV, and cartilage oligomeric matrix protein. Reference may also be made to one or more of the specific thrombospondins. Thrombospondin is a homotrimeric protein composed of three identical subunits (TSP1 and TSP2) or homopentameric protein composed of five identical subunits (TSPs 3-5) glycoprotein with disulfide-linked subunits of MW 180,000. It contains binding sites for thrombin, fibrinogen, heparin, fibronectin, plasminogen, plasminogen activator, collagen, laminin, calcium etc. and also contains domain homologues to procollagen, properdin, and epidermal growth factor (EGF). It functions in many cell adhesion and migration events, including platelet aggregation.

As used herein, the term "modulator of synaptogenesis" refers to an agent that is able to alter synapse formation. Modulators include, but are not limited to, both "activators" and "inhibitors". An "activator" or "agonist" is a substance that enhances synaptogenesis. Conversely, an "inhibitor" or "antagonist" decreases the number of synapses. The reduction may be complete or partial. As used herein, modulators encompass thrombospondin antagonists and agonists.

As used herein, the term "modulator of axonal and/or dendritic growth" refers to an agent that is able to alter axonal and/or dendritic growth. Modulators include, but are not limited to, both "activators" and "inhibitors". An "activator" or "agonist" is a substance that enhances axonal and/or dendritic growth. Conversely, an "inhibitor" or "antagonist" decreases axonal and/or dendritic growth. The reduction may be complete or partial. As used herein, modulators encompass thrombospondin antagonists and agonists.

As used herein, "agent" refers to a biological, pharmaceutical, or chemical compound. Non-limiting examples include simple or complex organic or inorganic molecule, a peptide, a protein, an oligonucleotide, an antibody, an antibody derivative, antibody fragment, a vitamin derivative, a carbohydrate, a toxin, or a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like. A skilled artisan can readily recognize that there is no limit as to the structural nature of the agents of the present invention.

Agents that are employed in the methods of this invention can be randomly selected or rationally selected or designed. As used herein, in some embodiments, an agent is said to be randomly selected when the agent is chosen randomly without considering the specific sequences involved in the association of thrombospondin with a calcium channel (e.g., $\alpha 1 \delta 2$ calcium channel). An example of randomly selected agents is the use of a chemical library or a peptide combinatorial library.

Agonists and antagonists may include proteins (i.e., polypeptides), nucleic acids, carbohydrates, antibodies, or any other molecules that affects a protein and/or molecule of interest. In some embodiments, an antagonist may inhibit (e.g., decrease) one or more activities or functions of a protein and/or molecule of interest. In some embodiments, an agonist may stimulate (e.g., increase) one ore more activities or functions of a protein and/or molecule of interest. The term "analog" is used herein to refer to a molecule that structurally or functionally resembles a molecule of interest but which has been modified in a targeted and controlled manner, by replacing a specific substituent of the reference molecule with an alternate substituent. Compared to the starting molecule, an analog may exhibit the same, similar, or improved utility. Synthesis and screening of analogs, to identify variants of known compounds having improved traits (such as higher potency at a specific receptor type, or higher selectivity at a targeted receptor type and lower activity levels at other receptor types) is an approach that is well known in pharmaceutical chemistry.

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also fragments thereof (such as Fab, Fab', F(ab')$_2$, Fv), single chain (ScFv), mutants thereof, naturally occurring variants, fusion proteins comprising an antibody portion with an antigen recognition site of the required specificity, humanized antibodies, chimeric antibodies, and any other modified configuration of the immunoglobulin molecule that comprises an antigen recognition site of the required specificity.

The term "monoclonal antibody" encompasses not only intact monoclonal antibodies and full-length monoclonal antibodies, but also fragments thereof (such as Fab, Fab', F(ab')$_2$, Fv), single chain (ScFv), mutants thereof, fusion proteins comprising an antibody portion, humanized monoclonal antibodies, chimeric monoclonal antibodies, and any other modified configuration of the immunoglobulin molecule that comprises an antigen recognition site of the required specificity and the ability to bind to an antigen. It is not intended to be limited as regards to the source of the antibody or the manner in which it is made (e.g., by hybridoma, phage selection, recombinant expression, transgenic animals, etc.).

"Humanized" antibodies refer to a molecule having an antigen-binding site that is substantially derived from an immunoglobulin from a non-human species and the remaining immunoglobulin structure of the molecule based upon the structure and/or sequence of a human immunoglobulin. The antigen-binding site may comprise either complete variable domains fused onto constant domains or only the complementarity determining regions (CDRs) grafted onto appropriate framework regions in the variable domains. Antigen binding sites may be wild type or modified by one or more amino acid substitutions, e.g., modified to resemble human immunoglobulin more closely. Some forms of humanized antibodies preserve all CDR sequences (for example, a humanized mouse antibody which contains all six CDRs from the mouse antibodies). Other forms of humanized antibodies have one or more CDRs (one, two, three, four, five, six) which are altered with respect to the original antibody, which are also termed one or more CDRs "derived from" one or more CDRs.

"Chimeric antibodies" refers to those antibodies wherein one portion of each of the amino acid sequences of heavy and light chains is homologous to corresponding sequences in antibodies derived from a particular species or belonging to a particular class, while the remaining segment of the chains is homologous to corresponding sequences in another. Typically, in these chimeric antibodies, the variable region of both light and heavy chains mimics the variable regions of antibodies derived from one species of mammals, while the constant portions are homologous to the sequences in antibodies derived from another. One clear advantage to such chimeric forms is that, for example, the variable regions can conveniently be derived from presently known sources using readily available hybridomas or B cells from non human host organisms in combination with constant regions derived from, for example, human cell preparations. While the variable region has the advantage of ease of preparation, and the specificity is not affected by its source, the constant region being human, is less likely to elicit an immune response from a human subject when the antibodies are injected than would the constant region from a non-human source. However, the definition is not limited to this particular example.

As used herein, the term "immunoadhesin" designates antibody-like molecules which combine the binding specificity of a heterologous protein (an "adhesion") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM. The Ig fusions preferably include the substitution of a domain of a polypeptide or antibody described herein in the place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130 issued Jun. 27, 1995. In an embodiment, the invention provides an immunoadhesion comprising all or a part of the extracellular domain of a calcium channel (e.g., α2δ subunit or α2 subunit), or fragments thereof and a fusion partner, such as an antibody Fc domain.

A "variable region" of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al (1997) *J. Molec. Biol.* 273:927-948)). As used herein, a CDR may refer to CDRs defined by either approach or by a combination of both approaches.

A "constant region" of an antibody refers to the constant region of the antibody light chain or the constant region of the antibody heavy chain, either alone or in combination.

An antibody "specifically binds" or "preferentially binds" to a target if it binds with greater affinity, avidity, more readily, and/or with greater duration than it binds to other substances. For example, an antibody that specifically or preferentially binds to a thrombospondin and/or calcium channel epitope is an antibody that binds this thrombospondin and/or calcium channel epitope with greater affinity, avidity, more readily, and/or with greater duration than it binds to other thrombospondin and/or calcium channel epitopes or non-thrombospondin and/or non-calcium channel epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

As used herein, the term "labeled", with regard to the antibody, is intended to encompass direct labeling of the antibody by coupling (i.e., physically linking) a detectable substance, such as a radioactive agent or a fluorophore (e.g. fluorescein isothiocyanate (FITC) or phycoerythrin (PE)) to the antibody, as well as indirect labeling of the probe or antibody by reactivity with a detectable substance.

As used herein, "substantially pure" refers to material that is at least 50% pure (i.e., free from contaminants), more preferably at least 90% pure, more preferably at least 95% pure, more preferably at least 98% pure, more preferably at least 99% pure.

The terms "polypeptide", "oligopeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon an antibody, the polypeptides can occur as single chains or associated chains.

An "isolated" nucleic acid molecule encoding the antibodies herein is a nucleic acid molecule that is identified and separated from at least one contaminant nucleic acid molecule with which it is ordinarily associated in the environment in which it was produced. Preferably, the isolated nucleic acid is free of association with all components associated with the production environment. The isolated nucleic acid molecules encoding the polypeptides and antibodies herein is in a form other than in the form or setting in which it is found in nature. Isolated nucleic acid molecules therefore are distinguished from nucleic acid encoding the polypeptides and antibodies herein existing naturally in cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "epitope tagged" when used herein refers to a chimeric polypeptide comprising a polypeptide or antibody described herein fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

As used herein, "percent (%) amino acid sequence identity" and "homology" with respect to a peptide, polypeptide or antibody sequence refers to the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms needed to achieve maximal alignment over the full length of the sequences being compared.

As used herein, the term "RNA interference" or "RNAi" refers generally to a process in which a double-stranded RNA molecule or a short hairpin RNA molecule reducing or inhibiting the expression of a nucleic acid sequence with which the double-stranded or short hairpin RNA molecule shares substantial or total homology. The term "short interfering RNA" or "siRNA" or "RNAi agent" refers to an RNA sequence that elicits RNA interference. See Kreutzer et al., WO 00/44895; Zernicka-Goetz et al., WO 01/36646; Fire, WO 99/32619; Mello and Fire, WO 01/29058. As used herein, siRNA molecules include RNA molecules encompassing chemically modified nucleotides and non-nucleotides. The term "ddRNAi agent" refers to a DNA-directed RNAi agent that is transcribed from an exogenous vector. The terms "short hairpin RNA" or "shRNA" refer to an RNA structure having a duplex region and a loop region. In certain embodiments, ddRNAi agents are expressed initially as shRNAs.

"Carriers" as used herein include pharmaceutically acceptable carriers, excipients, or stabilizers that are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

"Pharmaceutically acceptable" buffers and salts include those derived from both acid and base addition salts of the above indicated acids and bases. Specific buffers and/or salts include histidine, succinate and acetate.

The term "pharmaceutical formulation" refers to a preparation that is in such form as to permit the biological activity of the active ingredient to be effective, and that contains no additional components that are unacceptably toxic to a subject to which the formulation would be administered. Such formulations are sterile.

By "neurological" or "cognitive" function as used herein, it is meant that the increase of synapses in the brain enhances the patient's ability to think, function, etc. In conditions where there is axon loss and regrowth, there may be recovery of motor and sensory abilities.

As used herein, the term "treatment" refers to clinical intervention designed to alter the natural course of the individual or cell being treated during the course of clinical pathology. Desirable effects of treatment include decreasing the rate of disease progression, ameliorating or palliating the disease state, and remission or improved prognosis. An individual is successfully "treated", for example, if one or more symptoms associated with the disease or condition are mitigated or eliminated.

As used herein, the term "prevention" includes providing prophylaxis with respect to occurrence or recurrence of a disease in an individual. An individual may be predisposed to the disease but has not yet been diagnosed with the disease.

An "effective amount" refers to at least an amount effective, at dosages and for periods of time necessary, to achieve the desired therapeutic or prophylactic result. An effective amount can be provided in one or more administrations.

A "therapeutically effective amount" is at least the minimum concentration required to effect a measurable improvement of a particular disorder. A therapeutically effective amount herein may vary according to factors such as the disease state, age, sex, and weight of the patient, and the ability of the antibody to elicit a desired response in the individual. A therapeutically effective amount is also one in which any toxic or detrimental effects are outweighed by the therapeutically beneficial effects.

A "prophylactically effective amount" refers to an amount effective, at the dosages and for periods of time necessary, to achieve the desired prophylactic result. Typically but not necessarily, since a prophylactic dose is used in subjects prior to or at an earlier stage of disease, a prophylactically effective amount may be less than a therapeutically effective amount.

"Chronic" administration refers to administration of the medicament(s) in a continuous as opposed to acute mode, so as to maintain the initial therapeutic effect (activity) for an extended period of time.

"Intermittent" administration refers to treatment that is not consecutively done without interruption, but rather is cyclic in nature.

As used herein, administration "in conjunction" includes simultaneous administration and/or administration at different times. Administration in conjunction also encompasses administration as a co-formulation or administration as separate compositions, including at different dosing frequencies or intervals, and using the same route of administration or different routes of administration.

An "individual" or "subject" refers a mammal, including humans, domestic and farm animals, and zoo, sport, or pet animals, such as chimpanzees and other apes and monkey species, dogs, horses, rabbits, cattle, pigs, goats, sheep, hamsters, guinea pigs, gerbils, mice, ferrets, rats, cats, and the like. Preferably, the individual is human. The term does not denote a particular age or gender.

The term "about" as used herein refers to the usual error range for the respective value readily known to the skilled person in this technical field. Reference to "about" a value or parameter herein includes (and describes) embodiments that are directed to that value or parameter per se.

As used herein the singular forms "a", "and", and "the" include plural referents unless the context clearly dictates otherwise.

It is understood that aspects and embodiments of the invention described herein include "consisting" and/or "consisting essentially of" aspects and embodiments.

Methods of Modulating Axon Growth and/or Synaptogenesis

The present invention provides methods for modulating axonal growth and/or synaptogenesis in an individual. The methods comprise administering an effective dose of an agent which modulates to a thrombospondin and/or an $\alpha 2\delta$ subunit of a calcium channel (e.g., an $\alpha 2\delta 1$, $\alpha 2\delta 2$, $\alpha 2\delta 3$, and $\alpha 2\delta 4$). In some embodiments, the agent binds to thrombospondin and/or an α2δ subunit of a calcium channel. In some embodiments, the agent is an agonist. In some embodiments, the agent is an antagonist.

Calcium Channel, Alpha-2/Delta Subunit

In some embodiments of any of the methods described herein, the calcium channel is a voltage-gated $Ca^{2+}$ ($Ca_v$) channels are composed of a pore-forming α1 subunit, associated, at least in the case of the $Ca_v1$ and 2 subfamilies, with an intracellular β subunit responsible for trafficking and a transmembrane $α_2δ$ (such as $α_2δ1$) subunit. The α1 subunit determines the main biophysical properties of the channel and is modulated by the other subunits.

The CACNA2D1 gene encodes the alpha-2/delta subunit of skeletal muscle and brain voltage-dependent calcium channels, which are heteromultimer complexes comprising 4 subunits: alpha-1, alpha-2/delta, beta-1, and gamma. Alternative names for this molecule include alpha2delta Subunit 1; Cacna2d1; Calcium channel alpha2delta-1; Calcium channel, voltage-dependent, alpha2/delta 1 subunit; Calcium channel, voltage-dependent, alpha2/delta subunit 1; Cch12a; and Voltage-dependent calcium channel alpha2delta-1. CACNA2D1 alters the properties of pore-forming alpha-1 subunits of voltage-gated calcium channels, and it is post-translationally processed into 2 peptides, an alpha-2 subunit and a delta subunit, that are held together by a disulfide bond. The alpha-2/delta protein is encoded by at least 4 different genes: CACNA2D1 ($α_2δ1$), CACNA2D2 ($α_2δ2$), CACNA2D3 ($α_2δ3$), and CACNA2D4 ($α_2δ4$) (see, for example Schleithoff et al., 1999 *Genomics* 61: 201-209; and Field et al. (2006) *Proc. Nat. Acad. Sci.* 103: 17537-17542, herein specifically incorporated by reference). The genetic sequences and protein sequences are publicly available. For example, genetic sequence for $α_2δ1$ is at Genbank, accession number BC117470; and protein sequence for $α_2δ1$ is at Genbank accession number AAI17471; protein sequence for $α_2δ2$ is at Genbank accession number AAI52439; protein sequence for $α_2δ3$ is at Genbank accession numbers AAI37506 and AAI37502; and protein sequence for $α_2δ4$ is at Genbank accession number AAI50187.

Iles et al. (1994) *Hum. Molec. Genet.* 3: 969-975 cloned and partially sequenced the CACNL2A gene. The CACNL2A is expressed in many tissues, including skeletal muscle, brain, heart, and lung. A comparison of sequences of cDNAs representing the skeletal muscle and brain isoforms showed that they are encoded by a single gene. The "delta" portion, encoded by exons 37 to 40, is post-transcriptionally cleaved from the C-terminal "alpha" portion of the protein. The membrane-spanning region of the delta portion is encoded by exon 40. The CACNA2D1 gene undergoes alternative splicing at exons 19 and 24, corresponding to muscle and brain isoforms, respectively.

The topology of the $α_2δ$ protein appears to generalize for all four $α_2δ$ subunits. They are all predicted to be type 1 transmembrane proteins, because all have a hydrophobic region in the C-terminus (CT) that is likely to be a transmembrane domain. α2δ is translated from a single gene product, which gets post-translationally cleaved into α2 and δ parts that remain associated via disulfide bridges. The α2 portion of the protein is entirely extracellular while the δ portion has a small extracellular part that is attached to α2, and a transmembrane domain with a very short cytoplasmic tail that tethers the whole molecule to the membrane (Davies et al., Trends in Pharmacol. Sci. 28:220-228, 2007). All have predicted N-terminal signal sequences, indicating that the N terminus is extracellular. One domain identified by sequence homology in the extracellular sequence of all $α_2δ$ subunits is the von Willebrand factor type A (VWFA) domain within the $α_2$ moiety. Canti et al., *Curr. Neuropharmacology* 1:209-217, 2003; Canti et al., *Proc. Natl. Acad. Sci. USA* 102:11230-11235, 2005; Arikkath et al., *Curr. Opin. Neurobiol.* 13:298-307, 2003. In human $α_2δ$ subunits, VWFA domain comprises amino acids from about 253 to about 430 of $α_2δ1$ (see worldwide web at expasy.org/uniprot/P54289), amino acids from about 291 to about 469 of $α_2δ2$ (see worldwide web at expasy.org/uniprot/Q9NY47), amino acids from about 256 to about 438 of $α_2δ3$ (see worldwide web at expasy.org/uniprot/Q8IZS8), and amino acids from about 291 to about 473 of $α_2δ4$ (see worldwide web at expasy.org/uniprot/Q7Z3S7). The amino acid positions are based on the unprocessed precursor protein with signal sequence.

All $α_2δ$ subunits enhance calcium currents through the high-voltage-activated (HVA) $Ca_v1$ and $Ca_v2$ channels. Voltage-activated $Ca^{2+}$ channels are important signaling proteins in many cellular processes including muscle contraction, secretion, synaptic function, and transcriptional regulation. Expression of the $α_2δ$-1 protein increases the targeting of the $α_1$ subunit to the membrane and enhances gating of the pore-forming subunit (as measured by gating charge). In general, the co-expression of the $α_2δ$-1 protein with the $α_1$ and β subunits of the high-voltage-gated calcium channels shifts the voltage dependence of activation and inactivation to more negative potentials and accelerates the rates of channel activation and inactivation.

In addition to these direct actions on calcium channel function, the $α_2δ$-1 protein mediates the actions of gabapentin and pregabalin, agents used in the treatment of neuropathic pain. In vitro studies have shown that this subunit is the binding site for gabapentin, an anticonvulsant that exerts antihyperalgesic effects. In vivo studies further demonstrated that point mutations in $α_2δ$-1 protein eliminated the therapeutic effect of gabapentin in a rodent model of neuropathic pain. Increased expression of this subunit in the spinal cord and dorsal root ganglia (DRG) has been suggested to play a role in enhanced nociceptive responses of spinal nerve-injured rats to innocuous mechanical stimulation (allodynia). Induction of the alpha2delta-1 subunit in the DRG and spinal cord is likely regulated by factors that are specific for individual neuropathies and may contribute to gabapentin-sensitive allodynia.

Gabapentin (1-(aminomethyl)cyclohexaneacetic acid) is considered by physicians to be the "gold standard" treatment for a variety of neuropathic pain. It is prescribed to over 50% of patients suffering from diabetic neuropathy or postherpetic neuralgia. The drug is well tolerated except for sedation seen at higher doses. Alternatively, the 3-substituted analogue of γ-aminobutyric acid (GABA), pregabalin, provides for similar activity with an improved pharmacokinetic profile. Compounds represented by gabapentin and pregabalin exert their effect of blocking neuropathic pain by binding to the $α_2δ1$ subunit of voltage-gated $Ca^{2+}$ channel (see Marais et al. (2001) *Mol. Pharmacol.* 59: 1243-1248 and Wang et al. (1999) *Biochem. J.* 342: 313-320). This interaction was though to result in inhibition of calcium influx into neuronal cells, thereby inhibiting neurotransmitter release and suppressing the development of central sensitization.

The medicinal chemistry of a number of $α_2δ1$ ligands has been explored, including structural variants in the β-amino acid and α-amino acid classes, non-amino acid leads and prodrugs. Binding of these ligands to the alpha2delta subunit is considered to explain their usefulness in treating several clinical disorders, including epilepsy, pain from diabetic neuropathy, postherpetic neuralgia and fibromyalgia, and generalized anxiety disorder.

Thrombospondin

In some embodiments of any of the methods described herein, "thrombospondin" may refer to any one of the family of proteins which includes thrombospondins I, II, III, IV, and cartilage oligomeric matrix protein. Reference may also be made to one or more of the specific thrombospondins. Thrombospondin is a homotrimeric (TSP1 and TSP2) or homopentameric (TSPs 3-5) glycoprotein with disulfide-linked subunits of MW 180,000. It contains binding sites for thrombin, fibrinogen, heparin, fibronectin, plasminogen, plasminogen activator, collagen, laminin, etc. It functions in many cell adhesion and migration events, including platelet aggregation.

Thrombospondin I (THBS1; also known as TSP1) has the Genbank accession number X04665 for the human DNA sequence and TSP1 human (P07996) for the human protein (see worldwide web at expasy.org/uniprot/P07996). It is a multimodular secreted protein that associates with the extracellular matrix and possesses a variety of biologic functions, including a potent angiogenic activity. Other thrombospondin genes include thrombospondins II (THBS2; 188061), III (THBS3; 188062), and IV (THBS4; 600715) with the corresponding protein sequences TSP1 Human (P07996), TSP2 Human (P35442); TSP3 Human (P49746), and TSP4 Human (P35443).

Human thrombospondin 2 (THBS2; also known as TSP2) has the Genbank accession number L12350 (see worldwide web at expasy.org/uniprot/P35442) for the human sequence. It is very similar in sequence to THBS 1.

Human thrombospondin 3 (THBS3; also known as TSP3) has the Genbank accession number L38969 for the human sequence (see worldwide web at expasy.org/uniprot/P49476). The protein is clearly homologous to THBS1 and THBS2 in its COOH-terminal domains but substantially different in its NH2-terminal region, suggesting functional properties for THBS3 that are unique, but also related to those of THBS1 and THBS2. The 956-amino acid predicted protein is highly acidic, especially in the third quarter of the sequence which corresponds to 7 type III calcium binding repeats. Four type II EGF-like repeats are also present.

The human THBS4 gene (also known as TSP4), Genbank accession number Z19585 for the human sequence (see worldwide web at expasy.org/uniprot/P35443), contains an RGD (arg-gly-asp) cell-binding sequence in the third type 3 repeat. It is a pentameric protein that binds to heparin and calcium.

Cartilage oligomeric matrix protein (also known as TSP5), Genbank accession L32137 (see worldwide web at expasy.org/uniprot/P49474), is a 524-kD protein that is expressed at high levels in the territorial matrix of chondrocytes. The sequences indicate that it is a member of the thrombospondin gene family.

Thrombospondin EGF-Like Domains

In some embodiments of any of the methods described herein, the method comprises administering at least one thrombospondin EGF-like domain. The known thrombospondin isoforms comprise a number of specific domains. For THBS1 and THBS2, these include a heparin-binding N terminal domain, a linker with homology to procollagen, three TSP-type-1 repeats, three EGF-like repeats, seven TSP type-3 calcium binding repeats, and a cell-binding carboxyl-terminal domain. As shown herein, for example in FIG. 2, the EGF-like domains are sufficient to induce synaptogenesis.

The EGF-like domains have a distinct motif sequence. A common feature is that these repeats are found in the extracellular domain of membrane-bound proteins or in proteins known to be secreted. The EGF domain includes six cysteine residues which have been shown to be involved in disulphide bonds. The main structure is a two-stranded beta-sheet followed by a loop to a C-terminal short two-stranded sheet. Subdomains between the conserved cysteines vary in length. The disulfide bonded structure exemplified by EGF and its precursor and TGF-α are encountered in many proteins, e.g. as described by Apella et al. (1988) FEBS Lett 231:1-4; and Engel (1989) FEBS Lett 25:1-7, each herein incorporated by reference. An alignment of the mouse TSP EGF-like domains may be found in Bornstein (1992) FASEB J 6:3290-3299, herein incorporated by reference. Each EGF-like domain is from about 35 to about 70 amino acids in length, more usually from around about 40 amino acids to around about 65 amino acids in length. The EGF repeat may include the hydroxylated amino acids, β-hydroxyaspartic acid and β-hydroxyasparagine. The repeats may also comprise negatively charged amino acids at positions 2, 4 and 5 of the domain.

Exemplary EGF-like domains are found in the human thrombospondin polypeptides. With reference to THBS1 sequence and the above referenced sequence, EGF-like domains are found at amino acids 551-586, 588-636 and 650-689. With reference to THBS2 sequence and the above referenced sequence, EGF-like domains are found at amino acids 553-588, 590-635, and 652-691. With reference to THBS3 sequence and the above referenced sequence, EGF-like domains are found at amino acids 316-368, 370-412, 418-455. With reference to THBS4 sequence and the above referenced sequence, EGF-like domains are found at amino acids 290-324, 326-377, 379-418 and 424-461.

As used herein, a thrombospondin EGF-like domain includes, without limitation, a polypeptide of from about 35 to about 65 amino acids in length, comprising at least 6 cysteine amino acids, where the main structure is a two-stranded beta-sheet followed by a loop to a C-terminal short two-stranded sheet. The domain may have at least about 95% sequence identity, at least about 98% sequence identity, at least about 99% sequence identity, 100% sequence identity to the above defined domains from human thrombospondin proteins. Peptides may be truncated by 1, 2, 3, 4, 5, or more amino acids from the amino terminus, the carboxy terminus, or both.

Agonists

The present invention provides methods for modulating axonal growth and/or synaptogenesis in an individual in need thereof comprising administering an effective dose of an agonist of a thrombospondin. In some embodiments, the invention provides methods for promoting synaptogenesis in an individual comprising administering to the individual in need of synaptogenesis an effective dose of an agonist. In some embodiments, the agonist is a thrombospondin agonist. Agonists may be tested for one or more agonist activity (e.g., binds and activates an α2δ subunit of a calcium channel) using methods known in the art and/or methods described herein.

In some embodiments of any of the methods, thrombospondin agonists include polypeptides, nucleic acids, carbohydrates, immunoadhesion, thrombospondin variants, peptidomimetics, and small molecules, anti-thrombospondin antibodies and immunoglobulin variants, amino acid variants of human thrombospondin including amino acid substitution, deletion, and addition variants, or any combination thereof, and chimeric immunoglobulins. The thrombospondin agonists of this invention may be based on the inventors' identification of the thrombospondin domains involved in the binding of thrombospondin to its native ligands, such as a calcium channel α2δ subunit. In some embodiments, thrombospondin agonists are antibodies. In some embodiments, the antibodies are monoclonal antibodies. In some embodiments, the monoclonal antibodies are chimeric antibodies or humanized antibodies. In some embodiments, the thrombospondin agonists are small molecules.

In some embodiments, thrombospondin agonists are polypeptides. In some embodiments, the polypeptide is a polypeptide comprising at least one thrombospondin EGF-like domain, wherein the polypeptide binds and activates a calcium channel subunit selected from the group consisting of α2δ1, α2δ2, α2δ3, and α2δ4, and wherein synapse formation in the individual is increased. In some embodiments, the polypeptide is not a thrombospondin. In some embodiments, the polypeptide is a thrombospondin.

In some embodiments, the polypeptide thrombospondin agonist includes an EGF-like domain. EGF-like domain polypeptides of interest may include 1, 2, 3 or more thrombospondin EGF-like domains, as defined above. In some embodiments, the EGF-like domain polypeptides may comprise or consist of one EGF-like domain. In some embodiments, the EGF-like domain polypeptides include at least two thrombospondin EGF-like domains. In some embodiments, the EGF-like domain polypeptides include at least three thrombospondin EGF-like domains. In some embodiments, the EGF-like domain polypeptides comprise the third EGF-like domain, calcium binding repeats and C-terminal region of a thrombospondin. In some embodiments, the EGF-like domain polypeptides lack thrombospondin sequences other than the EGF-like domains. In some embodiments, the EGF-like domain polypeptide may lack one or more of the thrombospondin laminin G domain, von Willebrand factor C type domain, thrombospondin type I domain, thrombospondin type 3 repeat, and/or thrombospondin C-terminal region. In some embodiments, the thrombospondin EGF-like domain is a polypeptide derived from a thrombospondin isotype of from about 35 to about 65 amino acids in length, comprising at least 6 cysteine amino acids, where the main structure is a two-stranded beta-sheet followed by a loop to a C-terminal short two-stranded sheet. In some embodiments, the thrombospondin EGF-like domain has at least 95% sequence identity to human THBS1, amino acids 551-586, 588-636, 650-689, human THBS2 amino acids 553-588, 590-635, 652-691, human THBS3 amino acids 316-368, 370-412, 418-455, human THBS4 amino acids 290-324, 326-377, 379-418 and 424-461.

The sequence of the thrombospondin EGF-like domains may be altered in various ways known in the art to generate targeted changes in sequence. The polypeptide will usually be substantially similar to the sequences provided herein, i.e. will differ by at least one amino acid, and may differ by at least two but not more than about ten amino acids. The sequence changes may be substitutions, insertions or deletions. Scanning mutations that systematically introduce alanine, or other residues, may be used to determine key amino acids. Conservative amino acid substitutions typically include substitutions within the following groups: (glycine, alanine); (valine, isoleucine, leucine); (aspartic acid, glutamic acid); (asparagine, glutamine); (serine, threonine); (lysine, arginine); or (phenylalanine, tyrosine).

Modifications of interest that do not alter primary sequence include chemical derivatization of polypeptides, e.g., acetylation, or carboxylation. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine.

Also included in the subject invention are polypeptides that have been modified using ordinary molecular biological techniques and synthetic chemistry so as to improve their resistance to proteolytic degradation or to optimize solubility properties or to render them more suitable as a therapeutic agent. For examples, the backbone of the peptide may be cyclized to enhance stability (see Friedler et al. (2000) *J. Biol. Chem.* 275:23783-23789). Analogs of such polypeptides include those containing residues other than naturally occurring L-amino acids, e.g. D-amino acids or non-naturally occurring synthetic amino acids. In some embodiments, thrombospondin polypeptides, including their immunogenic epitopes and other fragments, may be combined with heterologous molecules, resulting in therapeutically useful fusion molecules. It provides fusion partners capable of imparting favorable pharmacokinetics and/or pharmacodynamics to the thrombospondin. In an embodiment, the invention provides a fusion molecule comprising all or a part of the EGF-like domains of thrombospondin, or fragments thereof and a fusion partner, such as an antibody Fc domain. Fusion molecules of the invention may have an increased half-life in vivo, as compared to thrombospondin EGF-like domains.

The subject peptides may be prepared by in vitro synthesis, using conventional methods as known in the art. Various commercial synthetic apparatuses are available, for example, automated synthesizers by Applied Biosystems, Inc., Foster City, Calif., Beckman, etc. By using synthesizers, naturally occurring amino acids may be substituted with unnatural amino acids. The particular sequence and the manner of preparation will be determined by convenience, economics, purity required, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

The polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

Antagonists

The present invention provides methods for modulating axonal growth and/or synaptogenesis in an individual in need thereof comprising administering an effective dose of an antagonist (e.g., agent) of a thrombospondin and/or a calcium channel. In some embodiments, the methods inhibit synaptogenesis, decrease the number of synapses, or decrease the activity of synapses. In some embodiments, the methods promote axonal growth. In some embodiments, the methods promote dendritic growth. In some embodiments, the methods promote both axonal and dendritic growth. In some embodiments, the antagonist is a thrombospondin antagonist. In some embodiments, the thrombospondin antagonist inhibits one or more activities of a thrombospondin, for example, synaptogenesis activity. In some embodiments, the thrombospondin antagonist binds to a thrombospondin and blocks the interaction between a thrombospondin and an α2δ subunit of a calcium channel. In some embodiments, the antagonist is an antagonist to an α2δ subunit of a calcium channel. In some embodiments, the antagonist binds to an α2δ subunit of a calcium channel and blocks the interaction between a thrombospondin and the α2δ subunit of a calcium channel.

Further, the invention provides, in some embodiments, methods for treating pain (such as neuropathic pain, visceral pain, cancer pain, inflammatory pain, post operative pain, migraine pain, or phantom pain) in an individual comprising administering to an individual having pain an effective amount of an antagonist. In some embodiments, the pain includes, but is not limited to, somatic pain (e.g. cutaneous (body surface) or deep tissues (musculoskeletal tissues) pain); pain associated with ligaments, tendons, bones, blood vessels, fasciae, and muscles; visceral pain (e.g. thoracic (chest) pain, abdominal pain, or pelvic viscera pain, or neuropathic pain); any pain caused by injury to the nervous system, chemotherapy, radiation, surgery, tumor compressing, or accident; cancer pain (e.g., breakthrough cancer pain, pain from pancreatic cancer, or metastases in the abdomen or bone); inflammatory pain (e.g. pain associated with rheumatoid arthritis, psoriatic arthritis, Reiter's syndrome (reactive arthritis), ankylosing spondylitis, or inflammatory arthritic disorders); post operative pain; migraine pain; or phantom pain (e.g. amputation in quadriplegics). In some embodiments, the pain can be either acute or chronic, and comprises allodynia (i.e. pain due to a stimulus which does not normally provoke pain) or hyperalgesia (i.e. an increased response to a stimulus which is normally painful).

In some embodiments, the invention also provides methods for treating epilepsy in an individual comprising administering to the individual an effective amount of an antagonist. In some embodiments, the antagonist is a thrombospondin antagonist. In some embodiments, the antagonist is a α2δ subunit calcium channel antagonist. In some embodiments, the methods comprise administering to an individual in need thereof an effective amount of an antagonist (e.g., agent) that binds to a thrombospondin and blocks the interaction between the thrombospondin and one or more calcium channel subunits selected from the group consisting of α2δ1, α2δ2, α2δ3, and α2δ4.

Antagonists of synaptogenesis include agents that interfere with the interaction between thrombospondin and calcium channel subunit α2δ, which include, without limitation, antibodies specific for thrombospondin, particularly antibodies specific for at least one thrombospondin EGF-like domain, and α2δ ligands, including gabapentin and pregabalin and analogs thereof, e.g. as described in U.S. Pat. Nos. 6,518,289, 6,683,112, 4,087,544, published US Patent application 20050192353, etc., herein incorporated by reference. In some embodiments, the antagonists exclude gabapentin, pregabalin and/or analogs thereof.

In some embodiments of any of the methods, thrombospondin antagonists include polypeptides, nucleic acids (e.g., RNAs (e.g., siRNA, antisense RNA, or microRNA), and DNAs), carbohydrates, immunoadhesion, thrombospondin variants, thrombospondin peptide antagonists, peptidomimetics, small molecules, anti-thrombospondin antibodies and immunoglobulin variants, scaffold-derived binding proteins that binds to a thrombospondin. Scaffold-based proteins comprise single domains of antibodies, the immunoglobulin superfamily, protease inhibitors, helix-bundle proteins, disulphide-knotted peptides, protein A, lipocalins, fibronectin domains, ankyrin consensus repeat domains, thioredoxins, and high disulfide density scaffold proteins. See e.g., U.S. Pat. No. 6,818,418, Lipovsek et al.; Skerra (2000) *J Mol Recognit*. 13(4):167-87; Skerra (2007) *Current Opinion in Biotechnology*, 18: 295-304; worldwide web at.amunix.com/Technology.html. Amino acid variants of human thrombospondin include amino acid substitution, deletion, and addition variants, or any combination thereof, and chimeric immunoglobulins. The thrombospondin antagonists of this invention may be based on the inventors' identification of the thrombospondin domains involved in the binding of thrombospondin to a calcium channel α2δ subunit. In some embodiments, thrombospondin antagonists are antibodies. In some embodiments, the antibodies are monoclonal antibodies. In some embodiments, the monoclonal antibodies are chimeric antibodies or humanized antibodies. In some embodiments, the thrombospondin antagonists are small molecules. In some embodiments, the small molecule is gabapentin or an analog thereof. In some embodiments, the small molecule is a small molecule other than gabapentin or an analog thereof.

In some embodiments, the antagonist (e.g., agent) specifically binds to a thrombospondin. In some embodiments, the antagonist specifically binds to an EGF-like domain of the thrombospondin. In some embodiments, the antagonist specifically binds to the third EGF-like domain of the thrombospondin. In some embodiments, thrombospondin is TSP1, TSP2, TSP3, TSP4, or cartilage oligomeric matrix. In some embodiments, the antagonist is an antibody.

In some embodiments, the antagonist is a protein scaffold for antibody mimics or scaffold-derived binding proteins that display properties like small size, stability, and ease of production. These include single domains of antibodies or the immunoglobulin superfamily, protease inhibitors, helix-bundle proteins, disulphide-knotted peptides, protein A, the lipocalins, fibronectin domains, ankyrin consensus repeat domains, thioredoxin, and high disulfide density scaffold proteins.

In some embodiments, the antagonist is a siRNA, an antisense RNA, or a microRNA that specifically inhibits expression of one or more thrombospondins. In some embodiments, the expression of TSP1, TSP2, TSP4, or cartilage oligomeric matrix is inhibited.

In some embodiments of any of the methods described herein, antagonists of the α2δ subunit of a calcium channel include polypeptides, nucleic acids (e.g., RNAs (e.g., siRNA, antisense RNA, or microRNA), and DNAs), carbohydrates, immunoadhesion, calcium channel variants, calcium channel peptide antagonists, peptidomimetics, and small molecules, anti-calcium channel antibodies and immunoglobulin variants, scaffold-derived binding proteins that bind to an α2δ subunit (such as VWFA domain), amino acid variants of human calcium channel including amino acid substitution, deletion, and addition variants, or any combination thereof, and chimeric immunoglobulins. The antagonists of the α2δ subunit of a calcium channel of this invention may be based on the inventors' identification of the calcium channel domains involved in the binding of calcium channel to thrombospondin. In some embodiments, the antagonists of the α2δ subunit of a calcium channel are antibodies. In some embodiments, the antibodies are monoclonal antibodies. In some embodiments, the monoclonal antibodies are chimeric antibodies or humanized antibodies. In some embodiments, the antibodies are antibodies to α2δ1. In some embodiments, the antibodies specifically bind to the VWFA domain of an α2δ1. In some embodiments, the antagonists of the α2δ subunit of a calcium channel are small molecules. In some embodiments, the small molecule is gabapentin or an analog thereof. In some embodiments, the small molecule is a small molecule other than gabapentin or an analog thereof. In some embodiments, a modulating and/or antagonist protein comprises the polypeptide sequence of δ portion of the calcium channel subunit α2δ (e.g., the δ1 portion of the calcium channel subunit α2δ1).

In some embodiments of any of the methods described herein, antagonists include a polypeptide comprising an extracellular portion of a calcium channel α2δ subunit. In some embodiments, polypeptide comprises the α2 portion of the calcium channel subunit α2δ subunit. In some embodiments, polypeptide comprises the amino acids of about 253 to about 430 of human α2δ1 (VWFA domain). In some embodiments, polypeptide comprises an extracellular portion of a calcium channel α2δ2. In some embodiments, polypeptide comprises the α2 portion of the calcium channel subunit α2δ2. In some embodiments, polypeptide comprises the amino acids of about 291 to about 469 of human α2δ2 (VWFA domain). In some embodiments, polypeptide comprises an extracellular portion of a calcium channel α2δ3. In some embodiments, polypeptide comprises the α2 portion of a calcium channel subunit α2δ3. In some embodiments, polypeptide comprises the amino acids of about 256 to about 438 of human α2δ3 (VWFA domain). In some embodiments, polypeptide comprises an extracellular portion of a calcium channel α2δ4. In some embodiments, polypeptide comprises the α2 portion of the calcium channel subunit α2δ4. In some embodiments, polypeptide comprises the amino acids of about 291 to about 472 of human α2δ4. In some embodiments, polypeptide comprises the amino acids of about 291 to about 473 of human α2δ4. (VWFA domain).

Polypeptide sequences (including the calcium channel subunit α2δ such as the extracellular portion of the calcium channel subunit α2δ) may be altered in various ways known in the art to generate targeted changes in sequence. The polypeptide will usually be substantially similar to the sequences provided herein, i.e. will differ by at least one amino acid, and may differ by at least two but not more than about ten amino acids. The sequence changes may be substitutions, insertions or deletions. Scanning mutations that systematically introduce alanine, or other residues, may be used to determine key amino acids. Conservative amino acid substitutions typically include substitutions within the following groups: (glycine, alanine); (valine, isoleucine, leucine); (aspartic acid, glutamic acid); (asparagine, glutamine); (serine, threonine); (lysine, arginine); or (phenylalanine, tyrosine).

Modifications of interest that do not alter primary sequence include chemical derivatization of polypeptides, e.g., acetylation, or carboxylation. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine.

Also included in the subject invention are polypeptides that have been modified using ordinary molecular biological techniques and synthetic chemistry so as to improve their resistance to proteolytic degradation or to optimize solubility properties or to render them more suitable as a therapeutic agent. For examples, the backbone of the peptide may be cyclized to enhance stability (see Friedler et al. (2000) *J. Biol. Chem.* 275:23783-23789). Analogs of such polypeptides include those containing residues other than naturally occurring L-amino acids, e.g. D-amino acids or non-naturally occurring synthetic amino acids. In some embodiments, the calcium channel subunit α2δ (e.g., the extracellular portion of the calcium channel subunit α2δ), including their immunogenic epitopes and other fragments, may be combined with heterologous molecules, resulting in therapeutically useful fusion molecules. It provides fusion partners capable of imparting favorable pharmacokinetics and/or pharmacodynamics to the calcium channel subunit α2δ (e.g., the extracellular portion of the calcium channel subunit α2δ). In an embodiment, the invention provides a fusion molecule comprising all or a part of the calcium channel subunit α2δ (e.g., the extracellular portion of the calcium channel subunit α2δ), or fragments thereof and a fusion partner, such as an antibody Fc domain. The Fc domain may be further modified to remove one or more effector functions. Fusion molecules of the invention may have an increased half-life in vivo, as compared to the calcium channel subunit α2δ (e.g., the extracellular portion of the calcium channel subunit α2δ).

The subject peptides may be prepared by in vitro synthesis, using conventional methods as known in the art. Various commercial synthetic apparatuses are available, for example, automated synthesizers by Applied Biosystems, Inc., Foster City, Calif., Beckman, etc. By using synthesizers, naturally occurring amino acids may be substituted with unnatural amino acids. The particular sequence and the manner of preparation will be determined by convenience, economics, purity required, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

The polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

Synaptogenesis

Synaptogenesis is a dynamic process. During development, more synapses are established than ultimately will be retained. Therefore, the elimination of excess synaptic inputs is a critical step in synaptic circuit maturation. Synapse elimination is a competitive process that involves interactions between pre- and postsynaptic partners. In the CNS, as with the NMJ, a developmental, activity-dependent remodeling of synaptic circuits takes place by a process that may involve the selective stabilization of coactive inputs and the elimination of inputs with uncorrelated activity. The anatomical refinement of synaptic circuits occurs at the level of individual axons and dendrites by a dynamic process that involves rapid elimination of synapses. As axons branch and remodel, synapses form and dismantle with synapse elimination occurring rapidly.

Synapses are asymmetric communication junctions formed between two neurons, or, at the neuromuscular junction (NMJ) between a neuron and a muscle cell. Chemical synapses enable cell-to-cell communication via secretion of neurotransmitters, whereas in electrical synapses signals are transmitted through gap junctions, specialized intercellular channels that permit ionic current flow. In addition to ions, other molecules that modulate synaptic function (such as ATP and second messenger molecules) can diffuse through gap junctional pores. At the mature NMJ, pre- and postsynaptic membranes are separated by a synaptic cleft containing extracellular proteins that form the basal lamina. Synaptic vesicles are clustered at the presynaptic release site, transmitter receptors are clustered in junctional folds at the postsynaptic membrane, and glial processes surround the nerve terminal.

In some embodiments of any of the methods described herein, synapse formation may be increased. In some embodiments, synapses are increased due to increased new synapse formation. In some embodiments, synapses are increased due to increased synapse maintenance. In some embodiments, the synapses are at the neuromuscular junction. In some embodiments, the synapses comprise or consist of excitatory synapses. In some embodiments, the synapses are VGlut2 positive excitatory synapses. In some embodiments, the synapses are VGlut1 positive excitatory synapses. In some embodiments, the synapse formation is increased after synapse loss due to senescence. In some embodiments, the synapse formation is increase after synapses loss due to injury.

A number of cell adhesion molecules and tyrosine kinase receptor ligands have been implicated in modulating synaptogenesis. Integrins, cadherins, and neuroligins, are cell adhesion molecules that may play a role in synapse formation. The ephrins and their receptors, the Eph tyrosine kinases, participate in the activity-independent topographic organization of brain circuits and may also participate in synapse formation and maturation. Neurotrophins have also been implicated in aspects of synapse development and function. The methods of the invention are used to promote an improved outcome from ischemic cerebral injury, or other neuronal injury, by inducing synaptogenesis and cellular changes that promote functional improvement. The methods are also used to enhance synaptogenesis in patients suffering from neurodegenerative disorders, e.g. Alzheimer's disease, epilepsy, etc.

Diseases and Conditions of Interest

The methods described herein may be used to treat or prevent a variety of diseases and conditions. Among the conditions of interest for the present methods of enhancing synaptogenesis include, but not limited to, senescence, stroke, spinal cord injury, Alzheimer's disease (a disease where synapses are lost), Parkinson/s disease, multiple sclerosis, amyotrophic lateral sclerosis, neuropathy, mascular dystrophy, Huntington disease, alcoholism, Alexander's disease, Alper's disease ataxia telangiectasia, Batten disease (also known as Spielmeyer-Vogt-Sjogren-Batten disease), bovine spongiform encephalopathy (BSE), canavan disease, Cockayne syndrome, corticobasal degeneration, Creutzfeldt-Jakob disease, HIV-associated dementia, Kennedy's disease, Krabbe's disease, Lewy body dementia, Machado-Joseph disease (Spinocerebellar ataxia type 3), multiple system atrophy, narcolepsy, neuroborreliosis, Pelizaeus-Merzbacher Disease, primary lateral sclerosis, prion diseases, Progressive Supranuclear Palsy, Refsum's disease, Sandhoff's disease, Schilder's disease, subacute combined degeneration of spinal cord secondary to pernicious anaemia, schizophrenia, Spielmeyer-Vogt-Sjogren-Batten disease (also known as Batten disease), spinocerebellar ataxia (multiple types with varying characteristics), spinal muscular atrophy, Steele-Richardson-Olszewski disease, Tabes dorsalis, as well as promoting new synaptogenesis in repair and regeneration of injured CNS after stroke or spinal cord injury. Such conditions benefit from administration of thrombospondin or thrombospondin agonists, which increase, or enhance, the development of synapses. In some instances, where there has been neuronal loss, it may be desirable to enhance neurogenesis as well, e.g. through administration of agents or regimens that increase neurogenesis, transplantation of neuronal progenitors, etc.

Patients can suffer neurological and functional deficits after stroke, CNS injury, and neurodegenerative disease. The findings of the present invention provide a means to modulate synapse formation and to improve function after CNS damage or degeneration. The induction of neural connections induced by promoting synaptogenesis will promote functional improvement after stroke, injury, aging and neurodegenerative disease. The amount of increased synaptogenesis may comprise at least a measurable increase relative to a control lacking such treatment, for example at least a 10% increase, at least a 20% increase, at least a 50% increase, or more. In some embodiments, the number of synapses may be increased at least about any of 10%, 20%, 30%, 40%, 50%, or 60%. In some embodiments, the synapses are at the neuromuscular junction. In some embodiments, the synapses comprise or consist of excitatory synapses. In some embodiments, the synapses are VGlut2 positive excitatory synapses. In some embodiments, the synapses are VGlut1 positive excitatory synapses. In some embodiments, synapses are increased due to increased new synapse formation. In some embodiments, synapses are increased due to increased synapse maintenance.

In some embodiments of any of the methods described herein, an individual or subject may have suffered synapse loss as a result of senescence. In some embodiments, the individual or subject may have suffered synapse loss as a result of Alzheimer's disease, Parkinson's disease, ALS, multiple sclerosis, or glaucoma. In some embodiments, an individual or subject may have suffered macular degeneration, a hearing loss, diabetic neuropathy, or chemotherapy induced neuropathy. In some embodiments, the individual or subject may have suffered synapse loss as a result of a psychiatric disorder selected from the group consisting of acute stress disorder, agoraphobia, dissociative amnesia, anorexia nervosa, bipolar disorder, body dysmorphic disorder, brief psychotic disorder, bulimia nervosa, conversion disorder, cyclothymic disorder, delusional disorder, depersonalization disorder, dissociative identity disorder (DID), dyspareunia, dysthymic disorder, male erectile disorder, generalized anxiety disorder, impotence, pain disorder, panic disorder, phobias, posttraumatic stress disorder, schizoaffective disorder, schizophreniform, shared psychotic disorder, and substance abuse. In some embodiments, the individual may have suffered synapse loss due to injury such as spinal cord injury or central nervous system injury.

The term "stroke" broadly refers to the development of neurological deficits associated with impaired blood flow to the brain regardless of cause. Potential causes include, but are not limited to, thrombosis, hemorrhage and embolism. Current methods for diagnosing stroke include symptom evaluation, medical history, chest X-ray, ECG (electrical heart activity), EEG (brain nerve cell activity), CAT scan to assess brain damage and MRI to obtain internal body visuals. Thrombus, embolus, and systemic hypotension are among the most common causes of cerebral ischemic episodes. Other injuries may be caused by hypertension, hypertensive cerebral vascular disease, rupture of an aneurysm, an angioma, blood dyscrasias, cardiac failure, cardiac arrest, cardiogenic shock, septic shock, head trauma, spinal cord trauma, seizure, bleeding from a tumor, or other blood loss.

By "ischemic episode" is meant any circumstance that results in a deficient supply of blood to a tissue. When the ischemia is associated with a stroke, it can be either global or focal ischemia, as defined below. The term "ischemic stroke" refers more specifically to a type of stroke that is of limited extent and caused due to blockage of blood flow. Cerebral ischemic episodes result from a deficiency in the blood supply to the brain. The spinal cord, which is also a part of the central nervous system, is equally susceptible to ischemia resulting from diminished blood flow.

Senescence refers to the effects or the characteristics of increasing age, particularly with respect to the diminished ability of somatic tissues to regenerate in response to damage, disease, and normal use. Alternatively, aging may be defined in terms of general physiological characteristics. The rate of aging is very species specific, where a human may be aged at about 50 years; and a rodent at about 2 years. In general terms, a natural progressive decline in body systems starts in early adulthood, but it becomes most evident several decades later. One arbitrary way to define old age more precisely in humans is to say that it begins at conventional retirement age, around about 60, around about 65 years of age. Another definition sets parameters for aging coincident with the loss of reproductive ability, which is around about age 45, more usually around about 50 in humans, but will, however, vary with the individual. Loss of synaptic function may be found in aged individuals, such as mild cognitive deficient.

Among the aged, Alzheimer's disease is a serious condition. Alzheimer's disease is a progressive, inexorable loss of cognitive function associated with an excessive number of senile plaques in the cerebral cortex and subcortical gray matter, which also contains β-amyloid and neurofibrillary tangles consisting of tau protein. The common form affects persons >60 yr old, and its incidence increases as age advances. It accounts for more than 65% of the dementias in the elderly.

The cause of Alzheimer's disease is not known. The disease runs in families in about 15 to 20% of cases. The remaining, so-called sporadic cases have some genetic determinants. The disease has an autosomal dominant genetic pattern in most early-onset and some late-onset cases but a variable late-life penetrance. Environmental factors are the focus of active investigation.

In the course of the disease, neurons are lost within the cerebral cortex, hippocampus, and subcortical structures (including selective cell loss in the nucleus basalis of Meynert), locus caeruleus, and nucleus raphae dorsalis. Cerebral glucose use and perfusion is reduced in some areas of the brain (parietal lobe and temporal cortices in early-stage disease, prefrontal cortex in late-stage disease). Neuritic or senile plaques (composed of neurites, astrocytes, and glial cells around an amyloid core) and neurofibrillary tangles (composed of paired helical filaments) play a role in the pathogenesis of Alzheimer's disease. Senile plaques and neurofibrillary tangles occur with normal aging, but they are much more prevalent in persons with Alzheimer's disease.

The essential features of dementia are impairment of short-term memory and long-term memory, abstract thinking, and judgment; other disturbances of higher cortical function; and personality change. Progression of cognitive impairment confirms the diagnosis, and patients with Alzheimer's disease do not improve.

The methods of the invention also find use in combination with cell or tissue transplantation to the central nervous system, where such grafts include neural progenitors such as those found in fetal tissues, neural stem cells, embryonic stem cells or other cells and tissues contemplated for neural repair or augmentation. Neural stem/progenitor cells have been described in the art, and their use in a variety of therapeutic protocols has been widely discussed. For example, inter alia, U.S. Pat. No. 6,638,501, Bjornson et al.; U.S. Pat. No. 6,541,255, Snyder et al.; U.S. Pat. No. 6,498,018, Carpenter; U.S. Patent Application 20020012903, Goldman et al.; Palmer et al. (2001) *Nature* 411(6833):42-3; Palmer et al. (1997) Mol Cell Neurosci. 8(6):389-404; Svendsen et al. (1997) *Exp. Neurol.* 148(1):135-46 and Shihabuddin (1999) *Mol Med Today* 5(11):474-80; each herein specifically incorporated by reference.

Neural stem and progenitor cells can participate in aspects of normal development, including migration along well-established migratory pathways to disseminated CNS regions, differentiation into multiple developmentally- and regionally-appropriate cell types in response to microenvironmental cues, and non-disruptive, non-tumorigenic interspersion with host progenitors and their progeny. Human NSCs are capable of expressing foreign transgenes in vivo in these disseminated locations. As such, these cells find use in the treatment of a variety of conditions, including traumatic injury to the spinal cord, brain, and peripheral nervous system; treatment of degenerative disorders including Alzheimer's disease, Huntington's disease, Parkinson's disease; affective disorders including major depression; stroke; and the like. By synaptogenesis enhancers, the functional connections of the neurons are enhances, providing for an improved clinical outcome.

Where a synaptogenesis inhibitor of the invention is administered, the decrease in synaptogenesis may comprise at least a measurable decrease relative to a control lacking such treatment, for example at least a 10% decrease, at least a 20% decrease, at least a 50% decrease, or more. In some embodiments, the number of synapses may be inhibited at least about any of 10%, 20%, 30%, 40%, 50%, or 60%. In some embodiments, the synapses are at the neuromuscular junction. In some embodiments, the synapses comprise or consist of excitatory synapses. In some embodiments, the synapses are VGlut2 positive excitatory synapses. In some embodiments, the synapses are VGlut1 positive excitatory synapses.

Among the conditions of interest for the present methods of decreasing synaptogenesis are in the treatment of pain, epilepsy, anxiety, addiction, and to aid in the axon growth of regenerating neurons. Such conditions benefit from administration of thrombospondin antagonists, which decrease, or inhibit, the development of synapses. Any antagonists described herein may be used, such as antibodies and fragments thereof that specifically bind to a thrombospondin (such as the EGF-like domain of a thrombospondin); and molecules that bind to a calcium channel α2δ subunit (e.g., an α2δ subunit of calcium channel, such as α2δ1, α2δ2, α2δ3, and α2δ4), e.g. an antibody that specifically binds to VWFA domain of an α2δ, gabapentin and analogs thereof, particularly including analogs identified by the screening methods described herein.

Epilepsy is a recurrent, paroxysmal disorder of cerebral function characterized by sudden, brief attacks of altered consciousness, motor activity, sensory phenomena, or inappropriate behavior caused by excessive discharge of cerebral neurons. Manifestations depend on the type of seizure, which may be classified as partial or generalized. In partial seizures, the excess neuronal discharge is contained within one region of the cerebral cortex. In generalized seizures, the discharge bilaterally and diffusely involves the entire cortex. Sometimes a focal lesion of one part of a hemisphere activates the entire cerebrum bilaterally so rapidly that it produces a generalized tonic-clonic seizure before a focal sign appears.

Most patients with epilepsy become neurologically normal between seizures, although overuse of anticonvulsants can dull alertness. Progressive mental deterioration is usually related to the neurologic disease that caused the seizures. Left temporal lobe epilepsy is associated with verbal memory abnormalities; right temporal lobe epilepsy sometimes causes visual spatial memory abnormalities. The outlook is best when no brain lesion is demonstrable.

If a peripheral nerve is partially damaged, function is restored before the severed fibers regenerate. The peripheral nervous system, spinal cord and brain have all been shown to sprouting and circuitry remodeling. Following injury, regions not primarily associated with the lesion also exhibit synaptic density changes and subsequent recovery of control levels over a long period of time. The synaptic changes occur despite the absence of degenerating terminals within these zones. Thus, pronounced transneuronal changes may occur after major trauma to the CNS, suggesting that reactive synaptogenesis may adjust the functional integrity of complex circuitry in areas with and without a primary lesion. When an injury occurs in the mature brain, the growth process must be executed in the context of a damaged system. The old system must be cleared and coordinated with the initiation of growth and the formation of new synapses. The capacity for extensive remodeling and growth is desirably restrained when such remodeling is not required. In such conditions, an inhibitor of synaptogenesis according to the present invention may be administered for a period of time sufficient to permit neuron growth, prior to synapse formation.

Synaptogenesis is involved in the underlying neural basis of alcoholism and drug addiction. Neurobiological studies have identified specific brain areas and molecular mechanisms involved in drug abuse and dependence. Drug-induced persistent behaviors such as sensitization, tolerance or relapse far outlast any previously reported molecular mechanisms. Ultrastructural evidence of synaptic rewiring has been found in association with cocaine-induced behavioral sensitization. Such synaptic remodeling represents a potential neural substrate underlying the persistence of addiction. Site-specific pharmacotherapeutic and behavioral treatment programs for alcoholism and drug addiction can then target these circuits. In such conditions, an inhibitor of synaptogenesis according to the present invention may be administered for a period of time sufficient to inhibit synapse formation associated with addiction.

The findings of the present invention also provide a means to modulate axonal and/or dendritic growth and to improve function after CNS damage. The induction of axonal and/or dendritic growth will promote functional improvement after injury. The amount of increase in axonal and/or dendritic growth may comprise at least a measurable increase relative to a control lacking such treatment, for example at least a 10% increase, at least a 20% increase, at least a 50% increase, or more. In some embodiments, the axonal and/or dendritic growth may be increased at least about any of 10%, 20%, 30%, 40%, 50%, or 60%. In some embodiments, the axonal and/or dendritic growth is axon growth. In some embodiments, the axonal and/or dendritic growth is dendritic growth. Where an axonal and/or dendritic growth inhibitor of the invention is administered, the decrease in axonal and/or dendritic growth may comprise at least a measurable decrease relative to a control lacking such treatment, for example at least a 10% decrease, at least a 20% decrease, at least a 50% decrease, or more. In some embodiments, the axonal and/or dendritic growth may be inhibited at least about any of 10%, 20%, 30%, 40%, 50%, or 60%. In some embodiments, the axonal and/or dendritic growth inhibited is axonal growth. In some embodiments, the axonal and/or dendritic growth inhibited is dendritic growth.

In some embodiments of any of the methods described herein, the individual may have suffered axonal and/or dendritic degeneration as a result of a spinal cord injury. In some embodiments, the individual has suffered axonal and/or dendritic degeneration as a result of Alzheimer's disease, Parkinson's disease, ALS, or multiple sclerosis. In some embodiments, the individual has suffered a macular degeneration, a hearing loss, a diabetic neuropathy, or a chemotherapy induced neuropathy. In some embodiments, the individual has suffered axonal and/or dendritic degeneration as a result of a psychiatric disorder selected from the group consisting of acute stress disorder, agoraphobia, dissociative amnesia, anorexia nervosa, bipolar disorder, body dysmorphic disorder, brief psychotic disorder, bulimia nervosa, conversion disorder, cyclothymic disorder, delusional disorder, depersonalization disorder, dissociative identity disorder (DID), dysparenunia, dysthymic disorder, male erectile disorder, generalized anxiety disorder, impotence, pain disorder, panic disorder, phobias, posttraumatic stress disorder, schizoaffective disorder, schizophreniform, shared psychotic disorder, and substance abuse.

The antagonists described herein may also be used for treating or preventing a disorder characterized by excess of calcium influx in an individual. The invention provides methods comprising administering to the individual an effective amount of an agent that blocks the interaction between a thrombospondin and a calcium subunit selected from the group consisting of $\alpha 2\delta 1$, $\alpha 2\delta 2$, $\alpha 2\delta 3$, and $\alpha 2\delta 4$. In some embodiments, the agent (such as an antibody) specifically binds to a thrombospondin. In some embodiments, the disorder is muscle spasm, migraine, stroke, or Parkinson's disease.

Gene Delivery

One approach for modulating synaptogenesis involves gene therapy. In such methods, sequences encoding an agonist or an antagonist described herein, such as peptide comprising at least one thrombospondin EGF-like domain, RNAi sequence, or antibodies, are introduced into the central nervous system, and expressed, as a means of providing agonist or antagonist activity to the targeted cells. To genetically modify neurons that are protected by the BBB, two general categories of approaches have been used. In one type of approach, cells are genetically altered, outside the body, and then transplanted somewhere in the CNS, usually in an area inside the BBB. In the other type of approach, genetic "vectors" are injected directly into one or more regions in the CNS, to genetically alter cells that are normally protected by the BBB. It should be noted that the terms "transfect" and "transform" are used interchangeably herein. Both terms refer to a process which introduces a foreign gene (also called an "exogenous" gene) into one or more preexisting cells, in a manner which causes the foreign gene(s) to be expressed to form corresponding polypeptides.

A preferred approach aims to introduce into the CNS a source of a desirable polypeptide, by genetically engineering cells within the CNS. This has been achieved by directly injecting a genetic vector into the CNS, to introduce foreign genes into CNS neurons "in situ" (i.e., neurons which remain in their normal position, inside a patient's brain or spinal cord, throughout the entire genetic transfection or transformation procedure).

Useful vectors include viral vectors, which make use of the lipid envelope or surface shell (also known as the capsid) of a virus. These vectors emulate and use a virus's natural ability to (i) bind to one or more particular surface proteins on certain types of cells, and then (ii) inject the virus's DNA or RNA into the cell. In this manner, viral vectors can deliver and transport a genetically engineered strand of DNA or RNA through the outer membranes of target cells, and into the cells cytoplasm. Gene transfers into CNS neurons have been reported using such vectors derived from herpes simplex viruses (e.g., European Patent 453242, Breakfield et al 1996), adenoviruses (La Salle et al 1993), and adeno-associated viruses (Kaplitt et al 1997).

Non-viral vectors typically contain the transcriptional regulatory elements necessary for expression of the desired gene, and may include an origin of replication, selectable markers and the like, as known in the art. The non-viral genetic vector is then created by adding, to a gene expression construct, selected agents that can aid entry of the gene construct into target cells. Several commonly-used agents include cationic lipids, positively charged molecules such as polylysine or polyethylenimine, and/or ligands that bind to receptors expressed on the surface of the target cell. For the purpose of this discussion, the DNA-adenovirus conjugates described by Curiel (1997) are regarded as non-viral vectors, because the adenovirus capsid protein is added to the gene expression construct to aid the efficient entry of the gene expression construct into the target cell.

In cationic gene vectors, DNA strands are negatively charged, and cell surfaces are also negatively charged. Therefore, a positively-charged agent can help draw them together, and facilitate the entry of the DNA into a target cell. Examples of positively-charged transfection agents include polylysine, polyethylenimine (PEI), and various cationic lipids. The basic procedures for preparing genetic vectors using cationic agents are similar. A solution of the cationic agent (polylysine, PEI, or a cationic lipid preparation) is added to an aqueous solution containing DNA (negatively charged) in an appropriate ratio. The positive and negatively charged components will attract each other, associate, condense, and form molecular complexes. If prepared in the appropriate ratio, the resulting complexes will have some positive charge, which will aid attachment and entry into the negatively charged surface of the target cell. The use of liposomes to deliver foreign genes into sensory neurons is described in various articles such as Sahenk et al 1993. The use of PEI, polylysine, and other cationic agents is described in articles such as Li et al 2000 and Nabel et al 1997.

An alternative strategy for introducing DNA into target cells is to associate the DNA with a molecule that normally enters the cell. This approach was demonstrated in liver cells in U.S. Pat. No. 5,166,320 (Wu et al 1992). An advantage of this approach is that DNA delivery can be targeted to a particular type of cell, by associating the DNA with a molecule that is selectively taken up by that type of target cell. A limited number of molecules are known to undergo receptor mediated endocytosis in neurons. Known agents that bind to neuronal receptors and trigger endocytosis, causing them to enter the neurons, include (i) the non-toxic fragment C of tetanus toxin (e.g., Knight et al 1999); (ii) various lectins derived from plants, such as barley lectin (Horowitz et al 1999) and wheat germ agglutinin lectin (Yoshihara et al 1999); and, (iii) certain neurotrophic factors (e.g., Barde et al 1991). At least some of these endocytotic agents undergo "retrograde" axonal transport within neuron. The term "retrograde", in this context, means that these molecules are actively transported, by cellular processes, from the extremities (or "terminals") of a neuron, along an axon or dendrite, toward and into the main body of the cell, where the nucleus is located. This direction of movement is called "retrograde", because it runs in the opposite direction of the normal outward ("anterograde") movement of most metabolites inside the cell (including proteins synthesized in the cell body, neurotransmitters synthesized by those proteins, etc.).

Methods of Administration and Dosages

As such, administration of the compounds (including agonists and antagonists described herein) can be achieved in various ways, including oral, buccal, rectal, parenteral, intraperitoneal, intradermal, transdermal, intrathecal, nasal, intranasal, topical, intravenous, intraarterial, intramuscular, subcutaneous, subdermal, intracranial, ophthalmic (e.g., topical, injection (e.g., subconjunctival, subtenon, intravitreal, etc.), or implantation), or intrathecal administration. The active agent may be systemic after administration or may be localized by the use of regional administration, intramural administration, or use of an implant that acts to retain the active dose at the site of implantation.

The compositions of the invention may be administered using any medically appropriate procedure, e.g. intravascular (intravenous, intraarterial, intracapillary) administration, injection into the cerebrospinal fluid, intracavity or direct injection in the brain. Intrathecal administration maybe carried out through the use of an Ommaya reservoir, in accordance with known techniques. (F. Balis et al., *Am J. Pediatr. Hematol. Oncol.* 11, 74, 76 (1989).

One strategy for drug delivery through the blood brain barrier (BBB) entails disruption of the BBB, either by osmotic means such as mannitol or leukotrienes, or biochemically by the use of vasoactive substances such as bradykinin. The potential for using BBB opening to target specific agents is also an option. A BBB disrupting agent can be co-administered with the therapeutic compositions of the invention when the compositions are administered by intravascular injection. Other strategies to go through the BBB may entail the use of endogenous transport systems, including carrier-mediated transporters such as glucose and amino acid carriers, receptor-mediated transcytosis for insulin or transferrin, and active efflux transporters such as p-glycoprotein. Active transport moieties may also be conjugated to the therapeutic or imaging compounds for use in the invention to facilitate transport across the epithelial wall of the blood vessel. Alternatively, drug delivery behind the BBB is by intrathecal delivery of therapeutics or imaging agents directly to the cranium, as through an Ommaya reservoir.

Where the therapeutic agents are locally administered in the brain, one method for administration of the therapeutic compositions of the invention is by deposition into or near the site by any suitable technique, such as by direct injection (aided by stereotaxic positioning of an injection syringe, if necessary) or by placing the tip of an Ommaya reservoir into a cavity, or cyst, for administration. Alternatively, a convection-enhanced delivery catheter may be implanted directly into the site, into a natural or surgically created cyst, or into the normal brain mass. Such convection-enhanced pharmaceutical composition delivery devices greatly improve the diffusion of the composition throughout the brain mass. The implanted catheters of these delivery devices utilize high-flow microinfusion (with flow rates in the range of about 0.5 to 15.0 µl/minute), rather than diffusive flow, to deliver the therapeutic composition to the brain and/or tumor mass. Such devices are described in U.S. Pat. No. 5,720,720, incorporated fully herein by reference.

In some embodiments of the methods of treatment and methods of administration described herein, the methods include administering an effective amount of an agent to promote synapse formation. In some embodiments of the methods of treatment and methods of administration described herein, the methods include administering an effective amount of an agent to inhibit synapse formation. In some embodiments of the methods of treatment and methods of administration described herein, the methods include administering an effective amount of an agent to promote axonal and/or growth. In some embodiments of the methods of treatment and methods of administration described herein, the methods include administering an effective amount of an agent to inhibit axonal and/or dendritic growth. In some embodiments, the agent is an antagonist. In some embodiments, the agent is an agonist.

In some embodiments of the methods of treatment and methods of administration described herein, the methods comprise administering one or more modulators described herein (e.g., two modulators (e.g., an antagonist and an agonist)). In some embodiments, the methods include (a) administering an effective amount of a first agent to promote axonal and/or dendritic growth and (b) administering an effective amount of a second agent to promote synapse formation. In some embodiments, the first agent is an antagonist of a thrombospondin and/or a α2δ subunit of a calcium channel. In some embodiments, the second agent is an agonist of a thrombospondin. In some embodiments, the first agent and second agent are administered sequentially. In some embodiments, the first agent and second agent are administered separately. In some embodiments, the first agent is administered less than about any of 1, 2, 3, 4, 5, 6, 7, 8, 9, or 10 days prior to the second agent. In some embodiments, the second agent is administered less than about any of 1, 3, 6, 9, 12, 18, 24, hours after first agent.

The methods of treatment and methods of administration described herein including agonists and/or antagonists of the present invention, are administered at a dosage that modulates synaptogenesis and/or axon growth while minimizing any side-effects. It is contemplated that compositions will be obtained and used under the guidance of a physician for in vivo use. The dosage of the therapeutic formulation will vary widely, depending upon the nature of the disease, the frequency of administration, the manner of administration, the clearance of the agent from the host, and the like.

The pharmaceutical compositions can be administered for prophylactic and/or therapeutic treatments. Toxicity and therapeutic efficacy of the active ingredient can be determined according to standard pharmaceutical procedures in cell cultures and/or experimental animals, including, for example, determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred.

The data obtained from cell culture and/or animal studies can be used in formulating a range of dosages for humans. The dosage of the active ingredient typically lines within a range of circulating concentrations that include the $ED_{50}$ with low toxicity. The dosage can vary within this range depending upon the dosage form employed and the route of administration utilized.

The effective amount of a therapeutic composition described herein to be given to a particular patient will depend on a variety of factors, several of which will be different from patient to patient. Dosage of the agent will depend on the treatment, route of administration, the nature of the therapeutics, sensitivity of the patient to the therapeutics, etc. Utilizing $LD_{50}$ animal data, and other information, a clinician can determine the maximum safe dose for an individual, depending on the route of administration. Utilizing ordinary skill, the competent clinician will be able to optimize the dosage of a particular therapeutic composition in the course of routine clinical trials. The compositions can be administered to the subject in a series of more than one administration. For therapeutic compositions, regular periodic administration will sometimes be required, or may be desirable. Therapeutic regimens will vary with the agent, e.g. some agents may be taken for extended periods of time on a daily or semi-daily basis, while more selective agents may be administered for more defined time courses, e.g. one, two three or more days, one or more weeks, one or more months, etc., taken daily, semi-daily, semi-weekly, weekly, etc.

Pharmaceutically Acceptable Compositions and Formulations

Therapeutic agents, e.g. agonists or antagonists can be incorporated into a variety of formulations for therapeutic administration by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. Pharmaceutical compositions can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

The composition can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249:1527-1533 (1990).

For oral administration, the active ingredient can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

Formulations may be optimized for retention and stabilization in the brain. When the agent is administered into the cranial compartment, it is desirable for the agent to be retained in the compartment, and not to diffuse or otherwise cross the blood brain barrier. Stabilization techniques include cross-linking, multimerizing, or linking to groups such as polyethylene glycol, polyacrylamide, neutral protein carriers, etc. in order to achieve an increase in molecular weight.

Other strategies for increasing retention include the entrapment of the agent in a biodegradable or bioerodible implant. The rate of release of the therapeutically active agent is controlled by the rate of transport through the polymeric matrix, and the biodegradation of the implant. The transport of drug through the polymer barrier will also be affected by compound solubility, polymer hydrophilicity, extent of polymer cross-linking, expansion of the polymer upon water absorption so as to make the polymer barrier more permeable to the drug, geometry of the implant, and the like. The implants are of dimensions commensurate with the size and shape of the region selected as the site of implantation. Implants may be particles, sheets, patches, plaques, fibers, microcapsules and the like and may be of any size or shape compatible with the selected site of insertion.

The implants may be monolithic, i.e. having the active agent homogenously distributed through the polymeric matrix, or encapsulated, where a reservoir of active agent is encapsulated by the polymeric matrix. The selection of the polymeric composition to be employed will vary with the site of administration, the desired period of treatment, patient tolerance, the nature of the disease to be treated and the like. Characteristics of the polymers will include biodegradability at the site of implantation, compatibility with the agent of interest, ease of encapsulation, a half-life in the physiological environment.

Biodegradable polymeric compositions which may be employed may be organic esters or ethers, which when degraded result in physiologically acceptable degradation products, including the monomers. Anhydrides, amides, orthoesters or the like, by themselves or in combination with other monomers, may find use. The polymers will be condensation polymers. The polymers may be cross-linked or non-cross-linked. Of particular interest are polymers of hydroxy-aliphatic carboxylic acids, either homo- or copolymers, and polysaccharides. Included among the polyesters of interest are polymers of D-lactic acid, L-lactic acid, racemic lactic acid, glycolic acid, polycaprolactone, and combinations thereof. By employing the L-lactate or D-lactate, a slowly biodegrading polymer is achieved, while degradation is substantially enhanced with the racemate. Copolymers of glycolic and lactic acid are of particular interest, where the rate of biodegradation is controlled by the ratio of glycolic to lactic acid. The most rapidly degraded copolymer has roughly equal amounts of glycolic and lactic acid, where either homopolymer is more resistant to degradation. The ratio of glycolic acid to lactic acid will also affect the brittleness of in the implant, where a more flexible implant is desirable for larger geometries. Among the polysaccharides of interest are calcium alginate, and functionalized celluloses, particularly carboxymethylcellulose esters characterized by being water insoluble, a molecular weight of about 5 kD to 500 kD, etc. Biodegradable hydrogels may also be employed in the implants of the subject invention. Hydrogels are typically a copolymer material, characterized by the ability to imbibe a liquid. Exemplary biodegradable hydrogels which may be employed are described in Heller in: Hydrogels in Medicine and Pharmacy, N. A. Peppes ed., Vol. III, CRC Press, Boca Raton, Fla., 1987, pp 137-149.

Articles of Manufacture and Kits

The invention provides articles of manufacture comprising the compositions, formulations, and unit dosages described herein in suitable packaging for use in the methods of treatment and methods of administration described herein. Suitable packaging for compositions described herein are known in the art, and include, for example, vials (such as sealed vials), vessels (such as sealed vessels), ampules, bottles, jars, flexible packaging (e.g., sealed Mylar or plastic bags), and the like. These articles of manufacture may further be sterilized and/or sealed.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration.

Instructions supplied in the kits of the invention are typically written instructions on a label or package insert (e.g., a paper sheet included in the kit), but machine-readable instructions (e.g., instructions carried on a magnetic or optical storage disk) are also acceptable. The instructions relating to the use of the nanoparticle compositions generally include information as to dosage, dosing schedule, and route of administration for the intended treatment. The kit may further comprise a description of selecting an individual suitable or treatment.

The present invention further provides kits comprising compositions (or unit dosages forms and/or articles of manufacture) described herein and may further comprise instruction(s) on methods of using the composition, such as uses further described herein. In some embodiments, the kit of the invention comprises the packaging described above. In other embodiments, the kit of the invention comprises the packaging described above and a second packaging comprising a buffer. It may further include other materials desirable from a commercial and user standpoint, including other buffers, diluents, filters, needles, syringes, and package inserts with instructions for performing any methods described herein.

Methods for Screening

In some aspects of the invention, the invention provides methods for screening a candidate agent for activity in enhancing synaptogenesis, the method comprising: a) measuring binding of a candidate agent to an α2δ polypeptide (e.g., α2δ1 polypeptide) or a thrombospondin EGF-like domain; b) quantitating formation of synapses in a neural cell culture in the presence of the candidate agent if the candidate agent binds to the α2δ polypeptide (e.g., α2δ1 polypeptide) or the thrombospondin EGF-like domain in step a), wherein an increased formation of synapses in the presence the candidate agent as compared to the formation of synapses in the absence of the candidate agent indicates that the candidate agent has the activity in enhancing synaptogenesis. The invention also provides methods for screening a candidate agent for activity in inhibiting synaptogenesis, the method comprising: a) measuring binding of a candidate agent to an α2δ polypeptide (e.g., α2δ1 polypeptide) or a thrombospondin EGF-like domain; b) quantitating formation of synapses in a neural cell culture in the presence of the candidate agent and a thrombospondin agonist if the candidate agent binds to the α2δ polypeptide (e.g., α2δ1 polypeptide) or the thrombospondin EGF-like domain in step a), wherein a decreased formation of synapses in the presence the candidate agent as compared formation of synapses in the absence of the candidate agent indicates that the candidate agent has the activity in inhibiting synaptogenesis.

Candidate agents are screened for the ability to modulate synaptogenesis, which agents may include candidate thrombospondin derivatives, variants, fragments, mimetics, agonists and antagonists, and/or GABA analogs and mimetics. Agents of interest may be screened against calcium channel subunit α2δ (e.g., subunit α2δ1), and/or a polypeptide comprising at least one thrombospondin EGF-like domain. Such compound screening may be performed using an in vitro model, a cell expressing the polypeptide, including a genetically altered cell or animal, or purified protein. A wide variety of assays may be used for this purpose. In one embodiment, compounds that are predicted to be antagonists or agonists of synaptogenesis are initially tested for binding to calcium channel subunit α2δ (e.g., calcium channel subunit α2δ1), or for interacting with a thrombospondin EGF-like domain. The compounds may then be further tested for functional activity in a biological model, e.g. an in vitro culture system, as described below, an animal model, etc.

For example, candidate agents may be identified by known pharmacology, by structure analysis, by rational drug design using computer based modeling, by binding assays, and the like. Various in vitro models may be used to determine whether a compound binds to, or otherwise affects thrombospondin activity. Such candidate compounds are used to contact neurons in an environment permissive for synaptogenesis. Such compounds may be further tested in an in vivo model for enhanced synaptogenesis.

Synaptogenesis is quantitated by administering the candidate agent to neurons in culture, and determining the presence of synapses in the absence or presence of the agent. In one embodiment of the invention, the neurons are a primary culture, e.g. of RGCs. Purified populations of RGCs are obtained by conventional methods, such as sequential immunopanning. The cells are cultured in suitable medium, which will usually comprise appropriate growth factors, e.g. CNTF; BDNF; etc. As a positive control, soluble thrombospondin, e.g. TSP1, TSP2, etc. may be added to certain wells. The neural cells, e.g. RCGs, are cultured for a period of time sufficient allow robust process outgrowth and then cultured with a candidate agent for a period of about 1 day to 1 week, to allow synapse formation. For synapse quantification, cultures are fixed, blocked and washed, then stained with antibodies specific synaptic proteins, e.g. synaptotagmin, etc. and visualized with an appropriate reagent, as known in the art. Analysis of the staining may be performed microscopically. In one embodiment, digital images of the fluorescence emission are with a camera and image capture software, adjusted to remove unused portions of the pixel value range and the used pixel values adjusted to utilize the entire pixel value range. Corresponding channel images may be merged to create a color (RGB) image containing the two single-channel images as individual color channels. Co-localized puncta can be identified using a rolling ball background subtraction algorithm to remove low-frequency background from each image channel. Number, mean area, mean minimum and maximum pixel intensities, and mean pixel intensities for all synaptotagmin, PSD-95, and colocalized puncta in the image are recorded and saved to disk for analysis.

In some embodiments, candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Generally a plurality of assay mixtures are run in parallel with different agent concentrations to obtain a differential response to the various concentrations. Typically one of these concentrations serves as a negative control, i.e. at zero concentration or below the level of detection.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. Test agents can be obtained from libraries, such as natural product libraries or combinatorial libraries, for example.

Libraries of candidate compounds can also be prepared by rational design. (See generally, Cho et al., *Pac. Symp. Biocompat.* 305-16, (1998); Sun et al., *J. Comput. Aided Mol. Des.* 12:597-604, 1998); each incorporated herein by reference in their entirety). For example, libraries of phosphatase inhibitors can be prepared by syntheses of combinatorial chemical libraries (see generally DeWitt et al., *Proc. Nat. Acad. Sci. USA* 90:6909-13, 1993; International Patent Publication WO 94/08051; Baum, *Chem. & Eng. News* 72:20-25, 1994; Burbaum et al., *Proc. Nat. Acad. Sci. USA* 92:6027-31, 1995; Baldwin et al., *J. Am. Chem. Soc.* 117:5588-89, 1995; Nestler et al., *J. Org. Chem.* 59:4723-24, 1994; Borehardt et al., *J. Am. Chem. Soc.* 116:373-74, 1994; Ohlmeyer et al., *Proc. Nat. Acad. Sci. USA* 90:10922-26, all of which are incorporated by reference herein in their entirety.)

A "combinatorial library" is a collection of compounds in which the compounds comprising the collection are composed of one or more types of subunits. Methods of making combinatorial libraries are known in the art, and include the following: U.S. Pat. Nos. 5,958,792; 5,807,683; 6,004,617; 6,077,954; which are incorporated by reference herein. The subunits can be selected from natural or unnatural moieties. The compounds of the combinatorial library differ in one or more ways with respect to the number, order, type or types of modifications made to one or more of the subunits comprising the compounds. Alternatively, a combinatorial library may refer to a collection of "core molecules" which vary as to the number, type or position of R groups they contain and/or the identity of molecules composing the core molecule. The collection of compounds is generated in a systematic way. Any method of systematically generating a collection of compounds differing from each other in one or more of the ways set forth above is a combinatorial library.

A combinatorial library can be synthesized on a solid support from one or more solid phase-bound resin starting materials. The library can contain five (5) or more, preferably ten (10) or more, organic molecules that are different from each other. Each of the different molecules is present in a detectable amount. The actual amounts of each different molecule needed so that its presence can be determined can vary due to the actual procedures used and can change as the technologies for isolation, detection and analysis advance. When the molecules are present in substantially equal molar amounts, an amount of 100 picomoles or more can be detected. Preferred libraries comprise substantially equal molar amounts of each desired reaction product and do not include relatively large or small amounts of any given molecules so that the presence of such molecules dominates or is completely suppressed in any assay.

Combinatorial libraries are generally prepared by derivatizing a starting compound onto a solid-phase support (such as a bead). In general, the solid support has a commercially available resin attached, such as a Rink or Merrifield Resin. After attachment of the starting compound, substituents are attached to the starting compound. Substituents are added to the starting compound, and can be varied by providing a mixture of reactants comprising the substituents. Examples of suitable substituents include, but are not limited to, hydrocarbon substituents, e.g. aliphatic, alicyclic substituents, aromatic, aliphatic and alicyclic-substituted aromatic nuclei, and the like, as well as cyclic substituents; substituted hydrocarbon substituents, that is, those substituents containing non-hydrocarbon radicals which do not alter the predominantly hydrocarbon substituent (e.g., halo (especially chloro and fluoro), alkoxy, mercapto, alkylmercapto, nitro, nitroso, sulfoxy, and the like); and hetero substituents, that is, substituents which, while having predominantly hydrocarbyl character, contain other than carbon atoms. Suitable heteroatoms include, for example, sulfur, oxygen, nitrogen, and such substituents as pyridyl, furanyl, thiophenyl, imidazolyl, and the like. Heteroatoms, and typically no more than one, can be present for each carbon atom in the hydrocarbon-based substituents. Alternatively, there can be no such radicals or heteroatoms in the hydrocarbon-based substituent and, therefore, the substituent can be purely hydrocarbon.

Compounds that are initially identified by any screening methods can be further tested to validate the apparent activity. The basic format of such methods involves administering a lead compound identified during an initial screen to an animal that serves as a model for humans and then determining the effects on synaptogenesis. The animal models utilized in validation studies generally are mammals. Specific examples of suitable animals include, but are not limited to, primates, mice, and rats.

EXAMPLES

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

Example 1

The number of synapses between CNS neurons in culture is profoundly enhanced by a soluble signal secreted by astrocytes, which are identified herein as thrombospondins (TSPs), which are a necessary and sufficient component of the synapse-promoting activity of astrocyte-conditioned medium. TSPs induce ultrastructurally normal synapses that are presynaptically active but postsynaptically inactive. In vivo, TSPs are concentrated in astrocytes and at synapses throughout the developing brain, and mice deficient in both TSP1 and its ortholog TSP2 have a significant decrease in synapse number.

TSPs are large oligomeric extracellular matrix proteins, about 500 kD, that mediate cell-cell and cell-matrix interactions by binding an array of membrane receptors, other extracellular matrix proteins, and cytokines. There are five TSPs, each encoded by a separate gene. Although several TSPs are expressed in the brain, the functions of these TSPs are unknown. TSP1 and TSP2 are closely related trimeric proteins that share the same set of structural and functional domains. TSP4, which is pentameric and has a different domain structure from TSP1 and TSP2, is present in the adult nervous system where it is localized to some CNS synapses as well as the neuromuscular junction.

All 5 TSP isoforms have strong synapse inducing activity as a result of sharing a common EGF like domain. Using this domain, we have identified that TSP induces synapse formation through a novel interaction with a widely expressed transmembrane neuronal cell surface molecule, calcium channel subunit alpha2 delta1, which has not been previously linked to synapse formation.

Gabapentin, which is used as antiepileptic and anti-neuropathic pain agent, has been previously shown to bind to this receptor, but its mechanism of action has long been a mystery. We have shown that Gabapentin in culture is able to specifically inhibit the synapse forming activity of thrombospondin or its domain. This action is specific for thrombospondin as Gabapentin does not inhibit the synapse formation induced by another astrocyte secreted synaptogenic protein Hevin.

As shown in FIG. 1A, all TSPs are extracellular multimeric, multidomain, calcium-binding glycoproteins that function at cell surfaces and in the extracellular matrix milieu. The thrombospondin gene family is divided into two subgroups. Subgroup A thrombospondins includes TSP1 and 2, which are trimeric and have larger N terminal domains (black oval) and which have three additional properdin like repeats (rectangles). Subgroup B TSPs are pentameric and lack the properdin like repeats.

Previously, it was shown that Subgroup A TSP1 and 2 are synaptogenic (Christopherson et. al. *Cell*, 2005). Here it is shown that pentameric Subgroup B thrombospondins are also synaptogenic. Immuno staining of RGCs for co-localization of presynaptic Synaptotagmin and postsynaptic PSD-95 showed few colocalized synaptic puncta in the absence of astrocytes (B) but many were found in the presence of a feeding layer of astrocytes (FIG. 1C).

RGCs cultures with conditioned media from COS7 cells transfected with TSP3 overexpression vector (FIG. 1D) or with purified TSP4 (FIG. 1E) or TSP5 (FIG. 1F) formed many synapses, which are observed as co-localized pre and post-synaptic puncta. Quantification of the effects of astrocytes and TSPs on synaptic puncta is shown in FIG. 1G. Astrocytes and TSP1, TSP4 and TSP5 both significantly increased the number of co-localized synaptic puncta/cell over RGCs alone (Control). Shown in FIG. 1H, culturing RGCs with the conditioned media from COS7 cells transfected with TSP3 overexpression vector significantly increased the number of co-localized synaptic puncta/cell when compared with RGCs cultured with conditioned media from COS7 cells transfected with empty vector (Control) (*$p<0.05$, n=20, error bars indicate SEM values).

Shown in FIG. 2A is the thrombospondin domain structure. TSP1 and 2 consist of a heparin-binding N terminal domain (C), a linker with homology to procollagen (PC), three TSP-type-1 (properdin) repeats, three EGF-like (TSP-type-2) repeats, seven TSP type-3 (calcium binding) repeats, and a cell-binding carboxyl-terminal domain (C).

The quantification of the effects of TSP1 (B) and TSP2 (C) domains on the number of synapses formed by RGCs in vitro is shown in FIG. 2B. Astrocytes and purified TSP1 (trimeric-8 nM) increased the number of synapses formed by RGCs significantly when compared to RGCs cultured alone. Interestingly TSP1 trunctation constructs (monomeric-20 nM) that contained the EGF-like repeats (blue) could also significantly increase the synapse number.

Shown in FIG. 2C, similarly purified recombinant TSP2 domains (monomeric-20 nM) that contained the EGF-like repeats of TSP2 increased the number of synapses formed by RGCs significantly when compared to RGCs cultured alone. Interestingly a construct that contained only the third EGF-like domain together with the C-terminal end of TSP2 was also synaptogenic. However, the third EGF-like repeat (blue) alone did not significantly increase the synapse number. (FIGS. 2D, E). Antibodies against EGF like repeats of TSPs can block their synaptogenic effect. RGCs cultured with astrocytes or with the recombinant TSP1 (FIG. 2D) or TSP2 (FIG. 2E) truncation constructs that contained the third properdin repeats with the three EGF-like domains (will be referred as EGF-like domain here on) formed many more synapses when compared to RGCs cultured alone.

Interestingly, a monoclonal antibody A4.1 (Neomarkers) that binds to the third EGF-like domain of TSPs blocked the synaptogenic effect of both TSP1 and TSP2 synaptogenic constructs. Another monoclonal antibody C6.7 (Neomarkers) that binds to the second EGF-like repeats of TSPs did not affect the synaptogenic function of TSP1 construct however it was able to block the synaptogenic TSP2 domain. These data show that the synaptogenic effect of TSPs is mediated through the EGF-like repeats of TSPs and most likely through an interaction mapped to the third EGF-like domain. (*$p<0.05$, n=20, error bars indicate SEM values).

Figure 3:
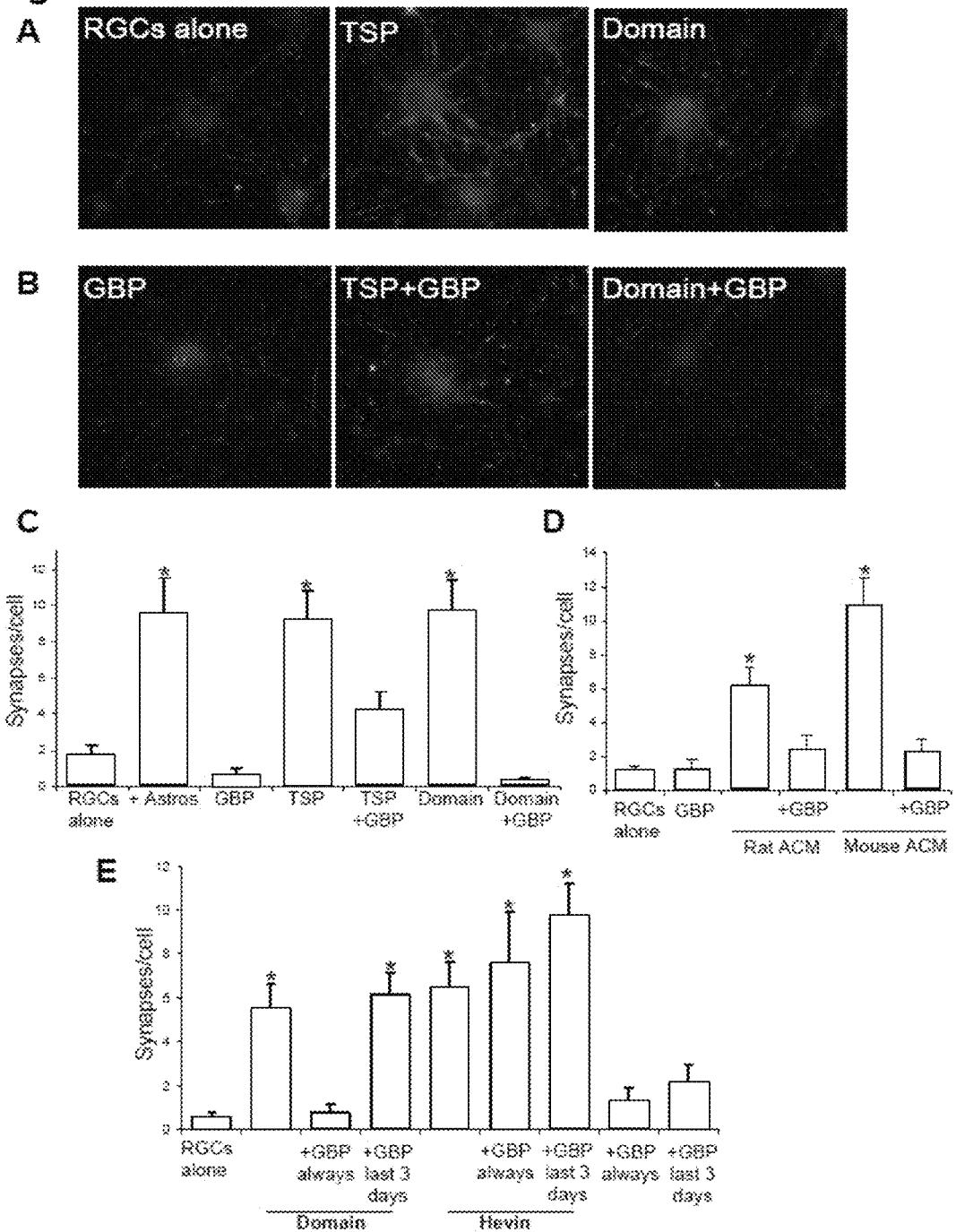
FIGS. 3A-E: Gabapentin blocks TSP induced synapse formation in vitro.

FIG. 3A shows immunostaining of RGCs for co-localization of presynaptic Synaptotagmin and postsynaptic PSD-95 showed few co-localized synaptic puncta when cultured alone but many in the presence of purified TSP1 or the recombinant TSP2 EGF-like domains.

Gabapentin (GBP, 32 µM) a drug that binds to calcium channel subunit alpha2delta blocked the synaptogenic effect of TSP1 or the TSP2 EGF-like domains, as shown in FIG. 3B. FIG. 3C, quantification of the effects of Gabapentin on TSP induced synapse formation. Gabapentin (32 µM) addition to TSP1 or TSP2 EGF-like domains reduces the number of synapses formed by RGCs down to background levels. FIG. 3D, gabapentin blocks the synaptogenic effect of astrocyte conditioned media (ACM). RGCs cultured in the presence of rat or mouse ACM formed 5-10 fold higher number of synapses when compared to RGCs cultured alone. Addition of Gabapentin (32 µM) diminished the synaptogenic effect of both rat and mouse ACM.

FIG. 3E, gabapentin blocks formation of new synapses but can not break down already-formed synapses or synapses formed by another synaptogenic protein Hevin. 3 DIV RGCs were treated with purified recombinant TSP2 EGF-like domains (20 nM) or Hevin (30 nM) for 9 days in vitro. Both the EGF-like domains and Hevin increased the number of synapses formed significantly when compared to RGCs cultured alone. Similar to (C) addition of Gabapentin (GBP) together with EGF-like domains diminished its synaptogenic effect. However, addition of Gabapentin to RGCs treated with EGF-like domains at day 6 for an additional 3 days did not decreased the synapse number indicating that Gabapentin did not breakdown already formed synapses, but rather blocked formation of new synapses. Gabapentin addition to Hevin, another astrocyte secreted protein that can induce formation of structural synapses, did not affect Hevin's synaptogenic function regardless of the time it was added. (*$p<0.05$, n=20, error bars indicate SEM values).

Methods

Purification and Culture of RGCs.

RGCs were purified by sequential immunopanning to greater than 99.5% purity from P5 Sprague-Dawley rats (Simonsen Labs, Gilroy, Calif.), as previously described (Barres et. al. (1988) *Neuron* 9, 791). Approximately 30,000 RGCs were cultured per well in 24-well plates (Falcon) on glass (Assistant) or Aclar 22C (Allied Signal) coverslips coated with poly-D-lysine (10 µg/ml) followed by laminin (2 µg/ml). RGCs were cultured in 600 µl of serum-free medium, modified from Bottenstein and Sato (1979), containing Neurobasal (Gibco), bovine serum albumin, selenium, putrescine, tri-iodo-thyronine, transferrin, progesterone, pyruvate (1 mM), glutamine (2 mM), CNTF (10 ng/ml), BDNF (50 ng/ml), insulin (5 µg/ml), and forskolin (10 µM). Recombinant human BDNF and CNTF were generously provided by Regeneron Pharmaceuticals.

Purified human platelet TSP1 was from either Sigma or Haematologic Technologies with similar results. Recombinant TSP2 was purified from serum-free medium conditioned by baculovirus-infected insect cells expressing mouse TSP2. Since purified TSP1 is readily available, we used this as the source of TSP in our experiments unless otherwise stated TSPs were used at a concentration of 5 µg/ml unless otherwise specified. RCGs were cultured for 4 days to allow robust process outgrowth and then cultured with TSPs for an additional 6 days. All other reagents were obtained from Sigma.

Preparation of Astrocytes and ACM.

Cortical glia were prepared as described by McCarthy, J. de Vellis, *J. Cell Biol.* 85, 890 (1980). Briefly, postnatal day 1-2 cortices were papain-digested and plated in tissue culture flasks (Falcon) in a medium that does not allow neurons to survive (Dulbecco's Modified Eagle Medium, fetal bovine serum (10%), penicillin (100 U/ml), streptomycin (100 µg/ml), glutamine (2 mM) and Na-pyruvate (1 mM). After 4 days non-adherent cells were shaken off of the monolayer and cells were incubated another 2-4 days to allow monolayer to refill. Medium was replaced with fresh medium containing AraC (10 µM) and incubated for 48 hours. Astrocytes were trypsinized and plated onto 24-well inserts (Falcon, 1.0 µm) or 10 cm tissue culture dishes.

For preparation of ACM, confluent cultures of astrocytes in 10 cm dishes were washed 3× in PBS and fed with 10 mls RGC medium (without CNTF, BDNF or forskolin). ACM was harvested after 4-6 days of conditioning, filtered through a 0.2 µm syringe filter and concentrated 10× through a 5 KD molecular weight cut-off centrifuge concentrator (Millipore), unless otherwise indicated. ACM was used at a final concentration of 5× unless otherwise indicated. RCGs were cultured for 4 days to allow robust process outgrowth and then cultured with ACM or an astrocyte-feeding layer for an additional 6 days.

Synaptic Assays.

For synapse quantification, cultures were fixed for 7 min in 4% paraformaldehyde (PFA), washed 3× in phosphate buffered saline (PBS) and blocked in 100 µL of blocking buffer (50% Antibody Buffer (0.5% bovine serum albumin, 0.5% Triton X-100, 30 mM NaPO4, 750 mM NaCl, 5% normal goat serum, and 0.4% NaN3, pH 7.4), 50% goat serum (NGS), 0.1% Triton-X) for 30 min. After blocking, coverslips were washed 3× in PBS and 100 µL of primary antibody solution was added to each cover slip, consisting of rabbit anti-synaptotagmin (cytosolic domain, Synaptic Systems) and mouse anti-PSD-95 (6G6-1C9 clone, Affinity Bio Reagents) diluted 1:500 in antibody buffer. Coverslips were incubated overnight at 4° C., washed 3× in PBS, and incubated with 100 µL of secondary antibody solution containing Alexa-594 conjugated goat anti-rabbit and Alexa-488 conjugated goat anti-mouse (Molecular Probes) diluted 1:1000 in antibody buffer. Following incubation for 2 h at room temperature, coverslips were washed five times in PBS and mounted in Vectashield mounting medium with DAPI (Vector Laboratories Inc) on glass slides (VWR Scientific). For presynaptic activity assay, rabbit synaptotagmin antiserum was generated by immunization with a peptide corresponding to the N-terminal luminal portion of synaptotagmin. This serum was added at 1:500 to live cultures and incubated for 6 hours. Cells were then washed 3× in DPSB, fixed and stained as above, except for the omission of synaptotagmin antibody from the primary antibody solution.

Mounted coverslips were imaged using Nikon Diaphot and Eclipse epifluorescence microscopes (Nikon). Healthy cells that were at least 2 cell diameters from their nearest neighbor were identified and selected at random by eye using DAPI fluorescence. 8-bit digital images of the fluorescence emission at both 594 nm and 488 nm were recorded for each selected cell using a cooled monochrome CCD camera and SPOT image capture software (Diagnostic Instruments, Inc). Each single-channel image was adjusted to remove unused portions of the pixel value range and the used pixel values were adjusted appropriately to utilize the entire pixel value range. Corresponding channel images were then merged to create a color (RGB) image containing the two single-channel images as individual color channels. These manipulations were performed automatically using the custom software package SpotRemover (©2001 Barry Wark).

Colocalized puncta were identified using a custom-written plug-in. Full documentation of the puncta-counting algorithm is available in the "Puncta Analyzer" plug-in's source code. Briefly, the rolling ball background subtraction algorithm was used to remove low-frequency background from each image channel. The puncta were "masked" in the single-channel image by thresholding the image so that only legitimate synaptic puncta remained above threshold. ImagerJ's "Particle Analyzer" plug-in was then used to identify and characterize puncta within each channel. Puncta in different color channels were defined as colocalized if the centers of two circles, centered at the puncta's centroids and with areas equal to the puncta's area, were less than the larger of the two circle's radius apart. Number, mean area, mean minimum and maximum pixel intensities, and mean pixel intensities for all synaptotagmin, PSD-95, and colocalized puncta in the image were recorded and saved to disk for later analysis.

Immunohistochemistry.

Brain sections were dried 30 min at 37° C. followed by application of blocking buffer. Slides were washed 3×5 min in PBS. Primary used were diluted into antibody buffer as follows: TSP1 (P10, mouse monoclonal, Immunotech, 1:200 or Ab 8, Neomarkers, rabbit, 1:200), synaptotagmin (rabbit polyclonal, Synaptic Systems, 1:500), ezrin (monoclonal 3C12, Neomarkers, 1:200), SV2 (hybridoma supernatant, Developmental Studies Hybridoma Bank, 1:30), Bassoon (Stressgen, 1:400), PSD-95 (monoclonal 6G6-1C9, Affinity Bioreagents, 1:250) and incubated overnight at 4° C. followed by 3× washes in PBS. Secondary Alexa-conjugated antibodies (Molecular Probes) were added at 1:1000 for 2 hours at RT. Slides were washed 3× in PBS and mounted in Vectashield plus DAPI.

Confocal Analysis of Synapse Number.

Images of immunostained brains were collected on a Leica SPS SP2 AOBS confocal microscope. Optical sections were line-averaged and collected at 0.28 µM intervals. Gain, threshold, and black levels were individually adjusted per section to cover the same range of pixel values, or were set for the WT sections and kept constant for all sections. In both cases equivalent results were obtained for the relative number of synapses in WT or KO animals. Stacks of 20 optical sections were quantified for synapse number by projecting a series of 5 optical sections, a number empirically determined to optically section the entirety of most synaptic puncta, and counting the number of synapses in each projection volume. Synapses were automatically counted using the ImageJ puncta analyzer program and the accuracy of the counts confirmed by counting by hand. N=6 hemispheres for P8 WT and KO and N=10 hemispheres and for P21 WT and KO. On average 3 stacks per hemisphere were obtained yielding a total of 18 stacks (72 optical sections) for synaptic puncta analysis for P8 brains and a total of 30 stacks (120 optical sections) for synaptic puncta analysis for P21 brains.

Example 2

The Calcium Channel Subunit α2δ1 is the Neuronal TSP Receptor Involved in Synapse Formation To determine whether α2δ1 plays a role in TSP-induced synapse formation in vitro, we overexpressed α2δ1 in RGCs and determined whether TSP-induced synapse formation was affected. RGCs which overexpress α2δ1 formed twice as many synapses in response to SD2 as did RGCs transfected with GFP alone (FIG. 4A) indicating that α2δ1 overexpression enhances TSP-induced synapse formation. α2δ1 overexpression alone was not sufficient to induce synapse formation in the absence of TSP indicating that TSP-α2δ1 interaction is required for the initiation of synapse formation.

Figure 4:
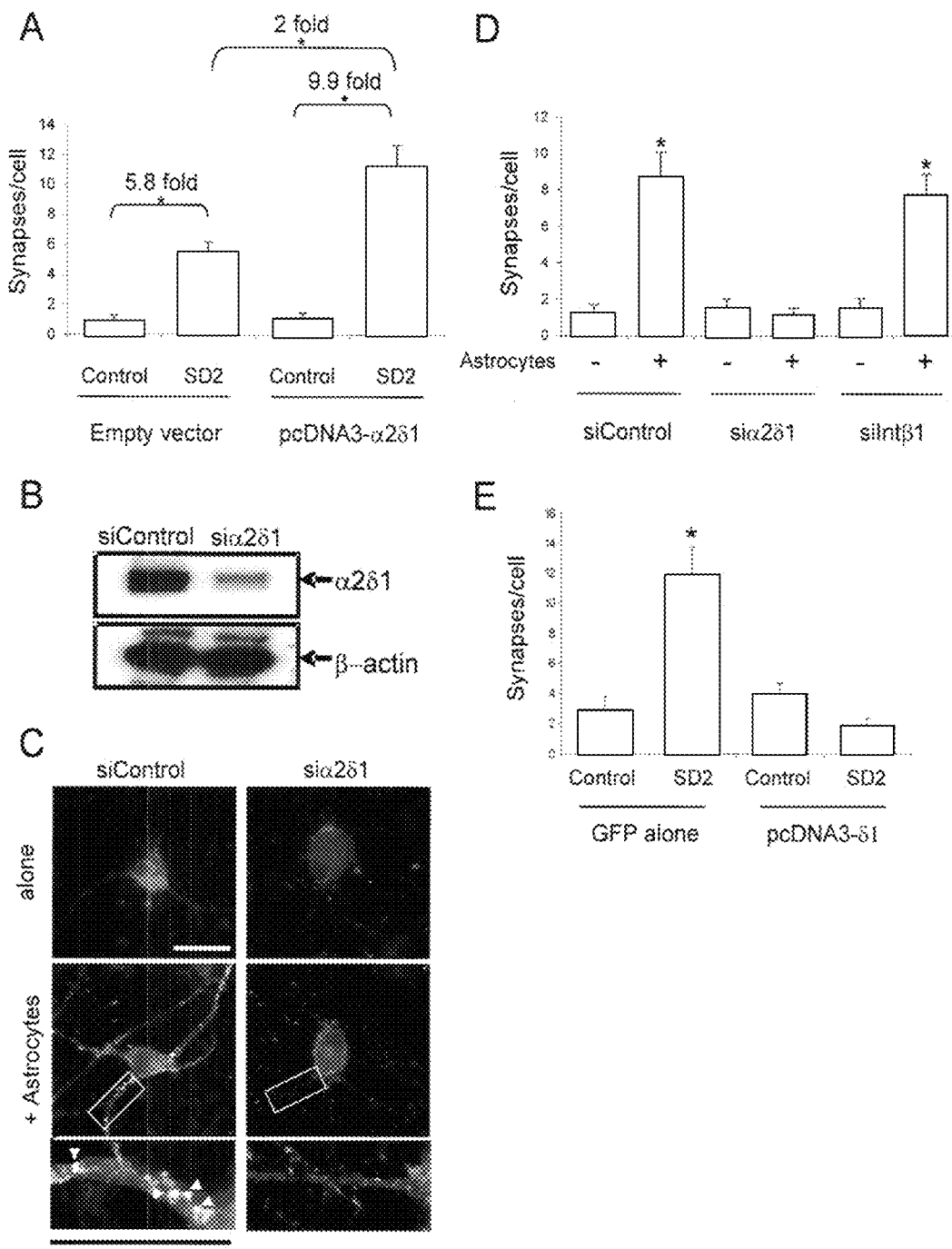
FIG. 4A: Calcium channel subunit α2δ1 is the TSP receptor involved in synaptogenesis. RGCs were transfected with empty vector (pcDNA3, Invitrogen) or a vector that expresses α2δ1 (pcDNA3-α2δ1). The synapses received by transfected cells (marked by GFP co-expression) were then quantified. In RGCs transfected with an empty vector the cells responded to the synaptogenic domain of TSP (SD2) by increasing the number of synapses formed over 5 fold. Overexpression of α2δ1 enhanced the ability of TSP to induce synapse number 2 fold. n=20 cells, Error bars mean±SEM, *p<0.05.
FIG. 4B: Calcium channel subunit α2δ1 is the TSP receptor involved in synaptogenesis. α2δ1 expression can be knocked down by a specific siRNA pool (Dharmacon) directed against α2δ1 mRNA. Western blot analysis of cell lysates from HEK293 cells, which were co-transfected with an expression vector for rat α2δ1 and siControl or siα2δ1 pools, with a monoclonal antibody against α2δ1 showed that α2δ1 expression was specifically knocked down by the siα2δ1 pool. Same samples were blotted with an antibody against β-actin that served as the loading control.
FIG. 4C: Calcium channel subunit α2δ1 is the TSP receptor involved in synaptogenesis. Immunostaining of siRNA transfected RGCs (marked blue by GFP co-expression) for co-localization of presynaptic synaptotagmin and postsynaptic PSD-95. RGCs form few synaptic puncta in the absence of astrocytes (alone), but many in the presence of astrocytes when they are transfected with the non-targeting siControl pool. On the other hand RGCs that were transfected with siα2δ1 did not form many synapses even in the presence of astrocytes. Scale bars=30 μm.
FIG. 4D: Calcium channel subunit α2δ1 is the TSP receptor involved in synaptogenesis. Quantification of the effects of siRNA pools on astrocyte-induced synapse formation in RGCs. RGCs transfected with the non-targeting siControl pool or with a targeting siRNA pool against another TSP receptor integrin β1 (siIntβ1) still formed many synapses in response to astrocytes, however in RGCs transfected with siα2δ1 pool, astrocyte-induced synapse formation was inhibited. n=20 cells, Error bars mean±SEM, *p<0.05.
FIG. 4E: Calcium channel subunit α2δ1 is the TSP receptor involved in synaptogenesis. Quantification of the effects of δ1 overexpression on TSP-induced synapse formation in RGCs. RGCs that were transfected with a vector expressing only the δ1 portion of the α2δ1 were assayed for TSP-induced synapse formation. The synapses received by transfected cells were quantified. RGCs transfected with a vector expressing GFP alone responded to the synaptogenic domain of TSP (SD2) by increasing the number of synapses formed significantly, however the overexpression of δ1 blocked the ability of SD2 to induce synapse formation. n=20 cells, Error bars mean±SEM, *p<0.05.

To further determine whether α2δ1 is required for TSP induced synapse formation, a small interfering RNA (siRNA) knockdown approach was used. A siRNA pool specific for rat α2δ1 significantly reduced the expression of rat α2δ1 in transfected HEK293 cells (FIG. 4B). RGCs were transfected with this siRNA pool against rat α2δ1 or with siRNA control pools. Knockdown of α2δ1 strongly inhibited astrocyte or TSP induced synapse formation in vitro (FIG. 4C, 4D and data not shown) whereas neither the non-targeting control siRNA pool (siControl) nor the targeting siRNA pool against the rat integrin β1 protein, which is another TSP receptor present at RGC synapses, affected synapse formation (FIG. 4C, 4D). These results demonstrate that α2δ1 is necessary for TSP and astrocyte induced synapse formation in vitro. Because only synapses on GFP-expressing cells were counted in both the α2δ1 overexpression and knockdown experiments, these results also indicate that α2δ1 is acting on the postsynaptic side and is necessary for the cells ability to receive synapses.

Example 3

α2δ1-Promoted Synapse Formation does not Depend on Calcium Channel Function or Number In order to find out whether α2δ1 promotes synapse formation through its ability to modulate biophysical properties of calcium channels, whether the δ1 subunit could still enhance TSP-induced synapse formation was tested. To do so, δ1 was overexpressed in RGCs and analyzed for its effect on SD2-induced synapse formation. Overexpression of δ1 subunit did not mimic the effect of full-length α2δ1. On the contrary, the δ1 subunit acted as a dominant negative construct and led to inhibition of SD2-induced synapse formation (FIG. 4E). Similarly, δ1 subunit expression also blocked astrocyte-induced synapse formation (data not shown). These results indicate that α2δ1 does not mediate its effect on synapse formation through modulating biophysical properties of the calcium channel. In addition, the enhancement of TSP-induced synapse formation by α2δ1 requires the presence of the α2 subunit of the receptor, which contains the VWF-A domain. Furthermore, the dominant negative effect of the δ subunit suggests that the δ subunit is required for transmitting the synapse-inducing signal upon TSP-α2 interaction.

Figure 5:
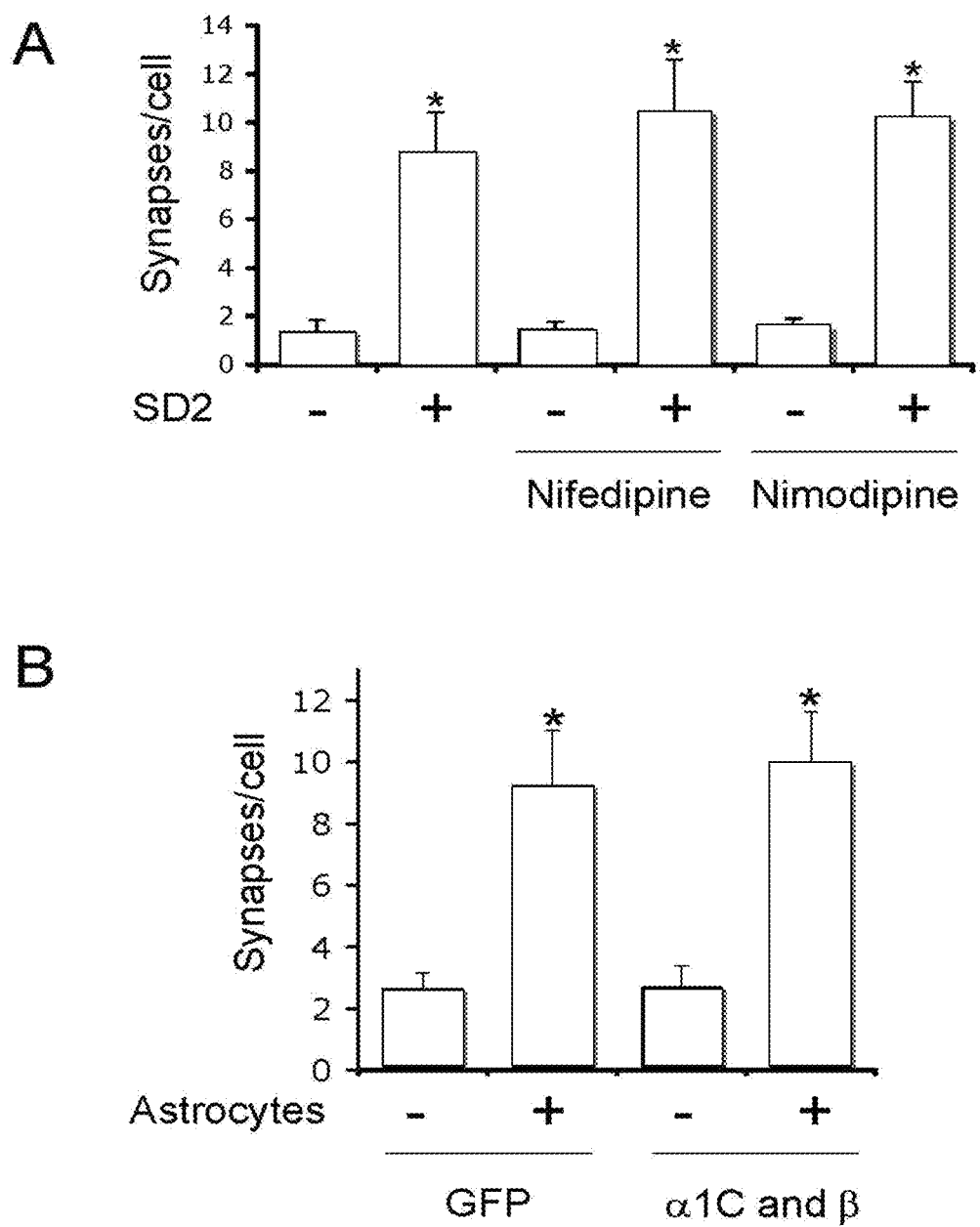
FIG. 5A. Calcium channel function or expression levels do not effect TSP/astrocyte induced synapse formation in vitro. Quantification of the effect of L-type calcium channel blockers nimodipine and nifedipine (Sigma) on the synaptogenic activity of SD2. SD2 was able to induce a significant increase in synapse number even in the presence of nifedipine or nimodipine (4 and 0.5 μM, respectively) indicating that L-type calcium channel function is not required for the synaptogenic function of TSP. n=20 cells, Error bars mean±SEM, *p<0.05.
FIG. 5B. Calcium channel function or expression levels do not effect TSP/astrocyte induced synapse formation in vitro. Quantification of the effect of overexpression of L-type calcium channel subunits α1C and β in astrocyte induced synapse formation. Overexpression of α1C and β subunits did not have any positive or negative effect on the astrocytes ability to induce synapse formation. n=20 cells, Error bars mean±SEM, *p<0.05.

Further investigation was conducted to determine whether the role of α2δ1 in synapses formation is linked to its ability to increase calcium currents via increasing surface calcium channel number. Previously, we found that astrocytes increase the total number of calcium channels at the RGC cell surface (Ullian et al., Science 291:657-661, 2001). This increase is small and concurrent with synapse formation rather than preceding it, making it unlikely to be the cause of synapse formation. To directly test whether voltage gated calcium channel (VGCC) function was required for synapse formation, the L-type calcium channel blockers nimodipine and nifedipine were added to the RGC culture medium to determine if this decreased SD2-induced synapse formation (FIG. 5A). Blocking L-type channel function, which accounts for the majority of the calcium currents in RGCs (Ullian et al., Science 291:657-661, 2001) and is predominantly postsynaptic, had no effect on TSP-induced synapse formation, even though RGC survival was negatively affected by the presence of these drugs. Similarly blockers for pre-synaptic N and P/Q type channels (Conotoxin GV1A, Conotoxin MVIIA, Agatoxin IVA and Conotoxin MVIIC) did not block TSP-induced synapse formation (data not shown).

Finally, investigation was conducted to determine whether increasing postsynaptic L-type calcium channel expression in RGCs would enhance synapse formation in a similar way to overexpression of α2δ1. To do so, L-type calcium channel α1C and β subunits were overexpressed in RGCs and analyzed for their effect on astrocyte induced synapse formation. Overexpression of α1 and β subunits had no positive or negative effect on synapse formation in the presence or absence of astrocytes (FIG. 5B). These results suggest that neither calcium channel function, nor an increase in calcium channel number, is the driving force behind TSP-induced synapse formation, however, α2δ1-VGCC interaction may still be important for the signaling events leading to the initiation of TSP-induced synapse formation. Together these observations providing further evidence that the α2δ1-TSP interaction may induces synapse formation through a yet unknown function of α2δ1.

Example 4

Figure 6:
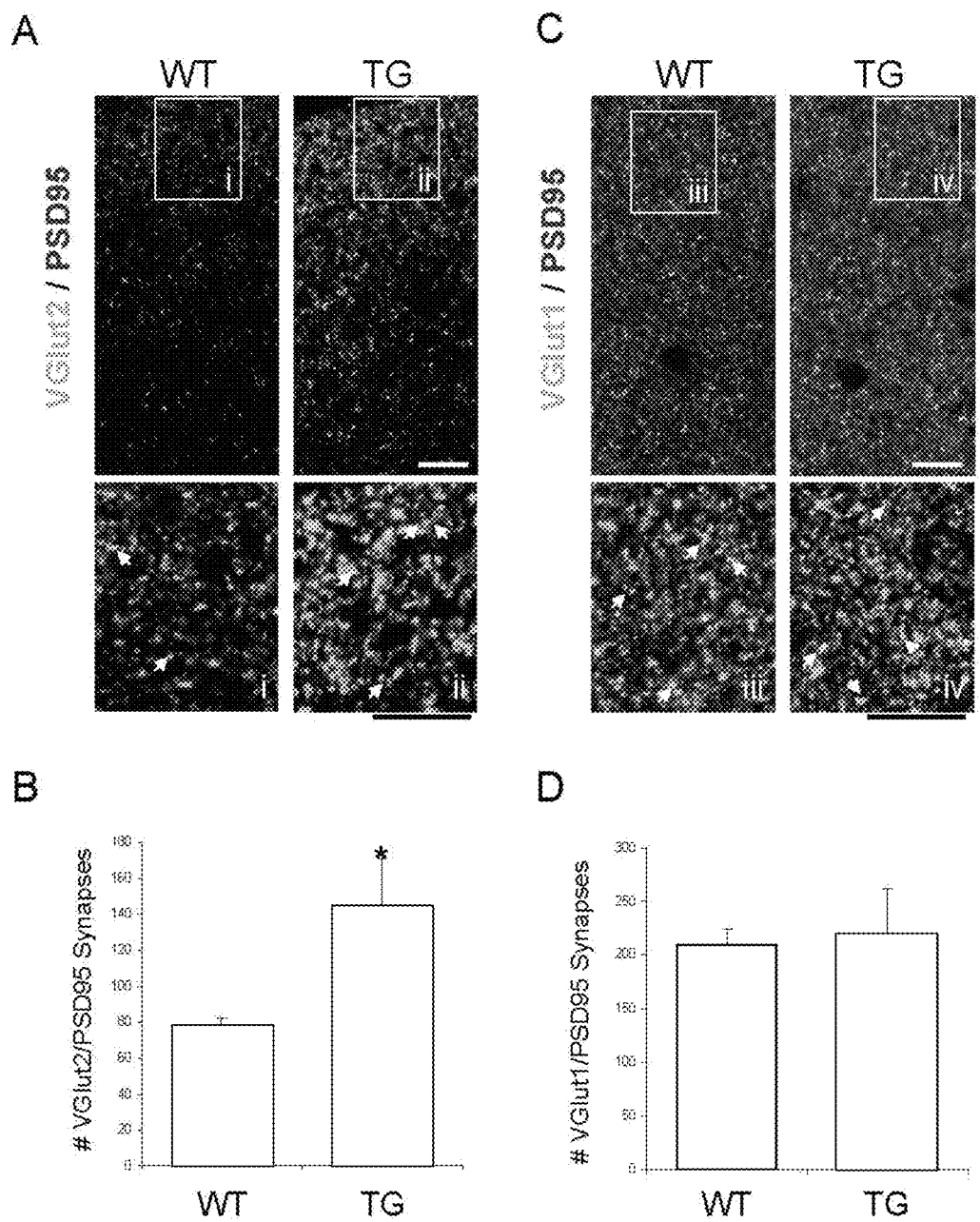
FIG. 6A: α2δ1 overexpression in vivo increases excitatory synapse number. Cortices from littermate wildtype (WT) and α2δ1 overexpressing transgenic (TG) P21 mice were immunolabeled for pre-synaptic VGlut2 and post-synaptic PSD95. Number of co-localized VGlut2/PSD95 puncta (white arrows in inlays i and ii) was noticeably higher in the TGs then the WTs. Scale bars=20 μm.
FIG. 6B: α2δ1 overexpression in vivo increases excitatory synapse number. Quantification of co-localization of pre- and post-synaptic markers VGlut2 and PSD95 in brain sections from WT and TG mice. TG brains showed around a 1.6 fold increase in the number of VGlut2-PSD95 synapses when compared to WT brains (*p<0.05).
FIG. 6C: α2δ1 overexpression in vivo increases excitatory synapse number. Cortices from WT and TG mice were also immunolabeled for VGlut1 and PSD95. Numbers of co-localized VGlut1/PSD95 puncta (white arrows in inlays i and ii) were similar in the TGs and the WTs. Scale bars=20 μm.
FIG. 6D: α2δ1 overexpression in vivo increases excitatory synapse number. Quantification of co-localization of pre- and post-synaptic markers VGlut1 and PSD95 in brain sections from WT and TG mice. Similar numbers of co-localized VGlut1/PSD95 synapses were observed in TG brains compared to WT brains.

Overexpression of α2δ1 in Neurons Enhances Synapse Formation In Vivo

α2δ1 knockouts are early embryonic lethal; therefore, it is difficult to test the effect of α1δ1 on synapse formation in vivo. As an alternative approach, synapse number was examined in mice that overexpress α2δ1 specifically in neurons, under the control of the Thy1 promoter (Li et al., Pain 125: 20-34, 2006). These transgenic mice are hypersensitive to mechanical and thermal stimulation due to spinal hyperexcitability and have elevated levels of α2δ1 protein throughout the CNS. We investigated whether these mice have higher levels of excitatory synapses in the cortex. Sagital brain sections from 21-day-old (P21) transgenic and wildtype littermate mice were co-immunostained with antibodies directed against postsynaptic density protein 95 (PSD95) and either the pre-synaptic vesicular glutamate transporter 1 or 2 (VGlut1 and VGlut2, respectively). The number of co-localized pre and postsynaptic puncta was quantified to determine the synaptic density in the cortices of these mice. Transgenic mice overexpressing α2δ1 had significantly higher numbers of VGlut2 positive excitatory synapses in the cortex when compared with the littermate wildtype controls (FIGS. 6A and B). On the other hand, the number of VGlut1 positive excitatory synapses was similar for both the transgenic and the wildtype mice (FIGS. 6C and D). The observation that α2δ1 overexpression specifically increases VGlu5 positive synapses is interesting. One possible explanation is that in these mice the α2δ1 transgene is specifically overexpressed in neurons that establish VGlut2 positive synapses. In conclusion, the increase in the number of VGlut2/PSD95 synapses in α2δ1 overexpressing mice shows that α2δ1 plays a role in promoting excitatory synapse formation in the brain.

Example 5

Figure 7:
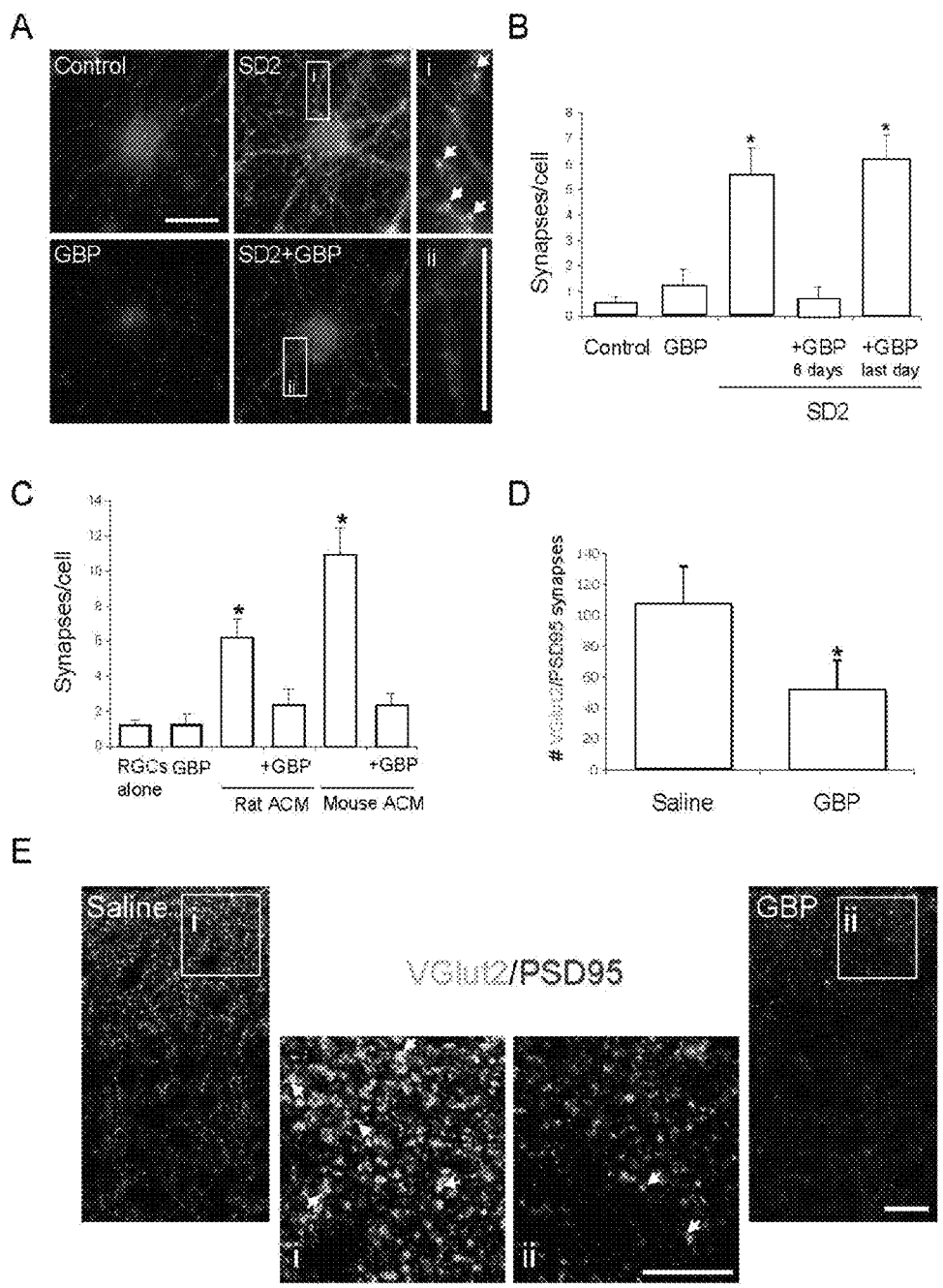
FIG. 7A: Gabapentin inhibits TSP/astrocyte induced synapse formation. Immunostaining of RGCs for co-localization of presynaptic synaptotagmin (red) and postsynaptic PSD-95 shows few synaptic puncta when RGCs are cultured alone, but many in the presence of SD2. Addition of GBP at 32 μM concentration from the beginning of the SD2 treatment inhibited TSP induced synapse formation visualized by the lack of co-localized pre and post-synaptic puncta in SD2 plus GBP condition (inlays i versus ii). Scale bars=30 μm.
FIG. 7B: Gabapentin inhibits TSP/astrocyte induced synapse formation. Quantification of the effect of GBP on SD2-induced synapse formation. GBP blocks TSPs synaptogenic effect only when added to the RGCs at the same time as the synaptogenic domain SD2. It does not decrease synapse numbers when added to the cells for the last 24 hours. n=20 cells, Error bars mean±SEM, *p<0.05.
FIG. 7C: Gabapentin inhibits TSP/astrocyte induced synapse formation. Quantification of the effect of GBP on astrocyte-induced synapse formation. RGCs were treated either with rat or mouse ACM in the presence or absence of 32 μM GBP. GBP is able to block all of ACMs synaptogenic activity. n=20 cells, Error bars mean±SEM, *p<0.05.
FIG. 7D: Gabapentin inhibits TSP/astrocyte induced synapse formation. Quantification of co-localization of pre- and postsynaptic markers VGlut2 and PSD95 in brain sections from saline and GBP injected P7 mice. GBP injected brains showed a significant decrease in the number of VGlut2-PSD95 synapses when compared to saline injected brains (*p<0.05).
FIG. 7E: Gabapentin inhibits TSP/astrocyte induced synapse formation. Saline and GBP injected P7 cortices were immunolabeled for presynaptic VGlut2 and postsynaptic PSD95. In 50% of the GBP injected mice there was a very severe reduction in the number, size and co-localization of synaptic puncta containing both pre- and postsynaptic markers VGlut2 and PSD95 (white arrows, inlays i versus ii). Scale bars=20 μm.
Figure 8:
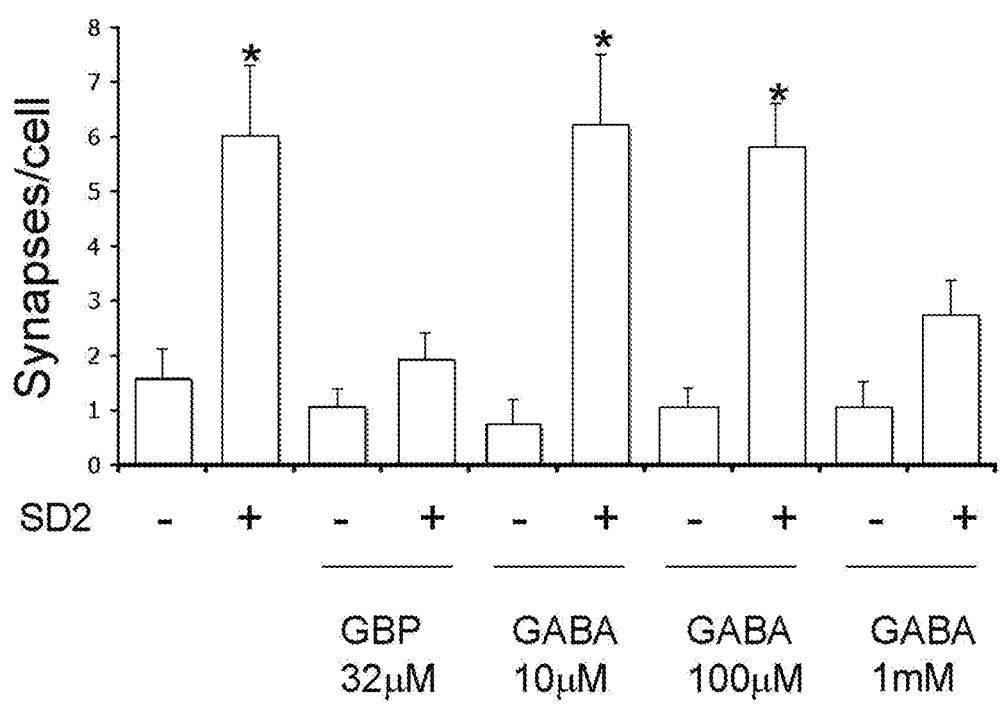
FIG. 8: GABA mimics the effect of GBP in inhibiting TSP induced synaptogenesis in culture. Quantification of the effect of GABA on SD2 induced synapse formation. GBP (32 μM) blocks the synaptogenic activity of SD2 as shown before. GABA was also inhibitory when it was added to RGCs at 1 mM concentration. GABA did not decrease the synapse numbers induced by SD2 when it was used at lower (10 and 100 μM) concentrations. n=20 cells, Error bars mean±SEM, *p<0.05.

Gabapentin, a High Affinity Ligand for α2δ1, Strongly Inhibits TSP and Astrocyte Induced Synapse Formation α2δ1 is a high affinity receptor for gabapentin. In order to determine whether gabapentin (GBP) affects TSP or astrocyte induced synapse formation, RGCs were cultured with SD2 or ACM in the presence or absence of GBP (32 µM). GBP strongly inhibited both TSP and astrocyte-induced synapse formation (FIG. 7A-C). GBP was not toxic to the RGCs (RGC survival was 62.0±2.1% in control culture media versus 66.5±4.1% in culture media containing GBP). Similarly, GBP did not affect neurite outgrowth (data not shown). Investigation was conducted to determine whether GBP could dissolve synapses that had already formed. RGCs were cultured with SD2 for 5 days to allow synapses formation and then added GBP for an additional day. Although GBP completely inhibited synapse formation induced by SD2 when it was present for the entire 6-day culture period, when GMP added SD2 for only the last 24 hours synapse formation was not affected (FIG. 7B). Thus GBP powerfully blocks new synapse formation induced by TSP and astrocytes, but does not dissolve already formed synapses. Interestingly GABA, an inhibitory neurotransmitter that binds to $\alpha 2\delta 1$ with much lower affinity (IC50=650 µM, (Suman-Chauhan et al., Eur. J. of Pharmacol. 244:293-301, 1993), also blocked TSP induced synapse formation when used at high concentrations (FIG. 8).

To determine whether GBP similarly blocks synapse formation in vivo, neonatal mice were injected with either GBP or saline, for the first postnatal week, which coincides with the initiation of synapse formation in the brain (see Experimental Procedures). Analysis was carried out to determine whether GBP-injected mice had a reduced number of glutamatergic excitatory synapses in the cortex. At this age P7 glutamatergic synapses in the cortex are predominantly VGlut2 positive (Miyazaki et al., The Eur. J. of Neuroscience, 17:2563-2572, 2003). Therefore, co-immunostaining of sagital brain sections from (P7) saline or GBP-injected, mice was carried out with antibodies against VGlut2 and PSD95 and the number of co-localized pre- and post-synaptic puncta was quantified to determine synaptic density in the cortex of these mice. There was a significant decrease in the density of excitatory synapses in the cerebral cortex of the GBP injected mice in comparison to saline injected control mice (FIG. 7D). This difference was mainly due to a severe decrease in synapse number in half of the GBP injected animals. In this half of the mice that responded to GBP, the VGlut2/PSD95 synaptic densities went down profoundly to less than 10% of the saline injected values, although there was no apparent effect on the number of neurons. GBP injection affected both VGlut2 and PSD95 puncta by reducing their number, size, and co-localization (FIG. 7E) similar to its effect on synaptic puncta in vitro (FIG. 7A). The other half of the GBP injected group had a similar synaptic density as the saline injected controls. It is interesting that the effect of GBP in vivo is an "all or none" effect rather than a gradual decrease in synapse number, and that only 50% of the mice responded to GBP injection. This could be due to a critical threshold concentration of GBP necessary to be effective in blocking synapse formation, which might only be achieved in some of the mice. In three repeated experiments, however, we observed only half of the mice were affected by GBP, even when we increased the total dosage and frequency from once a day to three times per day (see below and Experimental Procedures), and even though an inbred strain of mice was used. Nevertheless, these findings show that GBP is a powerful inhibitor of new synapse formation both in vitro and in vivo.

Example 6

Figure 9:
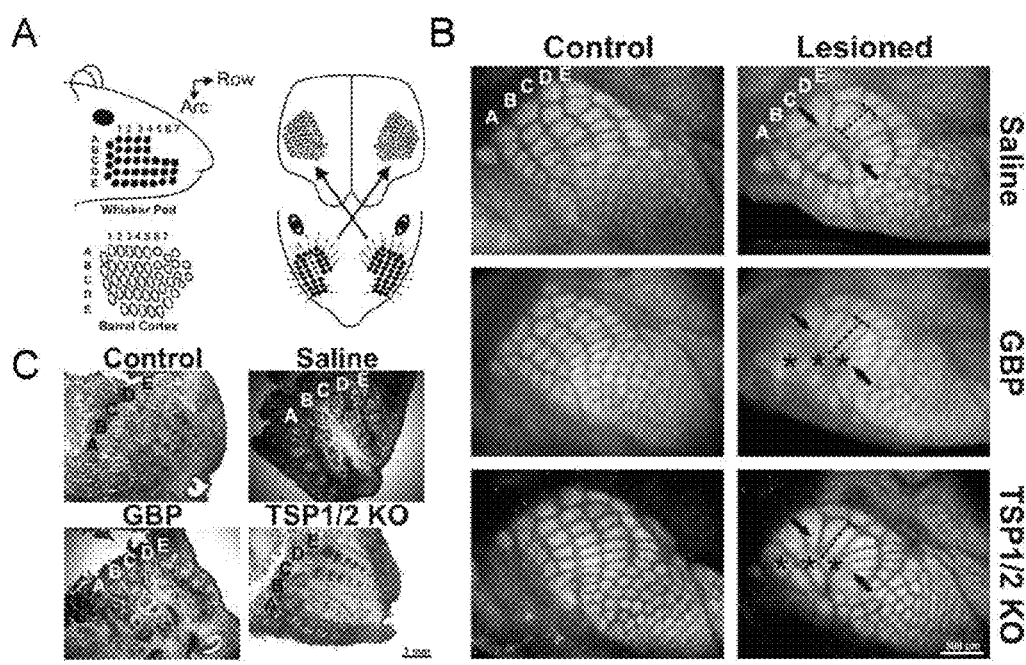
FIG. 9A: TSP induced synapse formation is involved in barrel cortex plasticity. The organization of the whisker pad is recapitulated point to point in the barrel cortex of the mouse. Schematic of the experimental paradigm: ablation of the C-row of whiskers at P1 causes corresponding contralateral barrel representations at P7 to shrink and fuse, while neighboring barrels invade the territory of deprived barrels.
FIG. 9B: TSP induced synapse formation is involved in barrel cortex plasticity. Immunostaining in tangential cortical sections with an antibody against the serotonin transporter (5-HTT) labels thalamocortical afferents to the barrel cortex. Left images show barrel cortex contralateral to intact whisker pad (unlesioned "control" side). Right images are the representative examples of lesion-induced plasticity following whisker follicle ablation in mice that were injected with saline (top), with GBP (middle). Bottom row are the control (left) and lesioned (right) barrel cortices from a TSP1/2KO mouse. Arrows flank the C-row of barrels corresponding to lesioned whiskers. Brackets and dashed lines show the expansion of D-row barrels. Asterisks denote regions of abnormal lesion-induced plasticity.
FIG. 9C: TSP induced synapse formation is involved in barrel cortex plasticity. Hematoxylin staining of the whisker pads from the same mice whose barrels are shown in (B) showing the lack of C row while the neighboring rows of follicles are still present.

Inhibition of TSP-Induced Synapse Formation Interferes with Lesion-Induced Barrel Cortex Plasticity in Neonatal Mice Understanding how the brain remodels its neuronal networks has been a major goal of neurobiology, as these processes underlie learning, memory and recovery from injury. Is astrocyte-induced synapse formation involved in remodeling neural circuits during development? To explore this question a well-established developmental plasticity paradigm, 'the barrel cortex plasticity' assay, was used. The nerves that innervate the major whiskers on the snout of the mouse project to the brain as a topographically ordered "somatotopic" map where afferent axons and target cells form ordered modules that recapitulate the structural organization seen on the whisker pad (Erzurumlu et al., The Anatomical Record 288:121-134, 2006). First, neurons of the trigeminal nerve innervate the mystacial vibrissae (whiskers) and send projections that crossover completely to the opposite side of the brain. These projections then form synapses at the brainstem (barrelettes) and their afferents then project and synapse at the thalamus (barreloids). Finally, thalamocortical axons project to the primary somatosensory cortex, where they form a somatotopic map of "barrels" with postsynaptic layer IV granule cells (FIG. 9A). To test whether TSP-induced synapse formation is involved in mechanisms of experience-dependent plasticity, we took advantage of the ability of the barrel cortex to exhibit structural changes of its circuitry in response to peripheral whisker manipulations. If a row of whiskers on the snout are deafferentated during a critical period of postnatal development (the first 3 postnatal days in mice), barrels in the cortex corresponding to the lesioned row of whiskers shrink and fuse together, while cells in neighboring barrels invade the territory vacated by projections from the lesioned whiskers (Van der Loos and Woolsey, Science 179:395-546, 1973). These changes can be visualized by analyzing the barrel cortex on postnatal day 7 (P7) (FIG. 9A).

Figure 10:
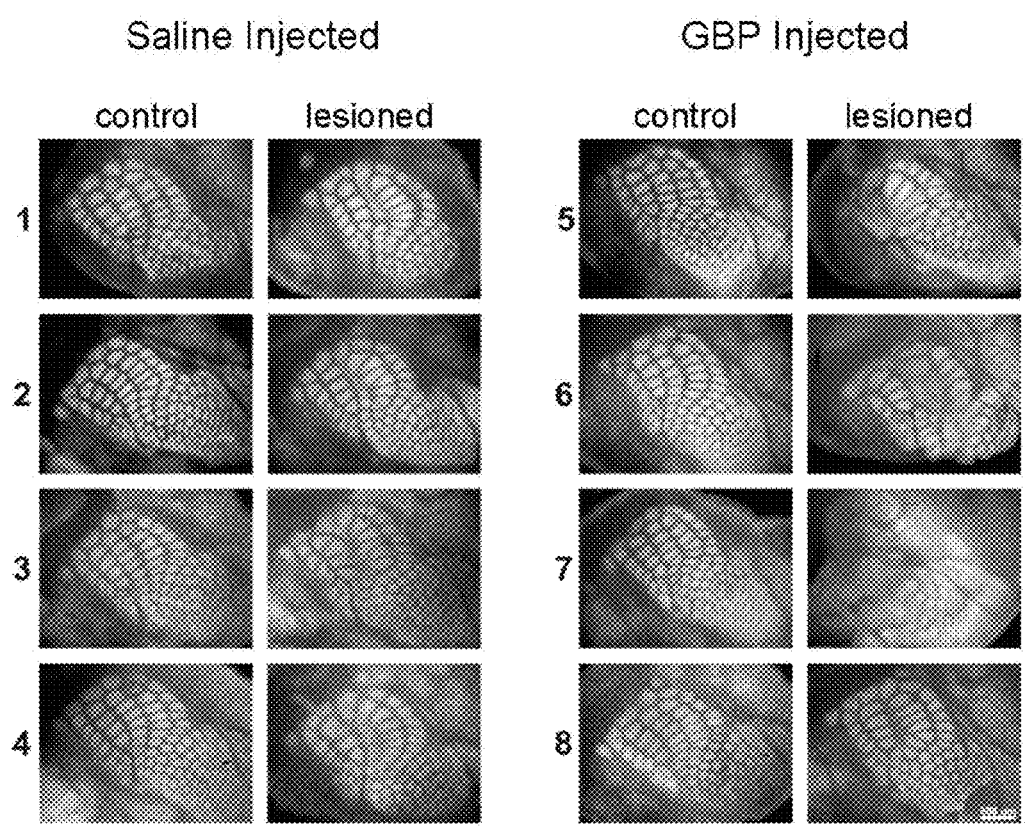
FIG. 10: A collection of the barrel cortex plasticity phenotypes in saline and GBP injected mice. Immunostaining in tangential cortical sections with an antibody against the serotonin transporter (5-HTT) labels thalamocortical afferents to the barrel cortex. For each mouse labeled 1-8, left images show barrel cortex contralateral to intact whisker pad (unlesioned-control side). Right images are the representative examples of lesion-induced plasticity following whisker follicle ablation in mice that were injected with saline (mice 1-4), with GBP (mice 5-8). GBP injection did not affect the barrel cortex formation as the barrels formed in a similar fashion to saline injected ones (mice 1-8 left panels), however, in 50% of the mice GBP injection induced aberrant barrel cortex plasticity phenotypes. In these mice typically the A, B, and C rows of the lesioned cortex lost form diffused and merged together (mouse 5). In one case only the neighboring D row merged and diffused with the C row and lost form. In one extreme case the majority of the barrel cortex had lost its shape and was diffused (mouse 7). None of the mice injected with saline ever showed these kinds of phenotypes and they all displayed normal barrel cortex plasticity (mice 1-4, right panels). Half of the GBP injected animals also displayed a normal barrel cortex plasticity phenotype (mice 8).

Two groups of neonatal mice were injected either with GBP or an equal volume of saline daily starting at P0 until P7. On P1, five whiskers from the C-row on one side of each mouse snout were surgically removed and cauterized. The mice were then sacrificed at P7 and their barrel structure corresponding to both the unlesioned "control" hemisphere and the lesioned hemisphere were analyzed. Both saline and GBP injected mice had typical barrels formed on the control side (FIG. 9B top two left panels). On the lesioned side, however, while all saline injected mice displayed a typical barrel cortex plasticity pattern, where the C row barrels corresponding to the cauterized whiskers are fused and the neighboring B and D row barrels enlarge to innervate the vacated regions. 50% of the GBP injected mice displayed an atypical plasticity response (FIG. 9B, right panels). In these mice, not only the C row, but also the A and B rows also lost form and fused, even though the analysis of the snouts showed that the whisker follicles for these rows were still present and undisturbed in these mice (FIGS. 9B and 9C, for a collection of phenotypes please see FIG. 10).

Because GBP strongly blocks TSP and astrocyte mediated synaptogenesis, these findings suggest that astrocyte secreted TSPs induce the synapse formation required for rewiring of the barrels post injury. Blocking TSP-induced synapse formation may lead to the loss of a "stop and connect" signal, thus the axons still continue to seek for an appropriate target which results in failure of the barrels to reform. In order to more directly test the role of TSPs, barrel cortex plasticity in TSP1/2 double knockout (KO) mice was examined. A third of the TSP1/2KO mice analyzed showed a very similar, aberrant barrel cortex plasticity phenotype (FIG. 9B, bottom right panel), a pattern never observed in any of the wild type mice. These findings provide evidence that the main effect of GBP in barrel cortex plasticity is likely through its inhibition of astrocyte derived TSP-induced synapse formation and that TSP-induced synapse formation participates in barrel cortex plasticity in mice. Interestingly, neither the GBP injected mice nor the TSP1/2 KO mice had problems in the normal establishment of the barrels in the unlesioned-control side, suggesting that TSPs specifically play a role in synaptic remodeling-plasticity upon injury in this system.

Example 7

The Calcium Channel Subunit α2δ1 Interacts with the Synaptogenic Domain of TSP

Many domains of TSP have previously been found to interact with specific cell surface receptors, particularly integrins, however until recently there were no known receptors for the EGF-like domains of TSPs. Recently, the EGF-like domains of TSP4 were found to bind to the VWF-A domain of integrin αM (Pluskota et al., Blood, 106:3970-3978, 2005). As several other integrin α and β subunits contain VWF-A like domains (Whittaker and Hynes, Mol. Bio. of the Cell 13:3369-3387, 2002), we investigated whether integrin αM or the other VWF-A domain containing integrins were expressed by RGCs and were involved in TSP induced synapse formation. None of the integrins that contained the VWF-A domain and were expressed by RGCs were crucial for the synaptogenic activity of TSP (data not shown).

Another class of neuronal plasma membrane molecules that contains VWF-A domains is the calcium channel subunit alpha2 delta (δ2δ) family. Four α2δ subunits in mammals have been cloned to date (Klugbauer et al., J. of Bioenergetics and Biomembranes 35: 639-647, 2003). Gene expression profiling of RGCs showed high level expression of the L-type calcium channel subunit α2δ1, which was verified by RT-PCR and by Western blotting (data not shown, FIG. 11A). We therefore next investigated whether α2δ1 interacts with TSPs. We used specific polyclonal antibodies to immunoprecipitate TSPs 1, 2 and 4 from postnatal day 5 rat cerebral cortex lysate and performed Western blot analysis on the immunoprecipitated proteins using a monoclonal antibody specific for α2δ1. α2δ1 was detected in immunoprecipitations performed using each of the three TSP antibodies (FIG. 11B) providing evidence for an interaction between α2δ1 and TSPs in vivo.

Figure 11:
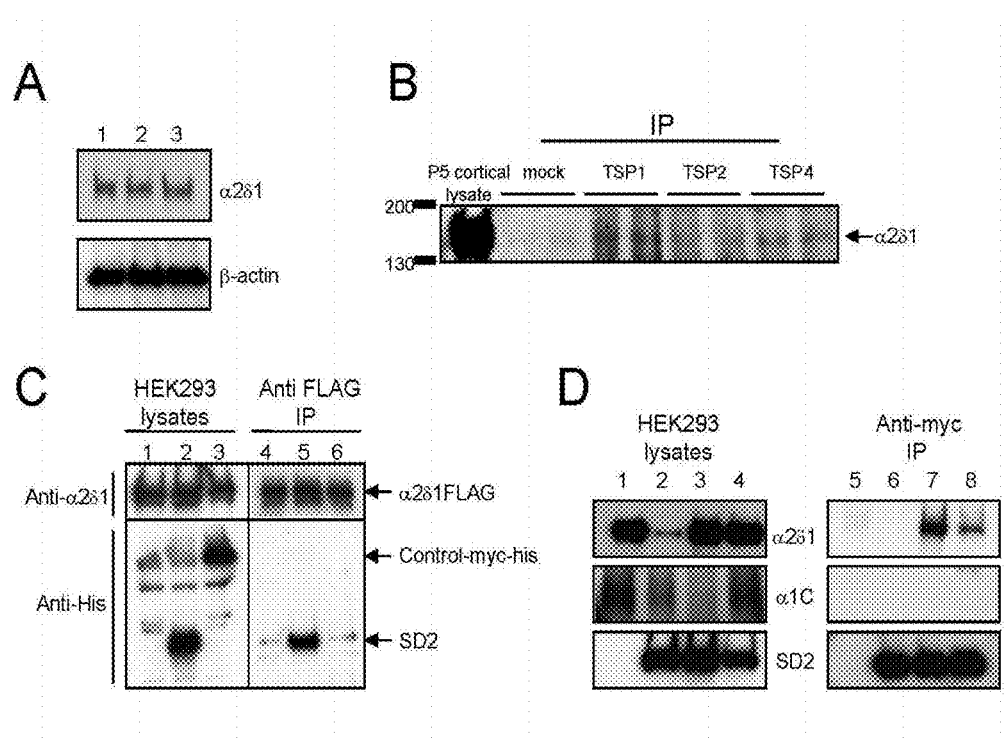
FIG. 11A: Thrombospondins interact with calcium channel subunit $\alpha2\delta1$. RGCs express calcium channel subunit $\alpha2\delta1$ in culture. Nine DIV RGC lysates were analyzed by Western blotting for the presence of $\alpha2\delta1$ protein using a monoclonal antibody against $\alpha2\delta1$. RGCs expressed $\alpha2\delta1$ when they were cultured alone (lane 1) or in the presence of astrocytes (lane 2) or in the presence of TSP1 (lane 3). $\alpha2\delta1$ levels did not change with any of these treatments. $\beta$-actin level in each sample was tested to serve as a loading control.
FIG. 11B: Thrombospondins interact with calcium channel subunit $\alpha2\delta1$. $\alpha2\delta1$ immunoprecipitates with TSP1, 2 and 4 from P5 rat brain cortical lysate. TSPs 1, 2 and 4 were immunoprecipitated from P5 cortical lysates using specific rabbit polyclonal antibodies. $\alpha2\delta1$ was detected by Western-blot analysis on the immunoprecipitation (IP) fractions. TSPs 1, 2 or 4 co-immunoprecipitated $\alpha2\delta1$, whereas no $\alpha2\delta1$ was detected in the IP fraction of a mock rabbit polyclonal antibody.
FIG. 11C: Thrombospondins interact with calcium channel subunit $\alpha2\delta1$. $\alpha2\delta1$ interacts with the synaptogenic domain of TSP2 (SD2). FLAG tagged $\alpha2\delta1$ was expressed in HEK293 cells alone (1) or in the presence of either SD2 (2) or another unrelated secreted protein Control-myc-his (3). $\alpha2\delta1$ was then immunoprecipitated from HEK293 cell membrane lysates (lanes 1 through 3) using agarose beads conjugated to an antibody against the FLAG-tag. Presence of SD2 or Control-myc-his protein in the IP fractions was analyzed by Western blotting using anti-His-tag antibody (Lanes 4-6). SD2 co-immunoprecipitated with $\alpha2\delta1$ (lane 5), while the control-his-myc protein did not (lane 6) demonstrating a specific interaction between SD2 and $\alpha2\delta1$.
FIG. 11D: Thrombospondins interact with calcium channel subunit $\alpha2\delta1$. SD2 interacts with $\alpha2\delta1$, but not with the calcium channel subunit $\alpha1C$. SD2, and calcium channel subunits $\alpha1$, $\alpha2\delta1$ and $\beta$ were co-expressed at different combinations in HEK 293 cells. Lane 1: $\alpha2\delta1$, $\alpha1C$ and $\beta$ subunits of L-type calcium channel. Lane 2: $\alpha1C$ and $\beta$ subunits and SD2. Lane 3: $\alpha2\delta1$ and SD2. Lane 4: $\alpha1C$, $\alpha2\delta1$ and $\beta$ subunits and SD2. SD2 protein was immunoprecipitated from these solubilized HEK293 membranes by utilizing its C-terminal myc-tag. Presence of calcium channel subunits $\alpha2\delta1$ or $\alpha1C$ in the IP fractions were analyzed. SD2 and $\alpha2\delta1$ were co-immunoprecipitated regardless of the absence or presence of $\alpha1$ and $\beta$ subunits (lanes 7 and 8). SD2 did not interact with $\alpha1C$ in the presence or absence of the $\alpha2\delta1$ subunit (lanes 6 and 8).

In order to determine whether there is a direct and specific binding interaction between the synaptogenic domain of TSP and α2δ1, we co-expressed a FLAG-tagged α2δ1 alone (FIG. 11C lane 1), with SD2 (lane 2) or with an unrelated secreted control protein that was sub-cloned into the same vector as SD2 and had the same C-terminal myc and 6-Histidine tags (Control-myc-his, FIG. 11C lane 3). When we immunoprecipitated α2δ1-FLAG by using beads that are conjugated to anti FLAG-tag antibody, we saw that SD2 co-immunoprecipitated with α2δ1-FLAG but the Control-myc-his protein did not (FIG. 11C, lanes 5 and 6, respectively). These data show that α2δ1 specifically interacts with the synaptogenic EGF-like domains of TSP.

To provide further evidence for the interaction between α2δ1 and SD2, we co-expressed α2δ1 and SD2 in HEK293 cells and this time immunoprecipitated SD2 from detergent solubilized HEK293 cell membrane preparations using beads conjugated with anti-myc antibody. α2δ1 co-immunoprecipitated with SD2 further showing that α2δ1 directly interacts with the synaptogenic domain of the TSPs (FIG. 11D, lane 7). To determine whether the other calcium channel subunits were required for the SD2-α2δ1 interaction, and whether the calcium channel α1 subunit interacts with SD2, we co-expressed SD2 with the L-type calcium channel α1C and β subunits in the presence or absence of α2δ1 (lanes 1, 2 and 4). The α1 subunit did not interact with SD2 even in the presence of α2δ1 (FIG. 11D, lanes 5, 6 and 8), and the amount of α2δ1 that co-immunoprecipitated with SD2 decreased when the α1 subunit was also expressed (FIG. 3D, lane 8 top, panel). Thus the synaptogenic domain of TSP specifically interacts with α2δ1 but not with the α1 subunit of the L-type calcium channel. The α2δ1-SD2 interaction was strongly dependent on the presence of magnesium ions in the buffers used for membrane preparation and immunoprecipitation (Experimental Procedures). In conclusion, these data show that α2δ1 and TSP interact through the synaptogenic domain of TSP and this interaction does not depend on the presence of other L-type calcium channel subunits.

Example 8

Preparation and Testing of the TSP2 Synaptogenic Domain Construct SD2

Figure 12:
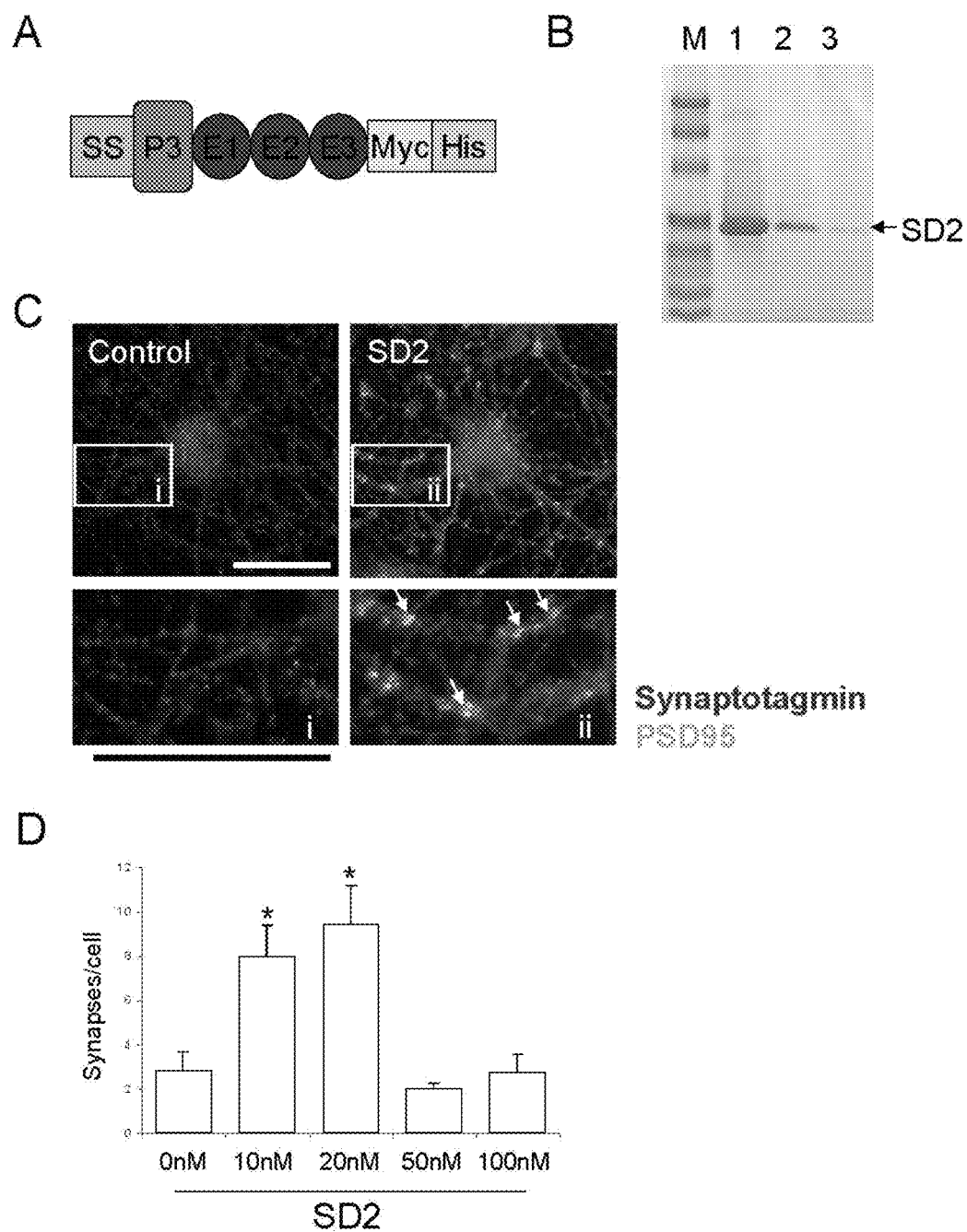
FIG. 12A: Preparation and testing of the TSP2 synaptogenic domain construct SD2. Schematic representation of the synaptogenic TSP2 construct SD2. This construct contains a signal sequence for secretion from IgG $\kappa$ chain (SS) followed by the third properdin like repeat (P3) and the three synaptogenic EGF-like repeats (E1-3) of TSP2. C-terminal myc- and His-tags were introduced for immunodetection, immunoprecipitation and purification purposes.
FIG. 12B: Preparation and testing of the TSP2 synaptogenic domain construct SD2. SD2 was produced in high amounts by overexpressing in HEK293 cells. The protein was then purified to homogeneity from culture media by using Ni-chelating chromatography. Column elution fractions that contain the pure protein were analyzed by SDS-PAGE and the purity of the protein was checked by commassie staining (lanes 1-3). M=molecular weight marker, 206, 130, 87, 42, 31, 17, and 7 kDa (BioRad).
FIG. 12C: Preparation and testing of the TSP2 synaptogenic domain construct SD2. Immunostaining of RGCs for colocalization of presynaptic synaptotagmin and postsynaptic PSD-95 shows few synaptic puncta when RGCs are cultured alone (Control), but many in the presence of SD2 (white arrows in inlay ii). Scale bars=30 µm.
FIG. 12D: Preparation and testing of the TSP2 synaptogenic domain construct SD2. Quantification of the dose response for the effect of SD2 on synapse number. SD2 was most effective in increasing the synapse number at 10-20 nM range, but lost its synaptogenic activity above 50 nM concentration. N=20 cells, error bars mean±SEM, *p<0.05.

A mammalian expression construct designed to encode a secreted monomeric TSP2 fragment that encompassed the third properdin-like repeat and the three EGF-like repeats of TSP2 was made (FIG. 12A). This recombinant protein from transfected HEK293 cell culture media to homogeneity by utilization of the C-terminal 6-Histidine tag (His-tag) was purified (FIG. 12B). This tagged and purified TSP2 fragment (designated SD2 for synaptogenic domain 2) was strongly synaptogenic (FIG. 12C, D). These synapses mimicked the synapses induced by full length TSP1, as they were presynaptically active, but postsynaptically silent (data not shown). The activity of SD2 was highest in the 10-20 nM range (FIG. 12D). At higher concentrations its activity was diminished suggesting the inhibition or desensitization of its receptor due to high ligand concentration.

Experimental Procedures for Examples 2-8

Purification and Culture of RGCs and Astrocytes

RGCs were purified by sequential immunopanning to greater than 99.5% purity from P5 Sprague-Dawley rats (Charles Rivers) and cultured in serum-free medium containing BDNF, CNTF, and forskolin on laminin-coated coverslips, as previously described (Christopherson et al., Cell 120:421-433, 2005; Meyer-Franke et al., Neuron 15:805-819, 1995; Ullian et al., Science 291:657-661, 2001). Cortical astrocyte inserts and ACM were prepared as described in (Christopherson et al., Cell 120:421-433, 2005). RCGs were cultured for 3-4 days to allow robust process outgrowth and then cultured with astrocyte inserts, ACM or TSPs for an additional 6 days.

Recombinant Proteins and DNA Constructs

Purified human platelet TSP1 was obtained from Haematologic Technologies. Recombinant TSP4 and TSP5 were expressed and purified as described in (Chen et al., J. Biol. Chem. 275:26538-26544, 2000; Lawler et al., J. Biol. Chem. 270:2809-2814, 1995). Mouse TSP3 cDNA in pcDNA3 mammalian expression vector was a gift from V. Dixit (Qabar et al., J. Biol. Chem. 269:1262-1269, 1994). TSP3 was overexpressed in Cos7 cells and the Cos7 cell conditioned media was used as a source of TSP3. In the same experiment the control conditions were treated with conditioned media from Cos7 cells transfected with empty pcDNA3 vector. The panel of TSP1 and 2 truncation constructs were expressed and purified as described before in (Mosher et al., Methods in Cell Bio. 69; 69-81, 2002; Miao et al., Cancer Research 61:7830-7839, 2001; Saumet et al., Blood 106:658-667, 2005).

Overexpression vector for α2δ1 was a kind gift from D. Lipscombe (Brown University). δ1 expression vector was a kind gift from K. Campbell (Univ. of Iowa) and is described in (Gurnett et al., J. Biol. Chem. 272:18508-18512, 1997). Vectors expressing calcium channel subunits α1C and β are described in (Dolmetsch et al., Science 294:333-339, 2001).

The synaptogenic domain of TSP2 (SD2) was cloned into pAPtag5 vector (GenHunter) between SfiI and XhoI sites. SD2 was expressed by HEK293 cells, which were transfected using Lipofectamine 2000 (Invitrogen) following manufacturers instructions. The secreted recombinant protein was then purified from conditioned culture media by Ni-chelating chromatography using Ni-NTA resin (Qiagen) following manufacturers instructions.

Synapse Assay on RGCs

For synapse quantification of RGC cultures cells were fixed for 7 minutes with 4% paraformaldehyde (PFA), washed three times in phosphate-buffered saline (PBS), and blocked in 100 μl of a blocking buffer containing 50% normal goat serum and 0.1% Triton X-100 for 30 minutes. After blocking, coverslips were washed three times in PBS, and 100 μL of primary antibody solution was added to each coverslip, consisting of rabbit anti-synaptotagmin (1:750, cytosolic domain, Synaptic Systems) and mouse anti-PSD-95 (1:750, 6G6-1C9 clone, Affinity Bio Reagents). Coverslips were incubated overnight at 4° C., washed three times in PBS, and incubated with 100 μl of Alexa-594 conjugated goat anti-rabbit and Alexa-488 conjugated goat anti-mouse (Invitrogen) diluted 1:1000 in antibody buffer. Following incubation for 2 hours, coverslips were washed 3-4 times in PBS and mounted in Vectashield mounting medium with DAPI (Vector Laboratories Inc) on glass slides (VWR Scientific). Secondary-only controls were routinely performed and revealed no significant background staining.

Mounted coverslips were imaged using Nikon Eclipse E800 epifluorescence microscope (Nikon). Healthy cells that were at least two cell diameters from their nearest neighbor were identified and selected at random by eye using DAPI fluorescence. Eight bit digital images of the fluorescence emission at both 594 nm and 488 nm were recorded for each selected cell using a monochrome CCD camera and SPOT image capture software (Diagnostic Instruments, Inc). Merged images were analyzed for co-localized puncta by using a custom-written plug-in (Barry Wark, licensed under the GPL (see worldwide web at gnu.org/copyleft/gpl.html) for the NIH image processing package ImageJ (see worldwide web at rsb.info.nih.gov.laneproxy.stanford.edu/ij/). This analysis generates counts that are similar to the numbers obtained counting by eye was verified numerous times. It has been previously shown that increase in co-localized puncta corresponds to a real increase in the number of synapses, which were counted by electron microscopy and confirmed by electrophysiological analysis (Christopherson et al., Cell 120:421-433, 2005; Ullian et al., Science 291:657-661, 2001).

RGC Transfections

6DIV RGCs were transfected using the Lipofectamine 2000 (Invitrogen) reagent. Briefly, 300 μl conditioned culture medium from the cells was removed and saved in another tissue culture plate at 37° C. in 10% CO2 incubator. The cells were then fed with 200 μl fresh media. 1 μg DNA or 2 μl of 20 μM siRNA pool was mixed with 100 μl OptiMEM media (Invitrogen) and 2 μl Lipofectamine 2000 reagent (Invitogen). The mixture was incubated for 20 minutes at RT and was added to the cells. After 3 hours cells were washed twice with warm PBS and were fed with 200 μl of fresh RGC growth media and 300 μl of the saved conditioned media. SD2 or astrocyte insert treatments started 1 day post-transfection for plasmid constructs and 2 days post-transfection for siRNA pools. Transfected cells were marked by GFP that was co-transfected with each condition. Typical transfection efficiencies ranged between 10% and 15%. Cells were stained for synapses after 6 days of SD2 or astrocyte treatment as described before. In this case PSD95 was detected by using a secondary goat anti-mouse antibody conjugated to Alexa 680. Images of transfected cells were taken in three channels (488 nm for GFP, 594 nm for synaptotagmin, and 680 nm for PSD95). The number of synapses on GFP positive cells was quantified using methods described above.

Immunoprecipitations and Western Blotting

SD2, α2δ1 (untagged or FLAG-tagged) and L-type calcium channel α1C and β subunits were expressed in HEK293 cells by transient transfection using Lipofectamine 2000 (Invitrogen) following the provider's instructions, for 2 to 3 days.

HEK293 cell plasma membranes were prepared for co-immunoprecipitations as follows. Cells were washed with PBS 3 times and scraped from the tissue culture plates. The cells were pelleted and resuspended in ice-cold hypotonic buffer (10 mM Tris pH 7.4, 1 mM $CaCl_2$ and 1 mM $MgCl_2$) with protease inhibitors (Complete EDTA-free, Roche), and incubated on ice for 15 minutes for cells to swell. The cells were then disrupted by homogenization in a glass-on-glass douncer (5 times). The nuclei and unbroken cells were removed by centrifugation at 300 g for 5 minutes. The post-nuclear supernatant was centrifuged for 20 minutes at 20,000 g to pellet the membranes.

The membranes were resuspended in solubilization buffer (25 mM Tris pH 7.2, 150 mM NaCl, 250 mM Sucrose, 1 mM $CaCl_2$ and 1 mM $MgCl_2$) with protease inhibitors (Complete EDTA-free, Roche) and 0.5% Surfact-Amps NP-40 (Pierce) and were incubated at 4° C. for 10 minutes to allow for solubilization. The insoluble debris was removed by centrifugation (20,000 g for 10 minutes). The supernatant was incubated with anti-myc antibody conjugated agarose beads to immunoprecipitate SD2 (Upstate) or with anti-FLAG antibody M2 conjugated beads to immunoprecipitate FLAG-tagged α2δ1 (Sigma-Aldrich) for 4 hours or overnight at 4° C. while rotating. After binding was completed the beads were washed 4-5 times with the solubilization buffer. The bound proteins were eluted by addition of non-reducing SDS-PAGE buffer (2×, Pierce) and 5 min incubation at 37° C. The eluate was then transferred to a clean tube and β-mercapto-ethanol was added. The samples were denatured at 37° C. for 30 minutes and loaded on SDS-PAGE gels (4-15%, BioRad). After SDS-PAGE electrophoresis, proteins were transferred onto PVDF membranes and were blotted for target proteins.

TSP immunoprecipitations were carried out as follows. Five P5 rat cortices were dissected and membranes were prepared and solubilized as described above. The soluble fraction was incubated with protein A/G beads that were pre-bound to TSP1, 2 or 4 polyclonal antibodies overnight (the TSP antibodies are described in (Lawler et al., J. Biol. Chem. 270:2809-2814, 1995; Tooney et al., Matrix Biol. 17:131-143, 1998)). The beads were washed 4-5 times and the proteins were eluted and prepared for SDS-PAGE analysis as described above.

The calcium channel subunit α2δ1 was detected in Western blots by using a monoclonal antibody (Sigma, 1:1000). SD2 and the myc-tagged control protein both contained C terminal 6-His tags and they were recognized in Western blot by using a monoclonal anti-penta-Histidine antibody (Qiagen, 1:1000). Calcium channel subunit α1C was detected with a rabbit polyclonal antibody (Chemicon, 1:1000). Horseradish peroxidase conjugated anti-mouse or anti-rabbit (1:5000)

were used as secondary antibodies (Jackson Labs) and the detection was performed with an ECL kit from Amersham.

Synapse Assay on Mouse Brain Sections

Brains were immersed in 4% paraformaldehyde (PFA), fixed overnight at 4° C., and cryo-protected in 30% sucrose. For synaptic staining, tissue was embedded in a 2:1 mixture of 20% sucrose:OCT in PBS, and cryo-sectioned (12 µm). Sections were dried at 37° C., washed three times in PBS, and blocked with 20% normal goat serum (NGS, Invitrogen) in PBS 1 hr. Primary antibodies were diluted in PBS with 0.3% triton and 10% NGS as follows: PSD95 (Zymed, rabbit, 1:500) and VGlut1 and VGlut2 (Chemicon, guinea pig, 1:2500) incubated overnight at 4° C. Secondary Alexa-conjugated antibodies (goat anti-guinea pig Alexa 488 and goat anti-rabbit Alexa 594, Invitrogen) were added at (1:200 in same buffer) for 2 hr at room temperature in dark. Slides were mounted in Vectashield with DAPI and were imaged using a Zeiss LSM 510 confocal laser-scanning microscope.

Three independent sagital brain sections per animal were stained with pre- and post-synaptic markers and 5 µm confocal scans were performed (optical section width 0.38 µm, 14 optical sections each) at the cortex. To ensure consistency of the cortical area to be scanned, the outer cortical region, including the synaptic layer of the cortex dorsal to the dentate-gyrus were picked in each section. The parameters for scanning were always setup for wild-type (or saline injected) brain sections and same imaging parameters were used for transgenic (or GBP injected) animals. Merged single optical section images at 1 µm intervals were analyzed using the ImageJ-puncta analyzer option to count for number of co-localized pre- and post-synaptic puncta (5 optical sections per brain section and 15 total images per brain). Average synaptic density per imaged area was calculated for each condition.

Mice

TSP1/2 double knockout mice on an FVB background were used (n=12) (Agah et al., Matrix Biol. 22:539-47, 2004). Wildtype mice with FVB background were purchased from Charles River Laboratories. Brains from P21, α2δ1 overexpressing, transgenic animals and their littermate wild-type controls (n=8) were provided by Li and colleagues and are described in (Li et al., Pain 125:20-34, 2006).

Saline and Gabapentin Injections:

In three independent experiments, two litters of wild type mice (n=3×12, FVB background) were given daily intraperitoneal injections of either a single dose of 400 mg/kg of GBP (Sigma-Aldrich) or a matching volume of saline solution (PBS). In one experiment the mice were injected with 200 mg/kg GBP (n=6) three times a day and the controls received the same volume of saline solution (n=6). Pups were weighed just before injections to determine the dose administered and also to follow their weight gain and general health, which showed no differences between GBP and saline injected mice. Samples were blinded during analysis of the barrel cortex plasticity.

Whisker Lesions:

All whisker lesions removed whisker follicles from the center row (row C) on the right whisker pad of P1 mice. Neonatal mice were held on their left side under a dissecting scope and received two parallel incisions with a surgical blade flanking the row of whiskers to be removed. The skin between the incisions was pulled back with forceps. Follicles were individually removed with forceps at the opening. The lesion site was then cauterized with silver nitrate using flexible caustic applicators (Tech-Med). Mice were then allowed to recover in their home cage.

Barrel Cortex Immunohistochemistry:

Mice were sacrificed at P7 and brains were dissected and immersion fixed in 4% paraformaldehyde for 12 to 24 hours. Brains were cryoprotected in 30% sucrose in PBS until they sank to the bottom of the solution (24-48 hours). Brains were then hemisected along the midline, and 40-µm-thick sections were cut tangential to the barrel cortex of each hemisphere on a Leica SM2000R freezing microtome and placed in PBS. Barrel cortex staining was performed on free-floating sections. First, sections were placed in a blocking solution of 10% NGS and 0.25% Triton-X-100 in PBS for 45 minutes at RT. Sections were then incubated with anti-serotonin (5-HT) transporter rabbit polyclonal antibody (Calbiochem) at 1:400 in blocking solution for one hour at room temperature, and then overnight at 4° C. After 3 washes in PBS, tissue sections were incubated with goat anti-rabbit Alexa 594 secondary antibody (Invitrogen) at 1:1000 in blocking solution for 90 minutes at room temperature to allow fluorescent detection of the primary antibody. After 3 washes in PBS, sections were mounted on glass slides (VWR), in the order in which they were cut, and mounted with Vectashield Mounting Medium (Vector Laboratories). Sections were visualized using a Nikon Eclipse E800 fluorescent microscope, and images were digitally acquired using an SPOT camera (Diagnostic Instruments, Sterling Heights, Mich.).

Barrel Cortex Reconstructions:

To reassemble complete maps of the barrel cortex, 5-HTT stained images from serial sections were reconstructed in Photoshop (Adobe Systems). One section, usually with most of the barrel cortex already in plane, was selected as the base image upon which data from adjacent sections were layered. Each added section was first carefully aligned to match the previous sections, and then only the portions of the barrel field labeled more brightly in added sections were revealed with a layer mask. This process was repeated until the entire primary barrel cortex was visible. Contrast and brightness levels were then carefully matched between layers to attain a more accurate representation of the level of signal across the entire reconstructed barrel field.

Whisker Pad Staining:

The whole snout region was immersion fixed in 4% paraformaldehyde and then cryoprotected in 30% sucrose in PBS overnight. Snouts were hemisected along the midline, and trimmed back to only contain the whisker pads. Whisker pads were then flattened and embedded in 2:1 30% sucrose: O.C.T. Sections were cut at 50 µm and collected on positive coat slides (Sigma) using a Leica CM3050 cryostat. Sections were dried at 37° C. for 30 to 90 minutes, and then washed with PBS once and stained with Mayer's Hematoxylin (Lillie's Modification) (Dako) for 30 seconds. Slides were rinsed in deionized distilled water and coverslipped with Faramount aqueous mounting medium (Dako). Brightfield microscopy was performed with the Nikon Eclipse E800 microscope, and images were digitally acquired using an SPOT camera (Diagnostic Instruments).

Example 9

Intrathecal Bolus Injection of Active Anti-TSP4 Antibody or TSP4 Antisense Oligodeoxynucleotides Reverses Allodynia in Spinal Nerve Injured Rats To test if TSP4 protein could induce behavioral hypersensitivity and gabapentin could block the induction, the following experiments were carried out. Active or heat inactivated TSP4 protein dissolved in saline was injected on day 0, and behavioral hypersensitivity test was conducted daily as described in the Experimental Procedures. Gabapentin or saline was injected three days after TSP4 (45 ug/rat) bolus injection, followed by behavioral test 1 hour later and then daily thereafter. As shown in FIG. 13A, intrathecal bolus injection of active, but not heat-inactivated TSP4 protein into L5/6 spinal cord segments of naive rats caused a gradual reduction in their hindpaw withdrawal thresholds to von Frey filament (mechanical) stimulation in a dose-dependent manner (FIG. 13A). The behavioral hypersensitivity had an onset time of two days post injection and peaked about 2-4 days post injection, and lasted over a week post TSP4. TSP4 induced behavioral hypersensitivity was reversible, and the reversal time was about five days post the peak effect time. The behavioral hypersensitivity induced by TSP4 was blocked by intrathecal injection of gabapentin (1 mg/rat, bolus i.t. injection), but not saline. The gabapentin effects lasted over one day. Since gabapentin binds to the calcium channel α2δ1 subunit, these data support that TSP4-induced allodynia is likely mediated by interacting with the calcium channel α2δ1 subunit. The slow reversal of the gabapentin effects suggested a chronic, rather than acute, mechanism of the drug actions.

To determine if TSP4 plays a role in mediating neuropathic pain processing at the spinal cord level, the effect of intrathecal TSP4 antisera in reversing established allodynia in spinal nerve ligated rats was examined. Intrathecal bolus injection of active TSP4 antibody (chicken polyclonal, from Dr. Frank Zaucke at University of Cologne, Cologne, Germany) was administered into left L5/6 spinal nerve ligated rats 2-weeks post injury, when the injured rats had fully developed allodynia. The bolus TSP4 antibody reversed established allodynia at the injury side in a dose-dependent manner (FIG. 13B-C). Injection with the heat-inactivated (boiled) anti-TSP4 antibody did not show any effect in allodynia reversal (FIG. 13B-C). The effects of active antisera (80 ug/rat, bolus i.t. injection) in allodynia reversal had an onset time of 4 hrs and duration of over 10 hrs (FIG. 13B). Similar active TSP4 antibody treatment did not change the base line behavioral thresholds to the same stimuli in the non-injury (contralateral) side. These data suggest that elevated TSP4 protein may play a critical role in peripheral nerve injury-induced allodynia at the spinal level, and blocking its functions at the spinal level may have therapeutic values in pain management.

To determine if similar anti-TSP4 treatment could prevent the development of injury-induced allodynia, spinal nerve ligated rats were treated pre-emptively with intrathecal daily injection of TSP4 antisera (chicken polyclonal, 80 ug/rat). The treatment started before the nerve ligation surgery. As shown in FIG. 13D, pre-emptive intrathecal TSP4 antiserum treatment did not alter the base line thresholds in the non-injury (right) side, but prevented the onset of allodynia in the injury (left) side of spinal nerve ligated rats in comparison to the injured rats treated with intrathecal injection of saline. The TSP4 antibody effects lasted over 2 days after the last injection. These data that injury-induced TSP4 protein may play a critical role in the initiation of allodynia at the spinal level and blocking TSP4 function may have therapeutic benefits in neuropathic pain prevention.

To determine if TSP4 antisense oligodeoxynucleotides can block injury-induced tactile allodynia, two TSP4 antisense oligodeoxynucleotides (#1 and #2) complementary to two different regions of the TSP4 mRNA were intrathecally injected into spinal nerve ligated rats 5 weeks post injury when the injured rats had established allodynia at the injury side. As shown in FIG. 13E, daily intrathecal injection of TSP4 antisense #1 (50 ug/day) for four days had some effects in allodynia reversal, but similar treatment with antisense, not mismatch #2, caused a complete reversal of established allodynia in the injury (ipsilateral) side to a level similar to that observed in the non-injury (contralateral) side. The antisense effects had a 3-day onset time, peaked one day after the 4-day treatment, and lasted for 3 days after the last injection. Neither the antisense nor mismatch oligodeoxynucleotides altered the behavioral thresholds at the non-injury side. These data that blocking injury-induced TSP4 expression with antisense oligodeoxynucleotides may represent another approach in blocking the effects of spinal TSP4 in pain processing.

Experimental Procedures for Example 9

Surgery and Behavioral Testing

Male Harlan Sprague Dawley rats (100-150 g, Harlan Industries Indianapolis, Ind.) were housed in separate cages, exposed to a 12/12 h day/night cycle and allowed free access to food and water. Peripheral nerve injury was induced in isoflurane-anesthetized animals with tight ligation of the left L5/6 spinal nerves between DRG and the beginning of the spinal nerve (Kim and Chung, Pain 50 50:355-363, 1992). To access tactile allodynia, paw withdrawal threshold (PWT) was determined using the up-down method of Dixon (Dixon, Ann. Rev. Pharma. & Toxico. 20:441-462, 1980) with von Frey filaments (Stoelting, Wood Dale, Ill., USA) as described previously (Chaplan et al., J. Neuros. Methods 53:55-63, 1994). Briefly, animals were allowed to acclimate for 30 min in a clear plastic cubicle with a wire-mesh base. A 2 g calibrated filament was first applied to the left hindpaw plantar surface with a pressure causing the filament to bend. If no paw lifting was detected after 5 s the next filament with increasing weight was used. If a paw lifting was observed, the next weaker filament was used. This paradigm was used for a total of six measurements, starting from the one before the first change in response, or five responses (assigned a score of 0.25 g) were reached. The 50% response thresholds were calculated as described previously (Luo et al., J. Neurosci. 21:1868-75, 2001).

Intrathecal Antisense Oligodeoxynucleotides

An antisense oligodeoxynucleotide #1 against the translation initiation region of the target gene was designed and has been shown to be effective in knocking down the expression of other target genes (Wahlestedt et al., Nature 363:260-263, 1993; Ji et al., PNAS 91:12540-12543, 1994; Hua et al., J. Neurochem. 70:688-698, 1998; Li et al., J. Neurosci. 24:8494-8499, 2004). Oligodeoxynucleotide #2 based on a segment of rat TSP4 mRNA sequence was also designed and has been used for producing primers in real-time PCR experiments (TaqMan Gene Expression Assay ID: Rn014934317, Applied Biosystems), and is specific to the TSP 4 mRNA. Mismatch oligodeoxynucleotides, which contain the same number of nucleotides but in a random order (not complementary to any particular region of TSP4 mRNA), were used as controls. Since a single base mismatch would reduce binding affinity about 500-fold (Freier, 1992), the mismatch oligodeoxynucleotides should have very low affinity to TSP4 mRNA. The nucleic acid sequences for these regions of rat TSP4 gene, and the antisense and mismatch oligodeoxynucleotides are shown below:

Rat TSP4 cDNA sequence corresponding to the translation initiation region (initiation codon underlined):

5' CgtatgAccATGAttAcgCC 3' (SEQ ID NO:1; Genbank accession #: X89963) Oligodeoxynucleotides:

```
                                              (SEQ ID NO: 2)
       Antisense #1:  5' GGCGTAATCATGGTCATACG 3'

(SEQ ID NO: 3)
       Mismatch #1:  5' CGGAGTCATGATCGTAATCG 3'
```

Rat TSP4 cDNA sequence corresponding to the region for the real-time PCR primers:
5'GGAAGATAGCAACAATGATGG 3' (SEQ ID NO:4; Genbank accession #: X89963) Oligodeoxynucleotides:

```
                                              (SEQ ID NO: 5)
   Antisense #2: 5' CCATCATTGTTGCTATCTTCC 3'

(SEQ ID NO: 6)
   Mismatch #2:  5' ACCATCGTTGTTACTTTCTCC 3'
```

These antisense and mismatch sequences were not complementary to any sequences of other rat genes as indicated by BLAST search results in rat genome database. It had been shown that oligodeoxynucleotides with phosphorothioate modification have increased potential for crossing lipid bilayers, and reduce nuclease cleavage (Crooke, et al., Ann. Rev. Pharmacology. & Toxicology, 1996). Limited phosphorothioate modification on only three nucleotides at both ends of the oligodeoxynucleotides was used, and this method of modification does not cause inflammatory side effects in vivo (Li et al., J. Neurosci. 24:8494-8499, 2004). All antisense oligodeoxynucleotides used in the studies were synthesized commercially (Genelink, Inc., NY), sterilized with ethanol precipitation, and dissolved in sterile saline before use.

Drug Preparation and Intrathecal Injection

Gabapentin, purified TSP proteins and antibodies are dissolved and diluted in sterile saline before use and directly injected into the L5/6 spinal region of an isofluorane anesthetized rat in a total volume of 10 mL using a microinjector connected to a 30 G needle.

Statistics

Unpaired Student's t tests were performed, and significance was indicated by a two-tailed p value of <0.05.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims.

All technical and scientific terms used herein have the same meaning as commonly understood to one of ordinary skill in the art to which this invention belongs unless clearly indicated otherwise.

What is claimed is:

1. A method of treating neuropathic pain in an individual comprising administering to an individual having neuropathic pain an effective amount of, an antibody that binds to a thrombospondin and blocks the interaction between the thrombospondin and one or more calcium channel subunits selected from the group consisting of α2δ1, α2δ2, α2δ3, and α2δ4.

2. The method of claim 1, wherein the antibody specifically binds to an EGF-like domain of the thrombospondin.

3. The method of claim 1, wherein the antibody specifically binds to the third EGF-like domain of the thrombospondin.

4. The method of claim 1, wherein the thrombospondin is TSP1, TSP2, TSP3, TSP4, or cartilage oligomeric matrix.

5. The method of claim 1, wherein the antibody is a polyclonal antibody or a monoclonal antibody.

6. The method of claim 1, wherein the antibody is a chimeric antibody or a humanized antibody.

* * * * *

```
                            SEQUENCE LISTING

<160> NUMBER OF SEQ ID NOS: 6

<210> SEQ ID NO 1
   <211> LENGTH: 20
   <212> TYPE: DNA
   <213> ORGANISM: Artificial Sequence
   <220> FEATURE:
   <223> OTHER INFORMATION: Synthetic construct

<400> SEQUENCE: 1
cgtatgacca tgattacgcc                                           20

<210> SEQ ID NO 2
   <211> LENGTH: 20
   <212> TYPE: DNA
   <213> ORGANISM: Artificial Sequence
   <220> FEATURE:
   <223> OTHER INFORMATION: Synthetic construct

<400> SEQUENCE: 2
ggcgtaatca tggtcatacg                                           20

<210> SEQ ID NO 3
   <211> LENGTH: 20
   <212> TYPE: DNA
   <213> ORGANISM: Artificial Sequence
   <220> FEATURE:
   <223> OTHER INFORMATION: Synthetic construct

<400> SEQUENCE: 3
cggagtcatg atcgtaatcg                                           20

<210> SEQ ID NO 4
   <211> LENGTH: 21
   <212> TYPE: DNA
   <213> ORGANISM: Artificial Sequence
   <220> FEATURE:
```

```
<223> OTHER INFORMATION: Synthetic construct

<400> SEQUENCE: 4
ggaagatagc aacaatgatg g                                      21

<210> SEQ ID NO 5
<211> LENGTH: 21
<212> TYPE: DNA
<213> ORGANISM: Artificial Sequence
<220> FEATURE:
<223> OTHER INFORMATION: Synthetic construct

<400> SEQUENCE: 5
ccatcattgt tgctatcttc c                                      21

<210> SEQ ID NO 6
<211> LENGTH: 21
<212> TYPE: DNA
<213> ORGANISM: Artificial Sequence
<220> FEATURE:
<223> OTHER INFORMATION: Synthetic construct

<400> SEQUENCE: 6
accatcgttg ttactttctc c                                      21
```